US008349330B2

(12) United States Patent
Williams et al.

(10) Patent No.: US 8,349,330 B2
(45) Date of Patent: *Jan. 8, 2013

(54) THERAPEUTIC USE OF ANTI-CS1 ANTIBODIES

(75) Inventors: Marna Williams, Palo Alto, CA (US); J. Yun Tso, Menlo Park, CA (US); Nicholas F. Landolfi, Menlo Park, CA (US); David B. Powers, Fairfax, CA (US); Gao Liu, Mountain View, CA (US)

(73) Assignee: Abbott Biotherapeutics Corp., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/175,733

(22) Filed: Jul. 1, 2011

(65) Prior Publication Data

US 2012/0064067 A1    Mar. 15, 2012

Related U.S. Application Data

(63) Continuation of application No. 12/397,026, filed on Mar. 3, 2009, now Pat. No. 8,088,898, which is a continuation of application No. 10/982,357, filed on Nov. 5, 2004, now Pat. No. 7,709,610, which is a continuation-in-part of application No. 10/842,011, filed on May 7, 2004, now abandoned.

(60) Provisional application No. 60/469,211, filed on May 8, 2003, provisional application No. 60/557,620, filed on Mar. 29, 2004, provisional application No. 60/557,622, filed on Mar. 29, 2004, provisional application No. 60/557,621, filed on Mar. 29, 2004.

(51) Int. Cl.
*A61K 39/395* (2006.01)
*C07K 14/52* (2006.01)

(52) U.S. Cl. ............... 424/141.1; 424/139.1; 424/130.1

(58) Field of Classification Search ................... None
See application file for complete search history.

(56) References Cited

U.S. PATENT DOCUMENTS

| | | | |
|---|---|---|---|
| 6,478,825 | B1 | 11/2002 | Winterbottom et al. |
| 6,607,898 | B1 | 8/2003 | Kopreski et al. |
| 7,041,499 | B2 | 5/2006 | Mathew et al. |
| 7,169,565 | B2 | 1/2007 | Ruben |
| 8,008,450 | B2 | 8/2011 | Williams et al. |
| 2002/0123617 | A1 | 9/2002 | Starling et al. |
| 2003/0027986 | A1 | 2/2003 | Eaton et al. |
| 2003/0099974 | A1 | 5/2003 | Lillie et al. |

FOREIGN PATENT DOCUMENTS

| | | |
|---|---|---|
| EP | 1033401 | 9/2000 |
| WO | WO96/39518 | 12/1996 |
| WO | WO98/42738 | 10/1998 |
| WO | WO99/63088 | 12/1999 |
| WO | WO00/11150 | 3/2000 |
| WO | WO00/47602 | 8/2000 |
| WO | WO00/73454 | 12/2000 |
| WO | WO01/16318 | 3/2001 |
| WO | WO01/46260 | 6/2001 |
| WO | WO01/68848 | 9/2001 |
| WO | WO01/91793 | 12/2001 |
| WO | WO02/102993 | 12/2002 |
| WO | WO02/102994 | 12/2002 |
| WO | WO03/018621 | 3/2003 |
| WO | WO03/029423 | 4/2003 |
| WO | WO2004/029207 | 4/2004 |

OTHER PUBLICATIONS

Angel de la Fuente, et al., "Molecular characterization and expression of a novel human leukocyte cell-surface marker homologous to mouse Ly-9," Blood, vol. 97, No. 11, pp. 3513-3520 (2001).
Boles, et al., "2B4 (CD244) and CS1: novel members of the CD2 subset of the immunoglobulin superfamily molecules expressed on natural killer cells and other leukocytes," *Immunological Reviews*, vol. 181, pp. 234-249 (2001).
Boles, et al., "Molecular cloning of CS1, a novel human natural killer cell receptor belonging to the CD2 subset of the immunoglobulin superfamily," *Immunogenetics*, vol. 52, pp. 302-307 (2001).
Bouchon, et al., "Cutting edge: activation of NK cell-mediated cytotoxicity by a SAP-independent receptor of the CD2 family," *Journal of Immunology*, vol. 167, pp. 5517-5521 (2001).
Casset, et al., "A peptide mimetic of an anti-CD4 monoclonal antibody by rational design,", BBRC, vol. 307, 198-205 (2003).
Declaration of Gary Starling Under 37 C.F.R. § 1.132 dated Oct. 22, 2008 with Figure 1.
Genbank accession AB027233 (May 1999).
Genbank accession AF291815 (Aug. 2000).
Genbank accession AF390894 (Jun. 2001).
Genbank accession AF467909 (Jan. 2002).
Genbank accession AJ271869 (Mar. 2000).
Genbank accession H73135 (Oct. 1995).
Genbank accession H74227 (Oct. 1995).
Genbank accession NM_021181 (Mar. 2005).
Hillier, et al., "Generation and analysis of 280,000 human expressed sequence tags," *Genome Research*, vol. 6, pp. 807-828 (1996).
Holm, et al., "Functional mapping and single chain construction of the anti-cytokeratin 8 monoclonal antibody TS1," *Molecular Biology*, vol. 44, pp. 1075-1084 2007.
Janeway et al., *Immunobiology*, 3$^{rd}$ Edition Garland Press, pp. 3:7-3:11 (1997).
Janeway, et al., *Immunobiology*, 6$^{th}$ *Edition*, Garland Science, pp. 110-112 (2004).
Kipriyanov, et al., "Generation of Recombinant Antibodies," *Molecular Biotechnology (Review)*, vol. 12, pp. 173-201 (1999).

(Continued)

*Primary Examiner* — Yunsoo Kim
(74) *Attorney, Agent, or Firm* — Dechert LLP

(57) ABSTRACT

The present invention is directed to antagonists of CS1 that bind to and neutralize at least one biological activity of CS1. The invention also includes a pharmaceutical composition comprising such antibodies or antigen-binding fragments thereof. The present invention also provides for a method of preventing or treating disease states, including autoimmune disorders and cancer, in a subject in need thereof, comprising administering into said subject an effective amount of such antagonists.

16 Claims, 5 Drawing Sheets

OTHER PUBLICATIONS

Kumaresan, et al., "CS1, a novel member of the CD2 family, is homophilic and regulates NK cell function," *Molecular Immunology*, vol. 39, pp. 1-8 (2002).

Leo, et al., "Multiparameter analysis of normal and malignant human plasma cells: CD38++, CD56+, CD54+, clg+ is the common phenotype of myeloma cells*," *Annals of Hematology*, vol. 64, pp. 132-139 (1992).

MacCallum, et al., "Antibody-antigen interactions: Contact Analysis and Binding Site Topography," *J. Mol. Biol.*, vol. 262, pp. 732-745 (1996).

Murphy, et al., "A novel immunoglobulin superfamily receptor (19A) relates to CD2 is expressed on activated lymphocytes and promotes homotypic B-cell adhesion," *Biochem J.*, vol. 361, pp. 431-436 (2002).

Murphy, et al., "An early response gene (19A) which encodes a novel immunoglobulin superfamily member with structural similarity to CD2," *Immunology, Supplement 1*, vol. 60 (1999).

Murphy, et al., "Cell-type-specific early response gene expression during a plasmacytoid differentiation of human B lymphocytic leukemia cells," *Biochimca et Biophysica Acta*, vol. 1049, pp. 261-271 (1990).

Ni, et al., "Immunological abnormality in C3H/HeJ mice with heritable inflammatory bowel disease," *Cellular Immunology*, vol. 169, pp. 7-15 (1996).

Office Action dated Apr. 3, 2006 in connection with the U.S. Appl. No. 10/842,011.

Office Action dated Oct. 23, 2006 in connection with the U.S. Appl. No. 10/842,011.

Office Action dated Apr. 23, 2007 in connection with the U.S. Appl. No. 10/842,011 (which includes a PTO-Form 892).

Office Action dated Jan. 9, 2008 in connection with the U.S. Appl. No. 10/842,011.

Office Action dated May 18, 2007 in connection with the U.S. Appl. No. 10/982,357.

Office Action dated Sep. 10, 2007 in connection with the U.S. Appl. No. 10/982,357 (which includes a PTO-Form 892).

Office Action dated Jul. 2, 2008 in connection with the U.S. Appl. No. 10/982,357.

Office Action dated Mar. 10, 2009 in connection with the U.S. Appl. No. 10/982,357 (which includes a PTO-Form 892).

Ogura, et al., "A frameshift mutation in NOD2 associated with susceptibility to Crohn's disease," *Nature*, vol. 411, pp. 603-606 (2001).

Paul, *Fundamental Immunology*, 3$^{RD}$ Ed., p. 242 (1993).

Portolano et al., *J. Immunology*, vol. 150, pp. 880-887 (1993).

Presta, et al., "Engineering therapeutic antibodies for improved function", *Biochem Society Transactions*, vol. 30, No. 4, pp. 487-490 (2002).

Rice, et al., "Eradication of tumors in pre-clinical models of multiple myeloma by anti-cs1 monoclonal antibody HuLuc63: mechanism of action studies," *Blood*, vol. 8, No. 11, p. 1 (2006).

Ruiz-Arguelles, et al., "Cell surface markers in multiple myeloma," *Mayo Clinic Proc.*, vol. 69, pp. 684-690 (1994).

Shields, et al., "High resolution mapping of the binding site on human IgG1 for FcyRI, FcyRII, FcyRIII and FcRn and design of IgG1 variants with improved binding to the FcyR," *The Journal of Biological Chemistry*, vol. 276, pp. 6591-6604 (2001).

Shields, et al., "Lack of fucose on human IgG1 N-linked oligosaccharide improves binding to human FcyRJII and antibody-dependent cellular toxicity," *The Journal of Biological Chemistry*, vol. 277, pp. 26733-26740 (2002).

Shinkawa, et al., "The absence of fucose but not the presence of galactose or bisecting Nacetylglucosamnine of human IgG1 complex-type oligosaccharides shows the critical role of enhancing antibody-dependent cellular cytotoxicity," *The Journal of Biological Chemistry*, vol. 278, No. 5, pp. 3466-3473 (2003).

Sidorenko, et al., The dual-function CDI50 receptor subfamily: the viral attraction, *Nature Immunology*, vol. 4(1), pp. 19-24 (2003).

Tangye, et al "Functional requirements for interactions between CD84 and Src homology 2 domain-containing proteins and their contribution to human T cell activation," *The Journal of Immunology*, vol. 1761, No. 1, pp. 2485-2495 (2003).

Tovar, et al., "Mouse novel Ly9: a new member of the expanding CDI50 (SLAM) family of leukocyte cell-surface receptors," *Immunogenetics*, vol. 54, No. 6, pp. 394-402 (2002).

Tricot, et al., "Poor prognosis in multiple myeloma is associated only with partial or complete deletions of chromosome 13 or abnormalities involving 11q and not with other karyotype abnormalities," *Blood*, vol. 86, pp. 4250-4256 (1995).

Vajdos, et al, "Comprehensive Functional Maps of the Antigen-binding Site of an Anti-ErbB2 Antibody Obtained with Shotgun Scanning Mutagenesis," *J. Mol. Biol.*, vol. 320, pp. 415-428, 2002.

Van der Laan, et al., Journal of Neuroscience Research, vol. 67, pp. 191-199 (2002).

Wikipedia encyclopedia (http://en.wikipedia.org/wiki/Epitope, p. 1-2 (2007) (cited in Office Action dated Sep. 10, 2007 in connection with U.S. Appl. No. 10/892,357).

Xu, et al., "In vitro characterization of five humanized OKT3 effector function variant antibodies," *Cellular Immunology*, vol. 200, No. 1, pp. 16-26 (2000).

U.S. Appl. No. 13/174,134, filed Jun. 30, 2011.

U.S. Appl. No. 13/175,748, filed Jul. 1 2011.

Preliminary Amendment dated Jul. 1, 2011 corresponding to U.S. Appl. No. 13/175,748.

U.S. Appl. No. 13/175,751, filed Jul. 1, 2011.

Preliminary Amendment dated Jul. 1, 2011 corresponding to U.S. Appl. No. 13/175,751.

U.S. Appl. No. 13/175,759, filed, Jul. 1, 2011.

Preliminary Amendment dated Jul. 1, 2011 corresponding to U.S. Appl. No. 13/175,759.

SEQUENCE LISTING

```
<160> NUMBER OF SEQ ID NOS: 87

<210> SEQ ID NO 1
<211> LENGTH: 2672
<212> TYPE: DNA
<213> ORGANISM: Homo sapiens

<400> SEQUENCE: 1
cttccagaga gcaatatggc tggttcccca acatgcctca ccctcatcta tatcctttgg      60
cagctcacag ggtcagcagc ctctggaccc gtgaaagagc tggtcggttc cgttggtggg     120
gccgtgactt tcccctgaa gtccaaagta aagcaagttg actctattgt ctggaccttc     180
aacacaaccc ctcttgtcac catacagcca gaaggggggca ctatcatagt gacccaaaat     240
cgtaataggg agagagtaga cttcccagat ggaggctact ccctgaagct cagcaaactg     300
aagaagaatg actcagggat ctactatgtg gggatataca gctcatcact ccagcagccc     360
tccacccagg agtacgtgct gcatgtctac gagcacctgt caaagcctaa agtcaccatg     420
ggtctgcaga gcaataagaa tggcacctgt gtgaccaatc tgacatgctg catggaacat     480
```

-continued

| | |
|---|---|
| ggggaagagg atgtgattta tacctggaag gccctggggc aagcagccaa tgagtcccat | 540 |
| aatgggtcca tcctcccat ctcctggaga tggggagaaa gtgatatgac cttcatctgc | 600 |
| gttgccagga accctgtcag cagaaacttc tcaagcccca tccttgccag gaagctctgt | 660 |
| gaaggtgctg ctgatgaccc agattcctcc atggtcctcc tgtgtctcct gttggtgccc | 720 |
| ctcctgctca gtctctttgt actggggcta tttctttggt ttctgaagag agagagacaa | 780 |
| gaagagtaca ttgaagagaa gaagagagtg acatttgtc gggaaactcc taacatatgc | 840 |
| ccccattctg gagagaacac agagtacgac acaatccctc acactaatag aacaatccta | 900 |
| aaggaagatc cagcaaatac ggtttactcc actgtggaaa taccgaaaaa gatgaaaat | 960 |
| ccccactcac tgctcacgat gccagacaca ccaaggctat ttgcctatga aatgttatc | 1020 |
| tagacagcag tgcactcccc taagtctctg ctcaaaaaaa aaacaattct cggcccaaag | 1080 |
| aaaacaatca gaagaattca ctgatttgac tagaaacatc aaggaagaat gaagaacgtt | 1140 |
| gactttttc caggataaat tatctctgat gcttctttag atttaagagt tcataattcc | 1200 |
| atccactgct gagaaatctc ctcaaaccca gaaggtttaa tcacttcatc ccaaaaatgg | 1260 |
| gattgtgaat gtcagcaaac cataaaaaaa gtgcttagaa gtattcctat agaaatgtaa | 1320 |
| atgcaaggtc acacatatta atgacagcct gttgtattaa tgatggctcc aggtcagtgt | 1380 |
| ctggagttc attccatccc agggcttgga tgtaaggatt ataccaagag tcttgctacc | 1440 |
| aggagggcaa gaagaccaaa acagacagac aagtccagca gaagcagatg cacctgacaa | 1500 |
| aaatggatgt attaattggc tctataaact atgtgcccag cactatgctg agcttacact | 1560 |
| aattggtcag acgtgctgtc tgccctcatg aaattggctc caaatgaatg aactactttc | 1620 |
| atgagcagtt gtagcaggcc tgaccacaga ttcccagagg gccaggtgtg gatccacagg | 1680 |
| acttgaaggt caaagttcac aaagatgaag aatcagggta gctgaccatg tttggcagat | 1740 |
| actataatgg agacacagaa gtgtgcatgg cccaaggaca aggacctcca gccaggcttc | 1800 |
| atttatgcac ttgtgctgca aaagaaaagt ctaggtttta aggctgtgcc agaacccatc | 1860 |
| ccaataaaga gaccgagtct gaagtcacat tgtaaatcta gtgtaggaga cttggagtca | 1920 |
| ggcagtgaga ctggtggggc acgggggggca gtgggtactt gtaaaccttt aaagatggtt | 1980 |
| aattcattca atagatattt attaagaacc tatgcggccc ggcatggtgg ctcacacctg | 2040 |
| taatcccagc actttgggag gccaaggtgg gtgggtcatc tgaggtcagg agttcaagac | 2100 |
| cagcctggcc aacatggtga aaccccatct ctactaaaga tacaaaaatt tgctgagcgt | 2160 |
| ggtggtgtgc acctgtaatc ccagctactc gagaggccaa ggcatgagaa tcgcttgaac | 2220 |
| ctgggaggtg gaggttgcag tgagctgaga tggcaccact gcactccggc ctaggcaacg | 2280 |
| agagcaaaac tccaatacaa acaaacaaac aaacacctgt gctaggtcag tctggcacgt | 2340 |
| aagatgaaca tccctaccaa cacagagctc accatctctt atacttaagt gaaaaacatg | 2400 |
| gggaagggga aagggaatg gctgcttttg atatgttccc tgacacatat cttgaatgga | 2460 |
| gacctcccta ccaagtgatg aaagtgttga aaaacttaat aacaaatgct tgttgggcaa | 2520 |
| gaatgggatt gaggattatc ttctctcaga aaggcattgt gaaggaattg agccagatct | 2580 |
| ctctccctac tgcaaaaccc tattgtagta aaaaagtctt ctttactatc ttaataaaac | 2640 |
| agatattgtg agattcaaaa aaaaaaaaaa aa | 2672 |

<210> SEQ ID NO 2
<211> LENGTH: 335
<212> TYPE: PRT
<213> ORGANISM: Homo sapiens

<400> SEQUENCE: 2

| Met | Ala | Gly | Ser | Pro | Thr | Cys | Leu | Thr | Leu | Ile | Tyr | Ile | Leu | Trp | Gln |
|---|---|---|---|---|---|---|---|---|---|---|---|---|---|---|---|
| 1 | | | | 5 | | | | | 10 | | | | | 15 | |

| Leu | Thr | Gly | Ser | Ala | Ala | Ser | Gly | Pro | Val | Lys | Glu | Leu | Val | Gly | Ser |
|---|---|---|---|---|---|---|---|---|---|---|---|---|---|---|---|
| | | | 20 | | | | | 25 | | | | | 30 | | |

| Val | Gly | Gly | Ala | Val | Thr | Phe | Pro | Leu | Lys | Ser | Lys | Val | Lys | Gln | Val |
|---|---|---|---|---|---|---|---|---|---|---|---|---|---|---|---|
| | | 35 | | | | | 40 | | | | | 45 | | | |

| Asp | Ser | Ile | Val | Trp | Thr | Phe | Asn | Thr | Thr | Pro | Leu | Val | Thr | Ile | Gln |
|---|---|---|---|---|---|---|---|---|---|---|---|---|---|---|---|
| | 50 | | | | | 55 | | | | | 60 | | | | |

| Pro | Glu | Gly | Gly | Thr | Ile | Ile | Val | Thr | Gln | Asn | Arg | Asn | Arg | Glu | Arg |
|---|---|---|---|---|---|---|---|---|---|---|---|---|---|---|---|
| 65 | | | | | 70 | | | | | 75 | | | | | 80 |

| Val | Asp | Phe | Pro | Asp | Gly | Gly | Tyr | Ser | Leu | Lys | Leu | Ser | Lys | Leu | Lys |
|---|---|---|---|---|---|---|---|---|---|---|---|---|---|---|---|
| | | | | 85 | | | | | 90 | | | | | 95 | |

| Lys | Asn | Asp | Ser | Gly | Ile | Tyr | Tyr | Val | Gly | Ile | Tyr | Ser | Ser | Ser | Leu |
|---|---|---|---|---|---|---|---|---|---|---|---|---|---|---|---|
| | | | 100 | | | | | 105 | | | | | 110 | | |

| Gln | Gln | Pro | Ser | Thr | Gln | Glu | Tyr | Val | Leu | His | Val | Tyr | Glu | His | Leu |
|---|---|---|---|---|---|---|---|---|---|---|---|---|---|---|---|
| | | | 115 | | | | | 120 | | | | | 125 | | |

| Ser | Lys | Pro | Lys | Val | Thr | Met | Gly | Leu | Gln | Ser | Asn | Lys | Asn | Gly | Thr |
|---|---|---|---|---|---|---|---|---|---|---|---|---|---|---|---|
| | 130 | | | | | 135 | | | | | 140 | | | | |

| Cys | Val | Thr | Asn | Leu | Thr | Cys | Cys | Met | Glu | His | Gly | Glu | Glu | Asp | Val |
|---|---|---|---|---|---|---|---|---|---|---|---|---|---|---|---|
| 145 | | | | | 150 | | | | | 155 | | | | | 160 |

| Ile | Tyr | Thr | Trp | Lys | Ala | Leu | Gly | Gln | Ala | Ala | Asn | Glu | Ser | His | Asn |
|---|---|---|---|---|---|---|---|---|---|---|---|---|---|---|---|
| | | | | 165 | | | | | 170 | | | | | 175 | |

| Gly | Ser | Ile | Leu | Pro | Ile | Ser | Trp | Arg | Trp | Gly | Glu | Ser | Asp | Met | Thr |
|---|---|---|---|---|---|---|---|---|---|---|---|---|---|---|---|
| | | | 180 | | | | | 185 | | | | | 190 | | |

| Phe | Ile | Cys | Val | Ala | Arg | Asn | Pro | Val | Ser | Arg | Asn | Phe | Ser | Ser | Pro |
|---|---|---|---|---|---|---|---|---|---|---|---|---|---|---|---|
| | | 195 | | | | | 200 | | | | | 205 | | | |

| Ile | Leu | Ala | Arg | Lys | Leu | Cys | Glu | Gly | Ala | Ala | Asp | Asp | Pro | Asp | Ser |
|---|---|---|---|---|---|---|---|---|---|---|---|---|---|---|---|
| | 210 | | | | | 215 | | | | | 220 | | | | |

| Ser | Met | Val | Leu | Leu | Cys | Leu | Leu | Val | Pro | Leu | Leu | Leu | Ser | Leu |
|---|---|---|---|---|---|---|---|---|---|---|---|---|---|---|
| 225 | | | | | 230 | | | | | 235 | | | | 240 |

| Phe | Val | Leu | Gly | Leu | Phe | Leu | Trp | Phe | Leu | Lys | Arg | Glu | Arg | Gln | Glu |
|---|---|---|---|---|---|---|---|---|---|---|---|---|---|---|---|
| | | | | 245 | | | | | 250 | | | | | 255 | |

| Glu | Tyr | Ile | Glu | Glu | Lys | Lys | Arg | Val | Asp | Ile | Cys | Arg | Glu | Thr | Pro |
|---|---|---|---|---|---|---|---|---|---|---|---|---|---|---|---|
| | | | 260 | | | | | 265 | | | | | 270 | | |

| Asn | Ile | Cys | Pro | His | Ser | Gly | Glu | Asn | Thr | Glu | Tyr | Asp | Thr | Ile | Pro |
|---|---|---|---|---|---|---|---|---|---|---|---|---|---|---|---|
| | | 275 | | | | | 280 | | | | | 285 | | | |

| His | Thr | Asn | Arg | Thr | Ile | Leu | Lys | Glu | Asp | Pro | Ala | Asn | Thr | Val | Tyr |
|---|---|---|---|---|---|---|---|---|---|---|---|---|---|---|---|
| | 290 | | | | | 295 | | | | | 300 | | | | |

| Ser | Thr | Val | Glu | Ile | Pro | Lys | Lys | Met | Glu | Asn | Pro | His | Ser | Leu | Leu |
|---|---|---|---|---|---|---|---|---|---|---|---|---|---|---|---|
| 305 | | | | | 310 | | | | | 315 | | | | | 320 |

| Thr | Met | Pro | Asp | Thr | Pro | Arg | Leu | Phe | Ala | Tyr | Glu | Asn | Val | Ile |
|---|---|---|---|---|---|---|---|---|---|---|---|---|---|---|
| | | | | 325 | | | | | 330 | | | | | 335 |

<210> SEQ ID NO 3
<211> LENGTH: 120
<212> TYPE: PRT
<213> ORGANISM: Mus Musculus

<400> SEQUENCE: 3

| Gln | Val | Gln | Leu | Gln | Gln | Pro | Gly | Ala | Glu | Leu | Val | Arg | Pro | Gly | Ala |
|---|---|---|---|---|---|---|---|---|---|---|---|---|---|---|---|
| 1 | | | | 5 | | | | | 10 | | | | | 15 | |

| Ser | Val | Lys | Leu | Ser | Cys | Lys | Ala | Ser | Gly | Tyr | Ser | Phe | Thr | Thr | Tyr |
|---|---|---|---|---|---|---|---|---|---|---|---|---|---|---|---|
| | | | 20 | | | | | 25 | | | | | 30 | | |

-continued

Trp Met Asn Trp Val Lys Gln Arg Pro Gly Gln Gly Leu Glu Trp Ile
            35                  40                  45

Gly Met Ile His Pro Ser Asp Ser Glu Thr Arg Leu Asn Gln Lys Phe
 50                  55                  60

Lys Asp Lys Ala Thr Leu Thr Val Asp Lys Ser Ser Ser Thr Ala Tyr
 65                  70                  75                  80

Met Gln Leu Ser Ser Pro Thr Ser Glu Asp Ser Ala Val Tyr Tyr Cys
                 85                  90                  95

Ala Arg Ser Thr Met Ile Ala Thr Arg Ala Met Asp Tyr Trp Gly Gln
                100                 105                 110

Gly Thr Ser Val Thr Val Ser Ser
            115                 120

<210> SEQ ID NO 4
<211> LENGTH: 107
<212> TYPE: PRT
<213> ORGANISM: Mus Musculus

<400> SEQUENCE: 4

Asp Ile Val Met Thr Gln Ser Gln Lys Ser Met Ser Thr Ser Val Gly
 1               5                  10                  15

Asp Arg Val Ser Ile Thr Cys Lys Ala Ser Gln Asp Val Ile Thr Gly
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
 50                  55                  60

Ser Gly Ser Gly Thr Asp Phe Thr Phe Thr Ile Ser Asn Val Gln Ala
 65                  70                  75                  80

Glu Asp Leu Ala Val Tyr Tyr Cys Gln Gln His Tyr Ser Thr Pro Leu
                 85                  90                  95

Thr Phe Gly Ala Gly Thr Lys Leu Glu Leu Lys
                100                 105

<210> SEQ ID NO 5
<211> LENGTH: 119
<212> TYPE: PRT
<213> ORGANISM: Mus Musculus

<400> SEQUENCE: 5

Glu Val Lys Leu Leu Glu Ser Gly Gly Gly Leu Val Gln Pro Gly Gly
 1               5                  10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Thr Pro Ser Leu
 50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Arg Pro Asp Gly Asn Tyr Trp Tyr Phe Asp Val Trp Gly Ala Gly
                100                 105                 110

Thr Thr Val Thr Val Ser Ser
            115

```
<210> SEQ ID NO 6
<211> LENGTH: 107
<212> TYPE: PRT
<213> ORGANISM: Mus Musculus

<400> SEQUENCE: 6

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ile Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 7
<211> LENGTH: 121
<212> TYPE: PRT
<213> ORGANISM: Mus Musculus

<400> SEQUENCE: 7

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
            20                  25                  30

Trp Met Gln Trp Val Lys Gln Arg Pro Gly Gln Gly Leu Glu Trp Ile
        35                  40                  45

Gly Ala Ile Tyr Pro Gly Asp Gly Asp Thr Arg Tyr Thr Gln Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Lys Val Tyr Tyr Gly Ser Asn Pro Phe Ala Tyr Trp Gly
            100                 105                 110

Gln Gly Thr Leu Val Thr Val Ser Ala
        115                 120

<210> SEQ ID NO 8
<211> LENGTH: 107
<212> TYPE: PRT
<213> ORGANISM: Mus Musculus

<400> SEQUENCE: 8

Asp Ile Gln Met Thr Gln Ser Ser Ser Tyr Leu Ser Val Ser Leu Gly
1               5                   10                  15

Gly Arg Val Thr Ile Thr Cys Lys Ala Ser Asp His Ile Asn Asn Trp
            20                  25                  30

Leu Ala Trp Tyr Gln Gln Lys Pro Gly Asn Ala Pro Arg Leu Leu Ile
        35                  40                  45
```

```
Ser Gly Ala Thr Ser Leu Glu Thr Gly Val Pro Ser Arg Phe Ser Gly
    50                  55                  60
Ser Gly Ser Gly Lys Asp Tyr Thr Leu Ser Ile Thr Ser Leu Gln Thr
65                  70                  75                  80
Glu Asp Val Ala Thr Tyr Tyr Cys Gln Gln Tyr Trp Ser Thr Pro Trp
                85                  90                  95
Thr Phe Gly Gly Gly Thr Lys Leu Glu Ile Lys
            100                 105
```

<210> SEQ ID NO 9
<211> LENGTH: 5
<212> TYPE: PRT
<213> ORGANISM: Mus Musculus

<400> SEQUENCE: 9

```
Thr Tyr Trp Met Asn
1               5
```

<210> SEQ ID NO 10
<211> LENGTH: 17
<212> TYPE: PRT
<213> ORGANISM: Mus Musculus

<400> SEQUENCE: 10

```
Met Ile His Pro Ser Asp Ser Glu Thr Arg Leu Asn Gln Lys Phe Lys
1               5                   10                  15
Asp
```

<210> SEQ ID NO 11
<211> LENGTH: 11
<212> TYPE: PRT
<213> ORGANISM: Mus Musculus

<400> SEQUENCE: 11

```
Ser Thr Met Ile Ala Thr Arg Ala Met Asp Tyr
1               5                   10
```

<210> SEQ ID NO 12
<211> LENGTH: 11
<212> TYPE: PRT
<213> ORGANISM: Mus Musculus

<400> SEQUENCE: 12

```
Lys Ala Ser Gln Asp Val Ile Thr Gly Val Ala
1               5                   10
```

<210> SEQ ID NO 13
<211> LENGTH: 7
<212> TYPE: PRT
<213> ORGANISM: Mus Musculus

<400> SEQUENCE: 13

```
Ser Ala Ser Tyr Arg Tyr Thr
1               5
```

<210> SEQ ID NO 14
<211> LENGTH: 9
<212> TYPE: PRT
<213> ORGANISM: Mus Musculus

<400> SEQUENCE: 14

```
Gln Gln His Tyr Ser Thr Pro Leu Thr
1               5
```

-continued

<210> SEQ ID NO 15
<211> LENGTH: 5
<212> TYPE: PRT
<213> ORGANISM: Mus Musculus

<400> SEQUENCE: 15

Arg Tyr Trp Met Ser
1               5

<210> SEQ ID NO 16
<211> LENGTH: 17
<212> TYPE: PRT
<213> ORGANISM: Mus Musculus

<400> SEQUENCE: 16

Glu Ile Asn Pro Asp Ser Ser Thr Ile Asn Tyr Thr Pro Ser Leu Lys
1               5                   10                  15

Asp

<210> SEQ ID NO 17
<211> LENGTH: 10
<212> TYPE: PRT
<213> ORGANISM: Mus Musculus

<400> SEQUENCE: 17

Pro Asp Gly Asn Tyr Trp Tyr Phe Asp Val
1               5                   10

<210> SEQ ID NO 18
<211> LENGTH: 11
<212> TYPE: PRT
<213> ORGANISM: Mus Musculus

<400> SEQUENCE: 18

Lys Ala Ser Gln Asp Val Gly Ile Ala Val Ala
1               5                   10

<210> SEQ ID NO 19
<211> LENGTH: 7
<212> TYPE: PRT
<213> ORGANISM: Mus Musculus

<400> SEQUENCE: 19

Trp Ala Ser Thr Arg His Thr
1               5

<210> SEQ ID NO 20
<211> LENGTH: 9
<212> TYPE: PRT
<213> ORGANISM: Mus Musculus

<400> SEQUENCE: 20

Gln Gln Tyr Ser Ser Tyr Pro Tyr Thr
1               5

<210> SEQ ID NO 21
<211> LENGTH: 5
<212> TYPE: PRT
<213> ORGANISM: Mus Musculus

<400> SEQUENCE: 21

Ser Tyr Trp Met Gln
1               5

-continued

```
<210> SEQ ID NO 22
<211> LENGTH: 17
<212> TYPE: PRT
<213> ORGANISM: Mus Musculus

<400> SEQUENCE: 22

Ala Ile Tyr Pro Gly Asp Gly Asp Thr Arg Tyr Thr Gln Lys Phe Lys
1               5                   10                  15
Gly

<210> SEQ ID NO 23
<211> LENGTH: 12
<212> TYPE: PRT
<213> ORGANISM: Mus Musculus

<400> SEQUENCE: 23

Gly Lys Val Tyr Tyr Gly Ser Asn Pro Phe Ala Tyr
1               5                   10

<210> SEQ ID NO 24
<211> LENGTH: 11
<212> TYPE: PRT
<213> ORGANISM: Mus Musculus

<400> SEQUENCE: 24

Lys Ala Ser Asp His Ile Asn Asn Trp Leu Ala
1               5                   10

<210> SEQ ID NO 25
<211> LENGTH: 7
<212> TYPE: PRT
<213> ORGANISM: Mus Musculus

<400> SEQUENCE: 25

Gly Ala Thr Ser Leu Glu Thr
1               5

<210> SEQ ID NO 26
<211> LENGTH: 9
<212> TYPE: PRT
<213> ORGANISM: Mus Musculus

<400> SEQUENCE: 26

Gln Gln Tyr Trp Ser Thr Pro Trp Thr
1               5

<210> SEQ ID NO 27
<211> LENGTH: 137
<212> TYPE: PRT
<213> ORGANISM: Mus Musculus

<400> SEQUENCE: 27

Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
                20                  25                  30

Gly Gly Ser Leu Lys Leu Ser Cys Ala Ala Ser Gly Phe Asp Phe Ser
            35                  40                  45

Arg Tyr Trp Met Ser Trp Val Arg Gln Ala Pro Gly Lys Gly Leu Glu
        50                  55                  60

Trp Ile Gly Glu Ile Asn Pro Asp Ser Ser Thr Ile Asn Tyr Thr Pro
65                  70                  75                  80
```

-continued

Ser Leu Lys Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Pro Asp Gly Asn Tyr Trp Tyr Phe Asp Val Trp Gly
        115                 120                 125

Ala Gly Thr Thr Val Thr Val Ser Ser
    130                 135

<210> SEQ ID NO 28
<211> LENGTH: 127
<212> TYPE: PRT
<213> ORGANISM: Mus Musculus

<400> SEQUENCE: 28

Met Glu Thr His Ser Gln Val Phe Val Tyr Met Leu Leu Trp Leu Ser
1               5                   10                  15

Gly Val Glu Gly Asp Ile Val Met Thr Gln Ser His Lys Phe Met Ser
            20                  25                  30

Thr Ser Val Gly Asp Arg Val Ser Ile Thr Cys Lys Ala Ser Gln Asp
        35                  40                  45

Val Gly Ile Ala Val Ala Trp Tyr Gln Gln Lys Pro Gly Gln Ser Pro
    50                  55                  60

Lys Leu Leu Ile Tyr Trp Ala Ser Thr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Tyr Pro Tyr Thr Phe Gly Gly Gly Thr Lys Leu Glu Ile Lys
        115                 120                 125

<210> SEQ ID NO 29
<211> LENGTH: 18
<212> TYPE: PRT
<213> ORGANISM: Mus Musculus

<400> SEQUENCE: 29

Met Asp Phe Gly Leu Ile Phe Phe Ile Val Ala Leu Leu Lys Gly Val
1               5                   10                  15

Gln Cys

<210> SEQ ID NO 30
<211> LENGTH: 5
<212> TYPE: PRT
<213> ORGANISM: Mus Musculus

<400> SEQUENCE: 30

Arg Tyr Trp Met Ser
1               5

<210> SEQ ID NO 31
<211> LENGTH: 17
<212> TYPE: PRT
<213> ORGANISM: Mus Musculus

<400> SEQUENCE: 31

Glu Ile Asn Pro Asp Ser Ser Thr Ile Asn Tyr Thr Pro Ser Leu Lys
1               5                   10                  15

Asp

```
<210> SEQ ID NO 32
<211> LENGTH: 10
<212> TYPE: PRT
<213> ORGANISM: Mus Musculus

<400> SEQUENCE: 32

Pro Asp Gly Asn Tyr Trp Tyr Phe Asp Val
1               5                   10

<210> SEQ ID NO 33
<211> LENGTH: 3
<212> TYPE: PRT
<213> ORGANISM: Mus Musculus

<400> SEQUENCE: 33

Asn Tyr Ala
1

<210> SEQ ID NO 34
<211> LENGTH: 20
<212> TYPE: PRT
<213> ORGANISM: Mus Musculus

<400> SEQUENCE: 34

Met Glu Thr His Ser Gln Val Phe Val Tyr Met Leu Leu Trp Leu Ser
1               5                   10                  15

Gly Val Glu Gly
            20

<210> SEQ ID NO 35
<211> LENGTH: 11
<212> TYPE: PRT
<213> ORGANISM: Mus Musculus

<400> SEQUENCE: 35

Lys Ala Ser Gln Asp Val Gly Ile Ala Val Ala
1               5                   10

<210> SEQ ID NO 36
<211> LENGTH: 7
<212> TYPE: PRT
<213> ORGANISM: Mus Musculus

<400> SEQUENCE: 36

Trp Ala Ser Thr Arg His Thr
1               5

<210> SEQ ID NO 37
<211> LENGTH: 9
<212> TYPE: PRT
<213> ORGANISM: Mus Musculus

<400> SEQUENCE: 37

Gln Gln Tyr Ser Ser Tyr Pro Tyr Thr
1               5

<210> SEQ ID NO 38
<211> LENGTH: 119
<212> TYPE: PRT
<213> ORGANISM: Mus Musculus
```

```
<400> SEQUENCE: 38

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Pro Asp Gly Asn Tyr Trp Tyr Phe Asp Val Trp Gly Ala Gly
            100                 105                 110

Thr Thr Val Thr Val Ser Ser
        115

<210> SEQ ID NO 39
<211> LENGTH: 44
<212> TYPE: PRT
<213> ORGANISM: Homo sapiens

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
            20                  25                  30

Arg Gln Ala Pro Gly Lys Gly Leu Glu Trp Val Ala
        35                  40

<210> SEQ ID NO 40
<211> LENGTH: 32
<212> TYPE: PRT
<213> ORGANISM: Homo sapiens

<400> SEQUENCE: 40

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 41
<211> LENGTH: 119
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
    50                  55                  60

Lys Asp Lys Phe Ile Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser
            115

<210> SEQ ID NO 42
<211> LENGTH: 107
<212> TYPE: PRT
<213> ORGANISM: Mus Musculus

<400> SEQUENCE: 42

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ile Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 43
<211> LENGTH: 80
<212> TYPE: PRT
<213> ORGANISM: Homo sapiens

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Val
            20                  25                  30

Pro Lys Leu Leu Ile Tyr Gly Val Pro Ser Arg Phe Ser Gly Ser Gly
        35                  40                  45

Ser Gly Thr Asp Phe Thr Leu Thr Ile Ser Ser Leu Gln Pro Glu Asp
        50                  55                  60

Val Ala Thr Tyr Tyr Cys Phe Gly Gln Gly Thr Lys Val Glu Ile Lys
65                  70                  75                  80

<210> SEQ ID NO 44
<211> LENGTH: 107
<212> TYPE: PRT
<213> ORGANISM: Homo sapiens

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
50                  55                  60
```

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Tyr Pro Tyr
                85                  90                  95

Thr Phe Gly Gln Gly Thr Lys Val Glu Ile Lys
            100                 105

<210> SEQ ID NO 45
<211> LENGTH: 119
<212> TYPE: PRT
<213> ORGANISM: Mus Musculus

<400> SEQUENCE: 45

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Thr Pro Ser Leu
        50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Pro Asp Gly Asn Tyr Trp Tyr Phe Asp Val Trp Gly Ala Gly
            100                 105                 110

Thr Thr Val Thr Val Ser Ser
        115

<210> SEQ ID NO 46
<211> LENGTH: 87
<212> TYPE: PRT
<213> ORGANISM: Homo sapiens

<400> SEQUENCE: 46

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
                20                  25                  30

Arg Gln Ala Pro Gly Lys Gly Leu Glu Trp Val Ala Arg Phe Thr Ile
            35                  40                  45

Ser Arg Asp Asn Ala Lys Asn Ser Leu Tyr Leu Gln Met Asn Ser Leu
        50                  55                  60

Arg Ala Glu Asp Thr Ala Val Tyr Tyr Cys Ala Arg Trp Gly Gln Gly
65                  70                  75                  80

Thr Leu Val Thr Val Ser Ser
                85

<210> SEQ ID NO 47
<211> LENGTH: 119
<212> TYPE: PRT
<213> ORGANISM: Homo saiens

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Ala Pro Ser Leu
 50                  55                  60

Lys Asp Lys Phe Ile Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Pro Asp Gly Asn Tyr Trp Tyr Phe Asp Val Trp Gly Gln Gly
            100                 105                 110

Thr Leu Val Thr Val Ser Ser
            115

<210> SEQ ID NO 48
<211> LENGTH: 107
<212> TYPE: PRT
<213> ORGANISM: Mus Musculus

<400> SEQUENCE: 48

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ile Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
 50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105

<210> SEQ ID NO 49
<211> LENGTH: 80
<212> TYPE: PRT
<213> ORGANISM: Homo sapiens

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Val
            20                  25                  30

Pro Lys Leu Leu Ile Tyr Gly Val Pro Ser Arg Phe Ser Gly Ser Gly
            35                  40                  45

Ser Gly Thr Asp Phe Thr Leu Thr Ile Ser Ser Leu Gln Pro Glu Asp
 50                  55                  60

Val Ala Thr Tyr Tyr Cys Phe Gly Gln Gly Thr Lys Val Glu Ile Lys
65                  70                  75                  80

<210> SEQ ID NO 50
<211> LENGTH: 107
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Ile Ala
            20                  25                  30

Val Ala Trp Tyr Gln Gln Lys Pro Gly Lys Val Pro Lys Leu Leu Ile
        35                  40                  45

Tyr Trp Ala Ser Thr Arg His Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Ser Tyr Pro Tyr
                85                  90                  95

Thr Phe Gly Gln Gly Thr Lys Val Glu Ile Lys
            100                 105

<210> SEQ ID NO 51
<211> LENGTH: 120
<212> TYPE: PRT
<213> ORGANISM: Mus Musculus

<400> SEQUENCE: 51

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Asn Ser
            20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Lys Ser Asn Gly Lys Phe
    50                  55                  60

Lys Gly Lys Ala Thr Leu Thr Ala Asp Lys Ser Ser Arg Ala Ala Tyr
65                  70                  75                  80

Met Gln Leu Ser Ser Leu Thr Ser Val Asp Ser Ala Val Tyr Phe Cys
                85                  90                  95

Ala Arg Ser Thr Met Ile Met Thr Gly Ala Met Asp Tyr Trp Gly Gln
            100                 105                 110

Gly Thr Ser Val Thr Val Ser Ser
        115                 120

<210> SEQ ID NO 52
<211> LENGTH: 108
<212> TYPE: PRT
<213> ORGANISM: Mus Musculus

<400> SEQUENCE: 52

Asp Ile Val Met Thr Gln Ser His Lys Phe Met Ser Thr Ser Val Gly
1               5                   10                  15

Asp Arg Val Ile Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Phe Arg Tyr Thr Gly Val Pro Asp Arg Phe Thr Gly
    50                  55                  60

Ser Gly Ser Gly Thr Asp Phe Thr Phe Thr Val Ser Ser Val Gln Ala
65                  70                  75                  80

```
Glu Asp Leu Ala Val Tyr Tyr Cys Gln Gln His Tyr Ser Thr Pro Pro
            85                  90                  95

Tyr Thr Phe Gly Gly Gly Thr Lys Leu Glu Ile Lys
            100                 105
```

<210> SEQ ID NO 53
<211> LENGTH: 5
<212> TYPE: PRT
<213> ORGANISM: Mus Musculus

<400> SEQUENCE: 53

```
Asn Ser Trp Met Asn
1               5
```

<210> SEQ ID NO 54
<211> LENGTH: 17
<212> TYPE: PRT
<213> ORGANISM: Mus Musculus

<400> SEQUENCE: 54

```
Arg Ile Tyr Pro Gly Asp Gly Asp Thr Lys Ser Asn Gly Lys Phe Lys
1               5                   10                  15

Gly
```

<210> SEQ ID NO 55
<211> LENGTH: 11
<212> TYPE: PRT
<213> ORGANISM: Mus Musculus

<400> SEQUENCE: 55

```
Ser Thr Met Ile Met Thr Gly Ala Met Asp Tyr
1               5                   10
```

<210> SEQ ID NO 56
<211> LENGTH: 11
<212> TYPE: PRT
<213> ORGANISM: Mus Musculus

<400> SEQUENCE: 56

```
Lys Ala Ser Gln Asp Val Ser Thr Ala Val Ala
1               5                   10
```

<210> SEQ ID NO 57
<211> LENGTH: 7
<212> TYPE: PRT
<213> ORGANISM: Mus Musculus

<400> SEQUENCE: 57

```
Ser Ala Ser Phe Arg Tyr Thr
1               5
```

<210> SEQ ID NO 58
<211> LENGTH: 11
<212> TYPE: PRT
<213> ORGANISM: Mus Musculus

<400> SEQUENCE: 58

```
Cys Gln Gln His Tyr Ser Thr Pro Pro Tyr Thr
1               5                   10
```

<210> SEQ ID NO 59
<211> LENGTH: 120
<212> TYPE: PRT
<213> ORGANISM: Mus Musculus

```
<400> SEQUENCE: 59

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
                20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Thr Lys Tyr Asn Gly Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Thr Met Ile Ala Thr Gly Ala Met Asp Tyr Trp Gly Gln
                100                 105                 110

Gly Thr Ser Val Thr Val Ser Ser
            115                 120

<210> SEQ ID NO 60
<211> LENGTH: 107
<212> TYPE: PRT
<213> ORGANISM: Mus Musculus

<400> SEQUENCE: 60

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Gly Gly Thr Lys Leu Glu Ile Lys
            100                 105

<210> SEQ ID NO 61
<211> LENGTH: 5
<212> TYPE: PRT
<213> ORGANISM: Mus Musculus

<400> SEQUENCE: 61

Ser Ser Trp Met Asn
1               5

<210> SEQ ID NO 62
<211> LENGTH: 17
<212> TYPE: PRT
<213> ORGANISM: Mus Musculus

<400> SEQUENCE: 62

Arg Ile Tyr Pro Gly Asp Gly Asp Thr Lys Tyr Asn Gly Lys Phe Lys
1               5                   10                  15

Gly
```

```
<210> SEQ ID NO 63
<211> LENGTH: 11
<212> TYPE: PRT
<213> ORGANISM: Mus Musculus

<400> SEQUENCE: 63

Ser Thr Met Ile Ala Thr Gly Ala Met Asp Tyr
1               5                   10

<210> SEQ ID NO 64
<211> LENGTH: 11
<212> TYPE: PRT
<213> ORGANISM: Mus Musculus

<400> SEQUENCE: 64

Ile Thr Ser Thr Asp Ile Asp Asp Met Asn
1               5                   10

<210> SEQ ID NO 65
<211> LENGTH: 7
<212> TYPE: PRT
<213> ORGANISM: Mus Musculus

<400> SEQUENCE: 65

Glu Gly Asn Thr Leu Arg Pro
1               5

<210> SEQ ID NO 66
<211> LENGTH: 9
<212> TYPE: PRT
<213> ORGANISM: Mus Musculus

<400> SEQUENCE: 66

Leu Gln Ser Asp Asn Leu Pro Leu Thr
1               5

<210> SEQ ID NO 67
<211> LENGTH: 120
<212> TYPE: PRT
<213> ORGANISM: Mus Musculus

<400> SEQUENCE: 67

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
                20                  25                  30

Trp Met Asn Trp Val Lys Gln Arg Pro Gly Gln Gly Leu Glu Trp Ile
            35                  40                  45

Gly Arg Ile Tyr Pro Gly Asp Gly Asp Thr Lys Tyr Asn Gly Lys Phe
        50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Thr Met Ile Ala Thr Gly Ala Met Asp Tyr Trp Gly Gln
                100                 105                 110

Gly Thr Ser Val Thr Val Ser Ser
            115                 120

<210> SEQ ID NO 68
<211> LENGTH: 108
<212> TYPE: PRT
<213> ORGANISM: Mus Musculus
```

-continued

<400> SEQUENCE: 68

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Tyr Thr Phe Gly Gly Gly Thr Lys Leu Glu Ile Lys
            100                 105

<210> SEQ ID NO 69
<211> LENGTH: 5
<212> TYPE: PRT
<213> ORGANISM: Mus Musculus

<400> SEQUENCE: 69

Ser Ser Trp Met Asn
1               5

<210> SEQ ID NO 70
<211> LENGTH: 17
<212> TYPE: PRT
<213> ORGANISM: Mus Musculus

<400> SEQUENCE: 70

Arg Ile Tyr Pro Gly Asp Gly Asp Thr Lys Tyr Asn Gly Lys Phe Lys
1               5                   10                  15

Gly

<210> SEQ ID NO 71
<211> LENGTH: 11
<212> TYPE: PRT
<213> ORGANISM: Mus Musculus

<400> SEQUENCE: 71

Ser Thr Met Ile Ala Thr Gly Ala Met Asp Tyr
1               5                   10

<210> SEQ ID NO 72
<211> LENGTH: 11
<212> TYPE: PRT
<213> ORGANISM: Mus Musculus

<400> SEQUENCE: 72

Lys Ala Ser Gln Asp Val Ser Thr Ala Val Ala
1               5                   10

<210> SEQ ID NO 73
<211> LENGTH: 7
<212> TYPE: PRT
<213> ORGANISM: Mus Musculus

<400> SEQUENCE: 73

Ser Ala Ser Tyr Arg Tyr Thr
1               5

```
<210> SEQ ID NO 74
<211> LENGTH: 10
<212> TYPE: PRT
<213> ORGANISM: Mus Musculus

<400> SEQUENCE: 74

Gln Gln His Tyr Ser Thr Pro Pro Tyr Thr
1               5                   10

<210> SEQ ID NO 75
<211> LENGTH: 227
<212> TYPE: PRT
<213> ORGANISM: Macaca fascicularis

<400> SEQUENCE: 75

Met Ala Gly Ser Pro Thr Cys Phe Thr Phe Ile Tyr Ile Leu Trp Gln
1               5                   10                  15

Leu Thr Gly Ser Thr Ala Ser Gly Ser Val Lys Glu Leu Val Gly Ser
                20                  25                  30

Ile Gly Gly Ala Val Thr Phe Pro Leu Lys Ser Glu Val Lys Gln Val
            35                  40                  45

Asp Ser Ile Val Trp Thr Phe Asn Thr Thr Leu Val Thr Ile Gln
    50                  55                  60

Pro Glu Gly Gly Pro Met Ile Val Thr Gln Asn Arg Asn Lys Glu Arg
65              70                  75                  80

Val His Phe Pro Asp Gly Gly Tyr Ser Leu Lys Leu Ser Lys Leu Lys
                85                  90                  95

Lys Asn Asp Ser Gly Ile Tyr Asn Val Glu Ile Tyr Ser Ser Leu
            100                 105                 110

Gln Asp Pro Phe Thr Arg Lys Tyr Val Leu Arg Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Val Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Thr Val Arg Asn Pro Val Ser Ser Asn Ser Ser Ser Pro
        195                 200                 205

Ile Leu Ala Arg Lys Leu Cys Glu Gly Ala Ala Asp Asp Ser Asp Ser
    210                 215                 220

Ser Met Val
225

<210> SEQ ID NO 76
<211> LENGTH: 227
<212> TYPE: PRT
<213> ORGANISM: Macaca mulatta

<400> SEQUENCE: 76

Met Ala Gly Ser Pro Thr Cys Leu Thr Phe Ile Tyr Ile Leu Trp Gln
1               5                   10                  15

Leu Thr Gly Ser Thr Ala Ser Gly Ser Val Lys Glu Leu Val Gly Ser
                20                  25                  30

Ile Gly Gly Ala Val Thr Phe Pro Leu Lys Ser Glu Val Lys Gln Val
            35                  40                  45
```

```
Asp Ser Ile Val Trp Thr Phe Asn Thr Thr Leu Val Thr Ile Gln
     50                   55                   60

Pro Glu Gly Gly Pro Met Ile Val Thr Gln Asn Arg Asn Lys Glu Arg
 65                   70                   75                   80

Val His Phe Pro Asp Gly Gly Tyr Ser Leu Lys Leu Ser Lys Leu Lys
                     85                   90                   95

Lys Asn Asp Ser Gly Ile Tyr Asn Val Glu Ile Tyr Ser Ser Ser Leu
                100                  105                  110

Gln Asp Pro Phe Thr Arg Lys Tyr Val Leu Arg Val Tyr Glu His Leu
                115                  120                  125

Ser Lys Pro Lys Val Thr Met Gly Leu Gln Ser Asn Lys Asn Gly Thr
130                  135                  140

Cys Val Thr Asn Leu Thr Cys His Met Glu His Gly Glu Glu Asp Val
145                  150                  155                  160

Ile Tyr Thr Trp Lys Ala Leu Gly Gln Ala Val Asn Glu Ser His Asn
                165                  170                  175

Gly Ser Ile Leu Pro Ile Ser Trp Arg Trp Gly Glu Ser Asp Met Thr
                180                  185                  190

Phe Ile Cys Thr Val Arg Asn Pro Val Ser Ser Asn Ser Ser Ser Pro
                195                  200                  205

Ile Leu Ala Arg Lys Leu Cys Glu Gly Ala Ala Asp Asp Ser Asp Ser
210                  215                  220

Ser Met Val
225

<210> SEQ ID NO 77
<211> LENGTH: 227
<212> TYPE: PRT
<213> ORGANISM: Homo sapiens

<400> SEQUENCE: 77

Met Ala Gly Ser Pro Thr Cys Leu Thr Leu Ile Tyr Ile Leu Trp Gln
  1               5                   10                  15

Leu Thr Gly Ser Ala Ala Ser Gly Pro Val Lys Glu Leu Val Gly Ser
                 20                  25                  30

Val Gly Gly Ala Val Thr Phe Pro Leu Lys Ser Lys Val Lys Gln Val
                 35                  40                  45

Asp Ser Ile Val Trp Thr Phe Asn Thr Thr Pro Leu Val Thr Ile Gln
     50                  55                   60

Pro Glu Gly Gly Thr Ile Ile Val Thr Gln Asn Arg Asn Arg Glu Arg
 65                   70                   75                   80

Val Asp Phe Pro Asp Gly Gly Tyr Ser Leu Lys Leu Ser Lys Leu Lys
                     85                   90                   95

Lys Asn Asp Ser Gly Ile Tyr Tyr Val Gly Ile Tyr Ser Ser Ser Leu
                100                  105                  110

Gln Gln Pro Ser Thr Gln Glu Tyr Val Leu His Val Tyr Glu His Leu
                115                  120                  125

Ser Lys Pro Lys Val Thr Met Gly Leu Gln Ser Asn Lys Asn Gly Thr
130                  135                  140

Cys Val Thr Asn Leu Thr Cys Cys Met Glu His Gly Glu Glu Asp Val
145                  150                  155                  160

Ile Tyr Thr Trp Lys Ala Leu Gly Gln Ala Ala Asn Glu Ser His Asn
                165                  170                  175

Gly Ser Ile Leu Pro Ile Ser Trp Arg Trp Gly Glu Ser Asp Met Thr
                180                  185                  190
```

```
Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val
225

<210> SEQ ID NO 78
<211> LENGTH: 227
<212> TYPE: PRT
<213> ORGANISM: Pan troglodytes

<400> SEQUENCE: 78

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Arg Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Pro Leu Val Thr Ile Gln
    50                  55                  60

Pro Glu Gly Gly Thr Ile Ile Val Thr Gln Asn Arg Asn Lys Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Lys Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Ser Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val
225

<210> SEQ ID NO 79
<211> LENGTH: 224
<212> TYPE: PRT
<213> ORGANISM: Artificial
<220> FEATURE:
<223> OTHER INFORMATION: hu25/mu75: amino acids 1-67 of human CS1 fused
      to amino acids 68-224 of mouse CS1

<400> SEQUENCE: 79

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30
```

```
Val Gly Gly Ala Val Thr Phe Pro Leu Lys Ser Lys Val Lys Gln Val
         35                  40                  45

Asp Ser Ile Val Trp Thr Phe Asn Thr Thr Pro Leu Val Thr Ile Gln
 50                  55                  60

Pro Glu Gly Val Thr Ser Gln Ser Ser Asn Lys Glu Arg Ile Val Phe
 65                  70                  75                  80

Pro Asp Gly Leu Tyr Ser Met Lys Leu Ser Gln Leu Lys Lys Asn Asp
             85                  90                  95

Ser Gly Ala Tyr Arg Ala Glu Ile Tyr Ser Thr Ser Ser Gln Ala Ser
            100                 105                 110

Leu Ile Gln Glu Tyr Val Leu His Val Tyr Lys His Leu Ser Arg Pro
        115                 120                 125

Lys Val Thr Ile Asp Arg Gln Ser Asn Lys Asn Gly Thr Cys Val Ile
    130                 135                 140

Asn Leu Thr Cys Ser Thr Asp Gln Asp Gly Glu Asn Val Thr Tyr Ser
145                 150                 155                 160

Trp Lys Ala Val Gly Gln Gly Asp Asn Gln Phe His Asp Gly Ala Thr
                165                 170                 175

Leu Ser Ile Ala Trp Arg Ser Gly Glu Lys Asp Gln Ala Leu Thr Cys
            180                 185                 190

Met Ala Arg Asn Pro Val Ser Asn Ser Phe Ser Thr Pro Val Phe Pro
        195                 200                 205

Gln Lys Leu Cys Glu Asp Ala Ala Thr Asp Leu Thr Ser Leu Arg Gly
    210                 215                 220

<210> SEQ ID NO 80
<211> LENGTH: 227
<212> TYPE: PRT
<213> ORGANISM: Artificial
<220> FEATURE:
<223> OTHER INFORMATION: mu25/hu75: amino acids 1-67 of mouse CS1 fused
      to amino acids 68-227 of human CS1

<400> SEQUENCE: 80

Met Ala Arg Phe Ser Thr Tyr Ile Ile Phe Thr Ser Val Leu Cys Gln
 1               5                  10                  15

Leu Thr Val Thr Ala Ala Ser Gly Thr Leu Lys Lys Val Ala Gly Ala
             20                  25                  30

Leu Asp Gly Ser Val Thr Phe Thr Leu Asn Ile Thr Glu Ile Lys Val
         35                  40                  45

Asp Tyr Val Val Trp Thr Phe Asn Thr Phe Pro Leu Ala Met Val Lys
 50                  55                  60

Lys Asp Gly Gly Thr Ile Ile Val Thr Gln Asn Arg Asn Arg Glu Arg
 65                  70                  75                  80

Val Asp Phe Pro Asp Gly Gly Tyr Ser Leu Lys Leu Ser Lys Leu Lys
             85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175
```

```
Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val
225

<210> SEQ ID NO 81
<211> LENGTH: 227
<212> TYPE: PRT
<213> ORGANISM: Artificial
<220> FEATURE:
<223> OTHER INFORMATION: hu50/mu50: amino acids 1-151 of human CS1 fused
      to amino acids 149-224 of mouse CS1

<400> SEQUENCE: 81

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Ile Asp Arg Gln Ser Asn Lys Asn Gly Thr
    130                 135                 140

Cys Val Ile Asn Leu Thr Cys Ser Thr Asp Gln Asp Gly Glu Asn Val
145                 150                 155                 160

Thr Tyr Ser Trp Lys Ala Val Gly Gln Gly Asp Asn Gln Phe His Asp
                165                 170                 175

Gly Ala Thr Leu Ser Ile Ala Trp Arg Ser Gly Glu Lys Asp Gln Ala
            180                 185                 190

Leu Thr Cys Met Ala Arg Asn Pro Val Ser Asn Ser Phe Ser Thr Pro
        195                 200                 205

Val Phe Pro Gln Lys Leu Cys Glu Asp Ala Ala Thr Asp Leu Thr Ser
    210                 215                 220

Leu Arg Gly
225

<210> SEQ ID NO 82
<211> LENGTH: 224
<212> TYPE: PRT
<213> ORGANISM: Artificial
<220> FEATURE:
<223> OTHER INFORMATION: mu50/hu50: amino acids 1-131 of mouse CS1 fused
      to amino acids 135-227 of human CS1
```

<400> SEQUENCE: 82

```
Met Ala Arg Phe Ser Thr Tyr Ile Ile Phe Thr Ser Val Leu Cys Gln
1               5                   10                  15

Leu Thr Val Thr Ala Ala Ser Gly Thr Leu Lys Lys Val Ala Gly Ala
            20                  25                  30

Leu Asp Gly Ser Val Thr Phe Thr Leu Asn Ile Thr Glu Ile Lys Val
        35                  40                  45

Asp Tyr Val Val Trp Thr Phe Asn Thr Phe Phe Leu Ala Met Val Lys
    50                  55                  60

Lys Asp Gly Val Thr Ser Gln Ser Ser Asn Lys Glu Arg Ile Val Phe
65                  70                  75                  80

Pro Asp Gly Leu Tyr Ser Met Lys Leu Ser Gln Leu Lys Lys Asn Asp
                85                  90                  95

Ser Gly Ala Tyr Arg Ala Glu Ile Tyr Ser Thr Ser Ser Gln Ala Ser
            100                 105                 110

Leu Ile Gln Glu Tyr Val Leu His Val Tyr Lys His Leu Ser Arg Pro
        115                 120                 125

Lys Val Thr Met Gly Leu Gln Ser Asn Lys Asn Gly Thr Cys Val Thr
130                 135                 140

Asn Leu Thr Cys Cys Met Glu His Gly Glu Glu Asp Val Ile Tyr Thr
145                 150                 155                 160

Trp Lys Ala Leu Gly Gln Ala Ala Asn Glu Ser His Asn Gly Ser Ile
                165                 170                 175

Leu Pro Ile Ser Trp Arg Trp Gly Glu Ser Asp Met Thr Phe Ile Cys
            180                 185                 190

Val Ala Arg Asn Pro Val Ser Arg Asn Phe Ser Ser Pro Ile Leu Ala
        195                 200                 205

Arg Lys Leu Cys Glu Gly Ala Ala Asp Asp Pro Asp Ser Ser Met Val
    210                 215                 220
```

<210> SEQ ID NO 83
<211> LENGTH: 227
<212> TYPE: PRT
<213> ORGANISM: Artificial
<220> FEATURE:
<223> OTHER INFORMATION: hu75/mu25: amino acids 1-169 of human CS1 fused
      to amino acids 167-224 of mouse CS1

<400> SEQUENCE: 83

```
Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125
```

```
Ser Lys Pro Lys Val Thr Met Gly Leu Gln Ser Asn Lys Asn Gly Thr
        130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Gly Asp Asn Gln Phe His Asp
                165                 170                 175

Gly Ala Thr Leu Ser Ile Ala Trp Arg Ser Gly Glu Lys Asp Gln Ala
            180                 185                 190

Leu Thr Cys Met Ala Arg Asn Pro Val Ser Asn Ser Phe Ser Thr Pro
        195                 200                 205

Val Phe Pro Gln Lys Leu Cys Glu Asp Ala Ala Thr Asp Leu Thr Ser
    210                 215                 220

Leu Arg Gly
225

<210> SEQ ID NO 84
<211> LENGTH: 224
<212> TYPE: PRT
<213> ORGANISM: Artificial
<220> FEATURE:
<223> OTHER INFORMATION: mu75/hu25: amino acids 1-166 of mouse CS1 fused
      to amino acids 170-227 of human CS1

<400> SEQUENCE: 84

Met Ala Arg Phe Ser Thr Tyr Ile Ile Phe Thr Ser Val Leu Cys Gln
1               5                   10                  15

Leu Thr Val Thr Ala Ala Ser Gly Thr Leu Lys Lys Val Ala Gly Ala
            20                  25                  30

Leu Asp Gly Ser Val Thr Phe Thr Leu Asn Ile Thr Glu Ile Lys Val
        35                  40                  45

Asp Tyr Val Val Trp Thr Phe Asn Thr Phe Phe Leu Ala Met Val Lys
    50                  55                  60

Lys Asp Gly Val Thr Ser Gln Ser Ser Asn Lys Glu Arg Ile Val Phe
65                  70                  75                  80

Pro Asp Gly Leu Tyr Ser Met Lys Leu Ser Gln Leu Lys Lys Asn Asp
                85                  90                  95

Ser Gly Ala Tyr Arg Ala Glu Ile Tyr Ser Thr Ser Ser Gln Ala Ser
            100                 105                 110

Leu Ile Gln Glu Tyr Val Leu His Val Tyr Lys His Leu Ser Arg Pro
        115                 120                 125

Lys Val Thr Ile Asp Arg Gln Ser Asn Lys Asn Gly Thr Cys Val Ile
    130                 135                 140

Asn Leu Thr Cys Ser Thr Asp Gln Asp Gly Glu Asn Val Thr Tyr Ser
145                 150                 155                 160

Trp Lys Ala Val Gly Gln Ala Ala Asn Glu Ser His Asn Gly Ser Ile
                165                 170                 175

Leu Pro Ile Ser Trp Arg Trp Gly Glu Ser Asp Met Thr Phe Ile Cys
            180                 185                 190

Val Ala Arg Asn Pro Val Ser Arg Asn Phe Ser Ser Pro Ile Leu Ala
        195                 200                 205

Arg Lys Leu Cys Glu Gly Ala Ala Asp Asp Pro Asp Ser Ser Met Val
    210                 215                 220

<210> SEQ ID NO 85
<211> LENGTH: 20
<212> TYPE: DNA
<213> ORGANISM: Artificial
```

-continued

```
<220> FEATURE:
<223> OTHER INFORMATION: VH PCR 3' prime primer

<400> SEQUENCE: 85
agctgggaag gtgtgcacac                                               20

<210> SEQ ID NO 86
<211> LENGTH: 20
<212> TYPE: DNA
<213> ORGANISM: Artificial
<220> FEATURE:
<223> OTHER INFORMATION: VL PCR 3' prime primer

<400> SEQUENCE: 86
ttcactgcca tcaatcttcc                                               20

<210> SEQ ID NO 87
<211> LENGTH: 17
<212> TYPE: PRT
<213> ORGANISM: Homo Sapiens

<400> SEQUENCE: 87

Glu Ile Asn Pro Asp Ser Ser Thr Ile Asn Tyr Ala Pro Ser Leu Lys
1               5                   10                  15

Asp
```

THERAPEUTIC USE OF ANTI-CS1 ANTIBODIES

This application is a continuation of U.S. patent application Ser. No. 12/397,026, filed Mar. 3, 2009, now U.S. Pat. No. 8,088,898 which is a continuation of U.S. patent application Ser. No. 10/982,357, filed Nov. 5, 2004, now U.S. Pat. No. 7,709,610, which is a continuation in part of U.S. patent application Ser. No. 10/842,011, filed May 7, 2004, now abandoned, and claims the benefit of priority of U.S. Provisional Application 60/469,211, filed May 8, 2003, U.S. Provisional Application 60/557,620, filed Mar. 29, 2004, U.S. Provisional Application 60/557,622, filed Mar. 29, 2004, and U.S. Provisional Application 60/557,621, filed Mar. 29, 2004, each of which is specifically incorporated herein by reference in its entirety.

FIELD OF THE INVENTION

The invention relates to the field of antagonists and antibodies in the treatment of diseases, including diseases related to autoimmune and cancer. The invention further relates to methods for detecting, identifying and modulating these diseases.

BACKGROUND OF THE INVENTION

Increased expression of immunoglobulin is a characteristic of many diseases. High level secretion of immunoglobulin causes a variety of disorders, including hypervisocity syndrome, a debilitating disorder resulting in fatigue, headaches, shortness of breath, mental confusion, chest pain, kidney damage and failure, vision problems and Raynaud's phenomenon (poor blood circulation, particularly fingers, toes, nose and ears). Cold agglutinin disease, mixed cryoglobulinemia, hypergammaglobulinemia, Sjogren's syndrome, Lichen myxedematosus, and Gaucher's disease are examples of diseases associated with increased expression of immunoglobulins.

Increased expression of immunoglobulin targeted to self-proteins is a hallmark of autoimmune diseases. Autoimmune disease is a failure of the immune system to recognize auto-antigens as self. In autoimmune diseases, the immune system mistakenly attacks itself, targeting cells, tissues and organs, eventually resulting in the destruction of physiological systems. Autoimmunity and autoimmune diseases are multifactorial in origin, with genetic predisposition, host factors (e.g., weakness of immunoregulatory controls, defects in suppressor T cells, or polyclonal stimulation of B cells resistant to controls), environmental factors and antigen-driven mechanisms being implicated in the development of autoimmunity and production of self-antibodies to self-antigens.

Gastrointestinal disorders and Systemic Lupus Erythrematosus (SLE) are two examples of autoimmune diseases. Inflammatory bowel disease (IBD), a subgroup of gastrointestinal disorders, is a group of incurable disorders that affect approximately 4 million individuals worldwide. The etiology of recurrent inflammatory bowel disease is currently unknown. Theories include an autoimmune-mediated destruction of gastrointestinal cells, including lymphocytes. Abnormal homotypic aggregation in heritable inflammatory bowel disease models has been demonstrated previously, and mutations in NOD2, a gene implicated in autoimmune disorders, have been shown to predispose patients to Crohn's disease. Ni, J. et al., *Immunological abnormality in C3H/HeJ mice with heritable inflammatory bowel disease*, Cell Immunol. 169:7-15 (1996); Ogura, Y. et al., *A frameshift mutation in NOD2 associated with susceptibility to Crohn's Disease*, Nature 411: 603-606 (2001).

IBDs most often affect the small intestine and colon, but may involve any portion of the gastrointestinal tract. There are over 1 million people diagnosed with IBD in the United States alone, with over 10,000 new cases diagnosed annually. Because of the drastic effect in the quality of life for IBD patients, tens of thousands of lost hours are claimed annually, equaling up to 1 billion dollars in missed work days a year.

IBD produces a range of gastrointestinal and extraintestinal symptoms, including diarrhea, rectal bleeding, abdominal pain, weight loss, skin and eye disorders, and delayed growth and sexual maturation in children. Two types of IBD are ulcerative colitis and Crohn's disease, which share similar symptoms and physiological manifestations, but differ in the manner in which they affect the digestive tract. Ulcerative colitis is characterized by ulcerative inflammation of all or part of the colonic mucosa, most frequently including the rectum. Its symptoms include rectal bleeding and urgency, tenesmus, and diarrhea. Ulcerative colitis is accompanied by serious short- and long-term complications. The most serious short-term complications are fulminant colitis, toxic megacolon, and perforation. Severe long-term complications include osteoporosis and colorectal cancer.

Crohn's disease is a chronic transmural inflammation that may affect any part of the gastrointestinal tract, from the mouth to the anus. Crohn's disease is discontinuous, with unaffected areas interspersed between one or more involved areas. Late in the disease, the mucosa develops a cobblestone appearance, which results from deep longitudinal ulcerations interlaced with intervening normal mucosa.

Most Crohn's disease patients present with symptoms of abdominal pain and tenderness, chronic or nocturnal diarrhea, rectal bleeding, weight loss, and fever. Crohn's disease evolves over time from a primarily inflammatory disease into one of two clinical patterns: stricturing (obstructive) or penetrating (fistulizing). In the stricturing form, transmural inflammation produces fibromuscular proliferation in the intestinal wall, followed by luminal narrowing. Symptoms of obstruction become common as CD progresses. In the penetrating form, sinus tracts form as inflammation tunnels through the bowel wall and breaches the serosal surface, fistulizing into adjoining tissues and even through the skin.

Ulcerative colitis and Crohn's disease are generally diagnosed using clinical, endoscopic, and histologic criteria. However, so far the traditional diagnostic techniques have established that no single finding is absolutely diagnostic for one disease or the other. Furthermore, approximately 20% of patients have a clinical picture that falls between Crohn's disease and ulcerative colitis. Patients that fit this profile are said to have indeterminate colitis.

IBD symptoms can greatly impact a patient's well-being, quality of life, and capacity to function. Inflammatory periods are protracted and frequent, and depending on the severity, life crippling. Because IBD is chronic and typically has an onset before 30 years of age, patients generally require life-long treatment. The elucidation of a role for novel proteins and compounds in disease states for identification of potential targets and diagnostic markers is valuable for improving the current treatment of inflammatory bowel disease patients.

SLE is characterized by the production of auto-antibodies to a variety of ubiquitous molecules, which can have pathogenic consequences including damage to numerous organs and tissues, including skin, kidney, brain, and heart. The current approved treatments for SLE involve non-specific immunosuppression and symptom control through steroids, immunosuppressive drugs, immunomodulators, and anti-malarial drugs. However, these treatment approaches result in risks of renal toxicity and early mortality. Thus, it is desirable to develop a new approach that specifically interferes with lymphocyte activation and auto-antibody production.

Other autoimmune diseases in which increased expression of immunoglobulin and/or B cells play a significant role include idiopathic thrombocytopenia, rheumatoid arthritis (RA), autoimmune hemolytic anemia, and Myasthenia gravis. Evidence for the role of B cells and/or increased immunoglobulin comes from studies with patients treated with steroids, immunosuppressive agents, and/or anti-CD20 antibodies (which target B cells). Improvement in symptoms in these diseases correlates with a decrease in B cells and/or serum immunoglobulin, underscoring the pivotal role that B cells play in a variety of autoimmune diseases.

Increased expression of immunoglobulin can also be seen in malignant diseases. Like autoimmune disorders, the etiology of cancer is similarly multi-factorial in origin. Cancer, which is the second leading cause of death in the United States, has been linked to mutations in DNA that cause unrestrained growth of cells. Genetic predisposition plays a large role in the development of many cancers, combined with environmental factors, such as smoking and chemical mutagenesis.

Cancer can occur in any tissue or organ of the body. Plasma cell neoplasms, including multiple myeloma, "Solitary" myeloma of bone, extramedullary plasmacytoma, plasma cell leukemia, macroglobulinemia (including Waldenstrom's macroglobulinemia), heavy-chain disease, primary amyloidosis, monoclonal gammopathy of unknown significance (MGUS) are associated with increased expression of immunoglobulins. Chronic lymphocytic leukemia (CLL), a non-plasma cell neoplasm, is also associated with high levels of immunoglobulin expression.

Myelomas are tumors of plasma cells derived from a single clone, which typically originates in secondary lymphoid tissue and then migrates into and resides in bone marrow tissue. Myelomas commonly affect the bone marrow and adjacent bone structures, with primary symptoms of bone pain and pathological fractures or lesions (osteolytic bone lesions), abnormal bleeding, anemia and increased susceptibility to infections. Advanced stages of the disease include renal failure, skeletal deformities, compaction of the spinal cord, and hypercalcemia. Myeloma affects bone cells by inducing osteoclast resorption of bone, hence decimating bone structure and increasing calcium concentration in plasma. The etiology of myelomas is currently unknown. Linkage to radiation damage, mutations in oncogenes, familial causes and abnormal IL6 expression have been postulated.

Multiple myelomas are plasma cell tumors with multiple origins. Multiple myelomas account for nearly 10% of all plasma cell malignancies, and are the most common bone tumor cancer in adults, with an annual incident rate of 3 to 4 cases per 100,000 people. In the United States, multiple myelomas are the second most common hematologic malignancy after Non-Hodgkin's Lymphoma, with approximately 50,000 cases in the United States alone, and approximately 13,500 new reported cases every year. The prognosis outlook for patients diagnosed with multiple myelomas is grim, with only several months to a year for patients with advanced forms of the disease.

Traditional treatment regions for myeloma and multiple myelomas (henceforth referred to as "myeloma") consist of chemotherapy, radiation therapy, and surgery. In addition, bone marrow transplantation is recommended for patients who are otherwise in good health. The cure rate for patients approaches 30%, and is the only method known that can cure myelomas. However, for individuals who are older or cannot tolerate bone marrow transplantation procedures, chemotherapy is most appropriate.

Current diagnostic procedures include X rays, bone marrow aspiration, blood and urine tests (to detect the presence of the Bence Jones protein), and the erythrocyte sedimentation rate assay. Potential cell surface markers in myelomatous plasma cells have also been identified, including CD38, CD9, CD10, HLA-DR, and CD20. Ruiz-Arugelles G J and San Miguel J F, Cell Surface Markers in Multiple Myeloma, Mayo Clin. Proc. 69:684-90 (1994). Other non-B-cell lineage markers include CD2, CD4, CD13, CD14, CD15, CD23, CD 24, CD25, CD33, CD39, CDw40, CD41, CD45R, CD54, CD56 and CD71, as well as unclustered antigens, R1-3, PCA-1, PCA-2, PC1, 62B1, 8A, 8F6 and MM4). Ruiz-Arugelles, supra; Leo R, et al., *Multiparameter analysis of normal and malignant human plasma cells*, Ann. Hematol. 64:132-9 (1992). In addition, appearance of abnormal antibodies, known as M-protein, is an indicator of multiple myeloma. The increased production of M-protein has been linked to hyperviscosity syndrome in multiple myelomas, causing debilitating side effects, including fatigue, headaches, shortness of breath, mental confusion, chest pain, kidney damage and failure, vision problems and Raynaud's phenomenon (poor blood circulation, particularly fingers, toes, nose and ears). Cryoglobulinemia occurs when M-protein in the blood forms particles under cold conditions. These particles can block small blood vessels and cause pain and numbness in the toes, fingers, and other extremities during cold weather. Prognostic indicators, such as chromosomal deletions, elevated levels of beta-2 microglobulin, serum creatinine levels and IgA isotyping have also been studied. Tricot G, et al., *Poor prognosis in Multiple Myeloma*, Blood 86:4250-2 (1995).

CS1 (SLAMF7, 19A; Genbank Accession Number NM_021181.3, Ref. Boles and Mathew (2001) Immunogenetics 52:302-307; Bouchon et al., (2001) J. Immunol. 167: 5517-5521; Murphy et al., (2002) Biochem. J. 361:431-436) is a member of the CD2 subset of the immunoglobulin superfamily. Molecules of the CD2 family are involved in a broad range of immunomodulatory functions, such as co-activation, proliferation differentiation, and adhesion of lymphocytes, as well as immunoglobulin secretion, cytokine production, and NK cell cytotoxicity. Several members of the CD2 family, such as CD2, CD58, and CD150, play a role or have been proposed to play a role in a number of autoimmune and inflammatory diseases, such as psoriasis, rheumatoid arthritis, and multiple sclerosis.

CS1 (also known as CRACC, 19A, APEX-1, and FOAP12) was isolated and cloned by Boles, K. et al. (see Immunogenetics 52: 302-307 (2001)). It has been reported that CS1 plays a role in NK cell-mediated cytotoxicity and lymphocyte adhesion (Bouchon, A., et al., J. of Immuno. 5517-5521 (2001); Murphy, J. et al., Biochem. J. 361: 431-436 (2002)).

PCT Application PCT/US00/34963 discloses a monoclonal antibody against APEX-1 and the use thereof for detecting the produced recombinant extracellular domain of APEX-1. U.S. patent application 2003/0113332A1 discloses monoclonal antibodies against the peptides of natural killer cell surface receptors that bind to CS1 and lead to NK cell activation. These applications are herein incorporated for reference in its entirety. However, antibodies capable of inhibiting immunoglobulin production by B cells and/or proliferation and/or development of myelomas have not been developed and disclosed in the above-referenced publications. Also, evidence of over-expression of CS-1 in autoimmune disease or cancer has not been developed or disclosed in the above-referenced publications.

The elucidation of a role for novel proteins and compounds in disease states for identification of potential targets and diagnostic markers is desirable for improving the current treatment of autoimmune and cancer patients, including patients afflicted with IBD, SLE, RA and myeloma. Accordingly, provided herein are molecular targets for treatment and diagnosis of these diseases, particularly CS1. Additionally, provided herein are antagonists that bind to and neutralize CS1, including neutralizing antibodies such as anti-CS1 antibodies.

SUMMARY OF THE INVENTION

The present invention provides an antibody or an antigen binding fragment that binds to a human CS1 epitope recognized by Luc 90. Luc 90 and other antibodies that share the same epitope, including Luc 34, Luc 69 and Luc X, are capable of inhibiting immunoglobulin secretion and killing of CS1 expressing cells.

The present invention also provides an antibody or an antigen binding fragment that binds to a human CS1 epitope recognized by Luc 63. Luc 63 and other antibodies that share the same epitope, including Luc 4, Luc 12, Luc 23, Luc 29, Luc 32 and Luc 37, are capable of inhibiting immunoglobulin secretion and killing of CS1 expressing cells.

The present invention further provides an antibody or an antigen binding fragment that triggers cytotoxic effects on cells expressing CS1 or enhances cytotoxicity mediated by immune cells, including ADCC-mediated cytotoxicity of cells expressing CS1.

The present invention further provides a method for killing CS1 expressing cells comprising contacting the cells with an effective amount of anti-CS1 antibody. The CS1 expressing cells include plasma cell cancer cells from, e.g., multiple myeloma, and non-plasma cancer cells from, e.g., chronic lymphocytic leukemia. The CS1 expressing cells further include leukocytes such as activated B cells or T cells, and leukocytes from patients suffering from SLE and rheumatoid arthritis.

The present invention further provides a method for treating an individual suffering from plasma cell cancers, SLE, rheumatoid arthritis or inflammatory bowel disease.

BRIEF DESCRIPTION OF THE DRAWINGS

Figures

DETAILED DESCRIPTION OF THE INVENTION

Figure 1A:
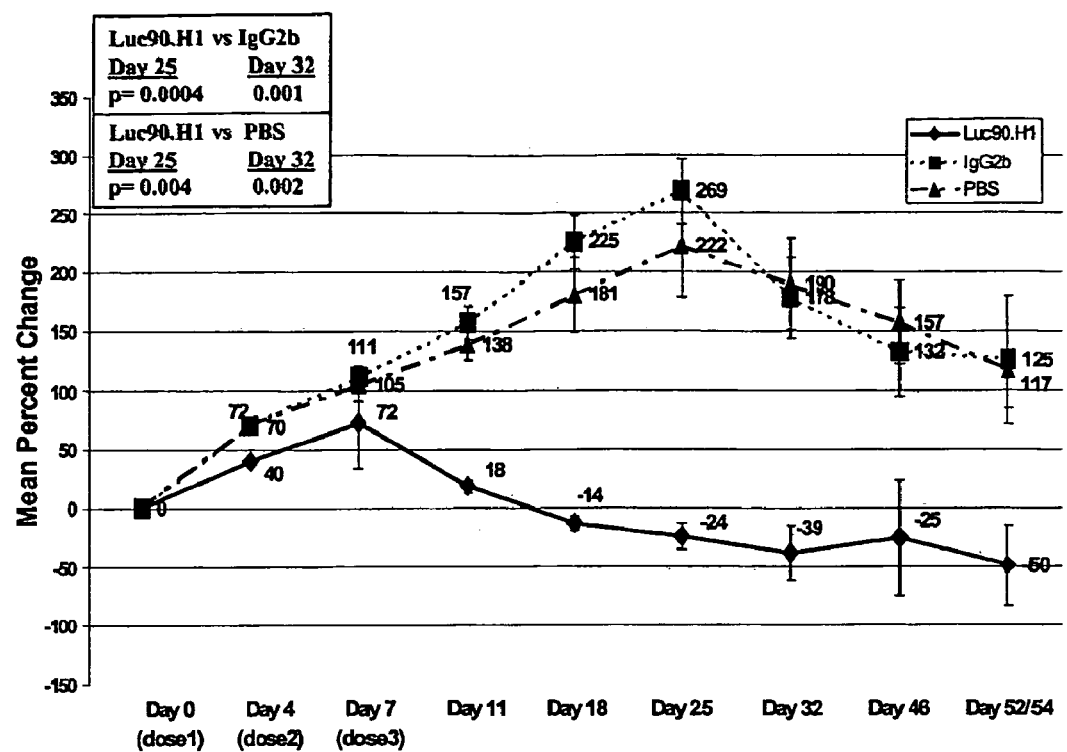
FIG. 1A shows the inhibition of in vivo human IgG production in SCID-HuPBMC mouse model by anti-CS1 monoclonal antibodies.

The present invention is based in part on our discovery that there is no significant CS1 protein expression detected on platelets, red blood cells, endothelial cells (HuVECs), kidney cells, bronchial airway cells, small airway cells, prostate cells, liver cells or breast cells. CS1 expression is lymphoid specific, and is detected on cells from patients, including plasma cells from multiple myeloma and plasma cell leukemia patients. Expression is detected only on plasma cells and not detectable at significant levels on other cell types from bone marrow samples. Accordingly, the present invention has demonstrated the feasibility of using anti-CS1 antibodies as therapeutic agents for the treatment of cancer, including but not limited to plasma cell neoplasms, including myeloma, multiple myeloma, "solitary" myeloma of bone, extramedullary plasmacytoma, plasma cell leukemia, macroglobulinemia (including Waldenstrom's macroglobulinemia), heavy-chain disease, primary amyloidosis, monoclonal gammopathy of unknown significance (MGUS). In addition, non-plasma cell neoplasms associated with increased expression of immunoglobulin, including chronic lymphocytic leukemia (CLL), will also benefit from anti-CS1 therapy.

In addition, previous studies have not revealed the expression of CS1 protein on in vitro PWM (pokeweed mitogen)-activated peripheral blood B cells, subsets of memory/effector versus naïve peripheral blood B and T lymphocytes, or $CD14^+$ monocytes/macrophages from peripheral blood. Previous studies have also not revealed the role of CS1 in immunoglobulin production. As a result, the correlation between CS1 and autoimmune diseases has not been previously established. The present invention is also based in part on our discovery that the CS1 RNA and protein expression are strongly up-regulated in activated peripheral blood B cells, the cell subset responsible for auto-antibody production and believed to play a significant role in the development of autoimmune diseases. Furthermore, the present invention has revealed that expression of the CS1 RNA in SLE patient peripheral blood B lymphocytes is increased in comparison to B cells from age-matched healthy adults, as well as in patients afflicted with IBD. The present invention reveals that CS-1 is expressed on infiltrating plasma cells in rheumatoid arthritis (RA) synovium. The present invention has also revealed that CS1 is involved in antibody production and that antibodies to CS1 decrease IgM and IgG secreted by B cells from healthy adults and patients with lupus. Subsequently, the data of the present invention suggest that CS1 plays an important role in the establishment of autoimmune diseases, especially SLE, IBD, and RA. Other diseases associated with an increase in immunoglobulin, B cells, and/or B cell products would also benefit from anti-CS1 treatment, including cold agglutinin disease, immunobullous diseases (including bullous pemphigoid, pemphigus, dermatitis herpetiformis, linear IgA disease, and epidermolysis bullosa acquista), mixed cryoglobulinemia, hypergammaglobulinemia, Sjogren's syndrome, autoimmune anemia, asthma, myasthenia gravis, multiple sclerosis, myocardial or pericardial inflammation, atopic dermatitis, psoriasis, lichen myxedematosus, and Gaucher's disease.

Moreover, studies have not been conducted before to examine the feasibility of using anti-CS1 antibodies for treating autoimmune diseases and plasma cell cancers, including myeloma and plasma cell leukemia. An ideal therapeutic antibody should bind primarily to the target cells. Binding to other cells and tissues can cause potential damage to those cells and tissues and/or deplete the therapeutic antibody so that an excess amount of the antibody is required to be delivered to the patient in order to achieve the desired treatment efficacy. More importantly, an antibody that binds to platelets may have side effects, such as, platelet activation (which can lead to excessive clotting), or platelet depletion (which can lead to failure of blood clotting). Therefore, it is usually not feasible to use an antibody as a therapeutic agent if the antibody binds to multiple cells and tissues, especially if it binds to platelets. The present invention is based in part on our discovery that there is no significant CS1 protein expression detected on platelets, red blood cells, HuVECs, kidney cells, bronchial airway cells, small airway cells, prostate cells, liver cells and breast cells. Accordingly, the present invention has demonstrated the feasibility of using anti-CS1 antibodies as therapeutic agents for the treatment of autoimmune diseases, and plasma cell cancers, including myeloma and plasma cell leukemia.

The present invention, therefore, is directed to antagonists that bind to CS1. Exemplary embodiments of such embodiments include neutralizing anti-CS1 antibodies and antibody fragments. The antibodies neutralize at least one biological activity of CS1, wherein said antibodies bind to CS1 and are capable of at least one of the activities selected from the group consisting of: (a) inhibiting immunoglobulin secretion and/or production by lymphocytes; and (b) inducing lysis of cells that express CS1.

In accordance with the objects outlined above, the present invention provides novel methods for treatment of various disorders, e.g., autoimmune disorders and various defined cancerous conditions, including various forms of myeloma. Also provided are methods for the diagnosis and prognosis evaluation of such disorders, as well as methods for screening for compositions which modulate such conditions. The present invention also provides methods of monitoring the therapeutic efficacy of such treatment, including the monitoring and screening of markers selectively expressed in said disorders.

In particular, identification of markers selectively expressed in autoimmune disorders, such as SLE, RA, and IBD, and cancerous conditions, such as myeloma and plasma cell leukemia, allows for use of that expression in diagnostic, prognostic, or therapeutic methods. As such, the invention defines various compositions, e.g., nucleic acids, polypeptides, antibodies, and small molecule agonists/antagonists, which will be useful to selectively identify those markers. The markers may be useful for molecular characterization of subsets of the diseases, which subsets may actually require very different treatments. Moreover, the markers may also be important in diseases related to autoimmune disorders, myeloma, and plasma cell leukemia, e.g., which affect similar tissues as in such conditions, or have similar mechanisms of induction/maintenance. For example, tumor processes or characteristics may also be targeted. Diagnostic and prognostic uses are made available, e.g., to subset related but distinct diseases, to differentiate stages of autoimmune disorders myeloma, or plasma cell leukemia or to determine treatment strategy of such conditions. The detection methods may be based upon nucleic acid, e.g., PCR or hybridization techniques, or protein, e.g., ELISA, imaging, IHC, etc. The diagnosis may be qualitative or quantitative, and may detect increases or decreases in expression levels.

Definitions

The term "CS1 protein" or "CS1 polynucleotide" or "CS1-associated transcript" refers to nucleic acid and polypeptide polymorphic variants, alleles, mutants, and interspecies homologues that: (1) have a nucleotide sequence that has greater than about 60% nucleotide sequence identity, 65%, 70%, 75%, 80%, 85%, 90%, preferably about 92%, 94%, 96%, 97%, 98%, or 99% or greater nucleotide sequence identity, preferably over a region of over a region of at least about 25, 50, 100, 200, 500, 1000, or more nucleotides, to a nucleotide sequence of or associated with the CS1 gene (Table 2); binding of the CS1 gene (Table 2) to binding partners, e.g., polyclonal antibodies, raised against an immunogen comprising an amino acid sequence encoded by a nucleotide sequence of or associated with the CS1 gene (Table 2), and conservatively modified variants thereof; (3) specifically hybridize under stringent hybridization conditions to a nucleic acid sequence, or the complement thereof of CS1 (Table 2) and conservatively modified variants thereof; or (4) have an amino acid sequence that has greater than about 60% amino acid sequence identity, 65%, 70%, 75%, 80%, 85%, preferably 90%, 91%, 93%, 95%, 97%, 98%, or 99% or greater amino sequence identity, preferably over a region of over a region of at least about 25, 50, 100, 200, 500, 1000, or more amino acids, to an amino acid sequence encoded by a nucleotide sequence of or associated with the CS1 gene (Table 2). A polynucleotide or polypeptide sequence is typically from a mammal including, but not limited to, primate, e.g., human; rodent, e.g., rat, mouse, hamster; cow, pig, horse, sheep, or other mammal A "CS1 polypeptide" and a "CS1 polynucleotide," include both naturally occurring or recombinant forms.

TABLE 2

SEQ ID NO: 1

PDL primekey: 433671 DNA Sequence
Nucleic Acid Accession #: NM_021181
GI: 19923571 |ref| NM_021181.3| Homo sapiens SLAM family member 7
(SLAMF7), mRNA

```
   1 cttccagaga gcaatatggc tggttcccca acatgcctca ccctcatcta tatcctttgg 61 cagctcacag ggtcagcagc ctctggaccc gtgaaagagc tggtcggttc cgttggtggg 121 gccgtgactt tccccctgaa gtccaaagta aagcaagttg actctattgt ctggaccttc 181 aacacaaccc ctcttgtcac catacagcca gaaggggggca ctatcatagt gacccaaaat 241 cgtaataggg agagagtaga cttcccagat ggaggctact ccctgaagct cagcaaactg 301 aagaagaatg actcagggat ctactatgtg gggatataca gctcatcact ccagcagccc 361 tccacccagg agtacgtgct gcatgtctac gagcacctgt caaagcctaa agtcaccatg 421 ggtctgcaga gcaataagaa tggcacctgt gtgaccaatc tgacatgctg catggaacat 481 ggggaagagg atgtgattta tacctggaag gccctggggc aagcagccaa tgagtcccat 541 aatgggtcca tcctccccat ctcctggaga tggggagaaa gtgatatgac cttcatctgc 601 gttgccagga accctgtcag cagaaacttc tcaagcccca tccttgccag gaagctctgt 661 gaaggtgctg ctgatgaccc agattcctcc atggtcctcc tgtgtctcct gttggtgccc 721 ctcctgctca gtctctttgt actggggcta tttctttggt ttctgaagag agagagacaa
```

TABLE 2-continued

```
 781 gaagagtaca ttgaagagaa gaagagagtg gacatttgtc gggaaactcc taacatatgc
 841 ccccattctg gagagaacac agagtacgac acaatccctc acactaatag aacaatccta
 901 aaggaagatc cagcaaatac ggtttactcc actgtggaaa taccgaaaaa gatggaaaat
 961 ccccactcac tgctcacgat gccagacaca ccaaggctat tgcctatga aatgttatc
1021 tagacagcag tgcactcccc taagtctctg ctcaaaaaaa aaacaattct cggcccaaag
1081 aaaacaatca gaagaattca ctgatttgac tagaaacatc aaggaagaat gaagaacgtt
1141 gacttttttc caggataaat tatctctgat gcttctttag atttaagagt tcataattcc
1201 atccactgct gagaaatctc ctcaaaccca gaaggtttaa tcacttcatc ccaaaaatgg
1261 gattgtgaat gtcagcaaac cataaaaaaa gtgcttagaa gtattcctat agaaatgtaa
1321 atgcaaggtc acacatatta atgacagcct gttgtattaa tgatggctcc aggtcagtgt
1381 ctggagtttc attccatccc agggcttgga tgtaaggatt ataccaagag tcttgctacc
1441 aggagggcaa gaagaccaaa acagacagac aagtccagca gaagcagatg cacctgacaa
1501 aaatggatgt attaattggc tctataaact atgtgcccag cactatgctg agcttacact
1561 aattggtcag acgtgctgtc tgccctcatg aaattggctc caaatgaatg aactactttc
1621 atgagcagtt gtagcaggcc tgaccacaga ttcccagagg gccaggtgtg atccacagg
1681 acttgaaggt caaagttcac aaagatgaag aatcagggta gctgaccatg tttggcagat
1741 actataatgg agacacagaa gtgtgcatgg cccaaggaca aggacctcca gccaggcttc
1801 atttatgcac ttgtgctgca aaagaaaagt ctaggtttta aggctgtgcc agaacccatc
1861 ccaataaaga gaccgagtct gaagtcacat tgtaaatcta gtgtaggaga cttggagtca
1921 ggcagtgaga ctggtggggc acgggggggca gtgggtactt gtaaacccttt aaagatggtt
1981 aattcattca atagatattt attaagaacc tatgcggccc ggcatggtgg ctcacacctg
2041 taatcccagc actttgggag gccaaggtgg gtgggtcatc tgaggtcagg agttcaagac
2101 cagcctggcc aacatggtga aaccccatct ctactaaaga tacaaaaatt tgctgagcgt
2161 ggtggtgtgc acctgtaatc ccagctactc gagaggccaa ggcatgagaa tcgcttgaac
2221 ctgggaggtg gaggttgcag tgagctgaga tggcaccact gcactccggc ctaggcaacg
2281 agagcaaaac tccaatacaa acaaacaaac aaacacctgt gctaggtcag tctggcacgt
2341 aagatgaaca tccctaccaa cacagagctc accatctctt atacttaagt gaaaaacatg
2401 gggaagggga aaggggaatg gctgcttttg atatgttccc tgacacatat cttgaatgga
2461 gacctcccta ccaagtgatg aaagtgttga aaaacttaat aacaaatgct tgttgggcaa
2521 gaatgggatt gaggattatc ttctctcaga aaggcattgt gaaggaattg agccagatct
2581 ctctccctac tgcaaaaccc tattgtagta aaaaagtctt ctttactatc ttaataaaac
2641 agatattgtg agattcaaaa aaaaaaaaa aa
```

SEQ ID NO: 2
Amino Acid Sequence - CS1
GI: 19923571 |ref| NM_021181.3| *Homo sapiens* SLAM family member 7
(SLAMF7)

MAGSPTCLTLIYILWQLTGSAASGPVKELVGSVGGAVTFPLKSKVKQVDSIVWTFNTTPLVTIQPEGG

TIIVTQNRNERVDFPDGGYSLKLSKLKKNDSGIYYVGIYSSSLQQPSTQEYVLHVYEHLSKPKVTMG

LQSNKNGTCVTNLTCCMEHGEEDVIYTWKALGQAANESHNGSILPISWRWGESDMTFICVARNPVSRN

FSSPILARKLCEGAADDPDSSMVLLCLLLVPLLLSLFVLGLFLWFLKRERQEEYIEEKKRVDICRETP

NICPHSGENTEYDTIPHTNRTILKEDPANTVYSTVEIPKKMENPHSLLTMPDTPRLFAYENVI

A "full length" CS1 protein or nucleic acid refers to a CS1 polypeptide or polynucleotide sequence, or a variant thereof, that contains elements normally contained in one or more naturally occurring, wild type CS1 polynucleotide or polypeptide sequences. The "full length" may be prior to, or after, various stages of post-translational processing or splicing, including alternative splicing.

"Biological sample" as used herein is a sample of biological tissue or fluid that contains nucleic acids or polypeptides, e.g., of a CS1 protein, polynucleotide, or transcript. Such samples include, but are not limited to, tissue isolated from primates, e.g., humans, or rodents, e.g., mice, and rats. Biological samples may also include sections of tissues such as biopsy and autopsy samples, frozen sections taken for histologic purposes, archival samples, blood, plasma, serum, sputum, stool, tears, mucus, hair, skin, etc. Biological samples also include explants and primary and/or transformed cell cultures derived from patient tissues. A biological sample is typically obtained from a eukaryotic organism, most preferably a mammal such as a primate, e.g., chimpanzee or human; cow; dog; cat; a rodent, e.g., guinea pig, rat, mouse; rabbit; or a bird; reptile; or fish. Livestock and domestic animals are of interest.

"Providing a biological sample" means to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues or materials, having treatment or outcome history, will be particularly useful.

The terms "identical" or percent "identity," in the context of two or more nucleic acids or polypeptide sequences, refer to two or more sequences or subsequences that are the same or have a specified percentage of amino acid residues or nucleotides that are the same (e.g., about 70% identity, preferably 75%, 80%, 85%, 90%, 91%, 93%, 95%, 97%, 98%, 99%, or higher identity over a specified region, when compared and aligned for maximum correspondence over a comparison window or designated region) as measured using, e.g., a BLAST or BLAST 2.0 sequence comparison algorithms with default parameters described below, or by manual alignment and visual inspection. Such sequences are then said to be "substantially identical." This definition also refers to, or may be applied to, the complement of a test sequence. The definition also includes sequences that have deletions and/or insertions, substitutions, and naturally occurring, e.g., polymorphic or allelic variants, and man-made variants. As described below, the preferred algorithms can account for gaps and the like. Preferably, identity exists over a region that is at least about 25 amino acids or nucleotides in length, or more preferably over a region that is about 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of contiguous positions selected from the group consisting typically of from about 20 to 600, usually about 50 to 200, more usually about 100 to 150, in which a sequence may be compared to a reference sequence of the same number of contiguous positions after the two sequences are optimally aligned. Methods of alignment of sequences for comparison are well-known. Optimal alignment of sequences for comparison can be conducted, e.g., by the local homology algorithm of Smith and Waterman (1981) Adv. Appl. Math. 2:482-489, by the homology alignment algorithm of Needleman and Wunsch (1970) J. Mol. Biol. 48:443-453, by the search for similarity method of Pearson and Lipman (1988) Proc. Nat'l. Acad. Sci. USA 85:2444-2448, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel, et al. (eds. 1995 and supplements) Current Protocols in Molecular Biology Wiley).

Preferred examples of algorithms that are suitable for determining percent sequence identity and sequence similarity include the BLAST and BLAST 2.0 algorithms, which are described in Altschul, et al. (1977) Nuc. Acids Res. 25:3389-3402 and Altschul, et al. (1990) J. Mol. Biol. 215:403-410. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, et al., supra). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1992) Proc. Natl. Acad. Sci. USA 89:10915-919) alignments (B) of 50, expectation (E) of 10, M=5, N=−4, and a comparison of both strands.

The BLAST algorithm also performs a statistical analysis of the similarity between two sequences. See, e.g., Karlin and Altschul (1993) Proc. Nat'l. Acad. Sci. USA 90:5873-5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001. Log values may be negative large numbers, e.g., 5, 10, 20, 30, 40, 40, 70, 90, 110, 150, 170, etc.

An indication that two nucleic acid sequences are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, e.g., where the two peptides differ only by conservative substitutions. Another indication that two nucleic acid sequences are substantially identical is that the two molecules or their complements hybridize to each other under stringent conditions. Yet another indication that two nucleic acid sequences are substantially identical is that the same primers can be used to amplify the sequences.

A "host cell" is a naturally occurring cell or a transformed cell that contains an expression vector and supports the replication or expression of the expression vector. Host cells may be cultured cells, explants, cells in vivo, and the like. Host cells may be prokaryotic cells such as E. coli, or eukaryotic cells such as yeast, insect, amphibian, or mammalian cells such as CHO, HeLa, myeloma, and the like (see, e.g., the American Type Culture Collection catalog or web site).

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein or nucleic acid that is the predominant species present in a preparation is substantially purified. In particular, an isolated nucleic acid is separated from some open reading frames that naturally flank the gene and encode proteins other than protein encoded by the gene. The term "purified" in some embodiments denotes that a nucleic acid or protein gives rise to essentially one band in an electrophoretic gel. Preferably, it means that the nucleic acid or protein is at least about 85% pure, more preferably at least 95% pure, and most preferably at least 99% pure. "Purify" or "purification" in other embodiments means removing at least one contaminant or component from the composition to be purified. In this sense, purification does not require that the purified compound be homogeneous, e.g., 100% pure.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain some basic chemical structure as a naturally occurring amino acid. Amino acid mimetic refers to a chemical compound that has a structure that is different from the general chemical structure of an amino acid, but that functions similarly to another amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG, and GCU each encode the amino acid alanine. Thus, at each position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. In certain contexts each codon in a nucleic acid (except AUG, which is ordinarily the only codon for methionine, and TGG, which is ordinarily the only codon for tryptophan) can be modified to yield a functionally similar molecule. Accordingly, a silent variation of a nucleic acid which encodes a polypeptide is implicit in a described sequence with respect to the expression product, but not necessarily with respect to actual probe sequences.

As to amino acid sequences, one of skill will recognize that individual substitutions, deletions, or additions to a nucleic acid, peptide, polypeptide, or protein sequence which alters; adds, or deletes a single amino acid or a small percentage of amino acids in the encoded sequence is a "conservatively modified variant" where the alteration results in the substitution of an amino acid with a chemically similar amino acid. Conservative substitution table providing functionally similar amino acids are well known. Such conservatively modified variants are in addition to and do not exclude polymorphic variants, interspecies homologs, and alleles of the invention. Typically conservative substitutions include for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton (1984) Proteins: Structure and Molecular Properties Freeman).

Macromolecular structures such as polypeptide structures can be described in terms of various levels of organization. For a general discussion of this organization, see, e.g., Alberts, et al. (eds. 2001) Molecular Biology of the Cell (4th ed.) Garland; and Cantor and Schimmel (1980) Biophysical Chemistry Part I: The Conformation of Biological Macromolecules Freeman. "Primary structure" refers to the amino acid sequence of a particular peptide. "Secondary structure" refers to locally ordered, three dimensional structures within a polypeptide. These structures are commonly known as domains. Domains are portions of a polypeptide that often form a compact unit of the polypeptide and are typically 25 to approximately 500 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed, usually by the noncovalent association of independent tertiary units. Anisotropic terms are also known as energy terms.

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50, or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have at least one different linkage, e.g., phosphoramidate, phosphorothioate, phosphorodithioate, or O-methylphosphoroamidite linkages (see Eckstein (1992) Oligonucleotides and Analogues: A Practical Approach Oxford Univ. Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7 of Sanghvi and Cook (eds. 1994) Carbohydrate Modifications in Antisense Research ACS Symposium Series 580. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

A variety of references disclose such nucleic acid analogs, including, e.g., phosphoramidate (Beaucage, et al. (1993) Tetrahedron 49:1925-1963 and references therein; Letsinger (1970) J. Org. Chem. 35:3800-3803; Sprinzl, et al. (1977) E. J. Biochem. 81:579-589; Letsinger, et al. (1986) Nucl. Acids Res. 14:3487-499; Sawai, et al. (1984) Chem. Lett. 805, Letsinger, et al. (1988) J. Am. Chem. Soc. 110:4470-4471; and Pauwels, et al. (1986) Chemica Scripts 26:141-149), phosphorothioate (Mag, et al. (1991) Nucleic Acids Res. 19:1437-441; and U.S. Pat. No. 5,644,048), phosphorodithioate (Brill, et al. (1989) J. Am. Chem. Soc. 111:2321-2322), O-methylphosphoroamidite linkages (see Eckstein (1992) Oligonucleotides and Analogues: A Practical Approach, Oxford Univ. Press), and peptide nucleic acid backbones and linkages (see Egholm (1992) J. Am. Chem. Soc. 114:1895-1897; Meier, et al. (1992) Chem. Int. Ed. Engl. 31:1008-1010; Nielsen (1993) Nature 365:566-568; Carlsson, et al. (1996) Nature 380:207, all of which are incorporated by reference). Other analog nucleic acids include those with positive backbones (Denpcy, et al. (1995) Proc. Natl. Acad. Sci. USA 92:6097-101; non-ionic backbones (U.S. Pat. Nos. 5,386,023, 5,637,684, 5,602,240, 5,216,141, and 4,469,863; Kiedrowski, et al. (1991) Angew. Chem. Intl. Ed. English 30:423-426; Letsinger, et al. (1988) J. Am. Chem. Soc. 110:4470-4471; Letsinger, et al. (1994) Nucleoside and Nucleotide 13:1597; Chapters 2 and 3 in Sanghvi and Cook (eds. 1994) Carbohydrate Modifications in Antisense Research ACS Symposium Series 580; Mesmaeker, et al. (1994) Bioorganic and Medicinal Chem. Lett. 4:395-398; Jeffs, et al. (1994) J. Biomolecular NMR 34:17; Horn, et al. (1996) Tetrahedron Lett. 37:743) and non-ribose backbones, including those described in U.S. Pat. Nos. 5,235,033 and 5,034,506, and Chapters 6 and 7 in Sanghvi and Cook (eds. 1994) Carbohydrate Modifications in Antisense Research ACS Symposium Series 580. Nucleic acids containing one or more carbocyclic sugars are also included within one definition of nucleic acids (see Jenkins, et al. (1995) Chem. Soc. Rev. pp 169-176). Several nucleic acid analogs are described in Rawls (page 35, Jun. 2, 1997) C&E News.

Particularly preferred are peptide nucleic acids (PNA) which includes peptide nucleic acid analogs. Peptide nucleic acids have backbones made from repeating N-(2-aminoiethyl)-glycine units linked by peptide bonds. The different bases (purines and pyrimidines) are linked to the backbone by methylene carbonyl linkages. These backbones are substantially non-ionic under neutral conditions, in contrast to the highly charged phosphodiester backbone of naturally occurring nucleic acids. This results in at least two advantages. The PNA backbone exhibits improved hybridization kinetics, resulting in stronger binding between the PNA/DNA strands, than between PNA strands and DNA strands. PNAs have larger changes in the melting temperature (Tm) for mismatched versus perfectly matched basepairs. DNA and RNA typically exhibit a 2-4° C. drop in Tm for an internal mismatch. With the non-ionic PNA backbone, the drop is closer to 7-9° C. Similarly, due to their non-ionic nature, hybridization of the bases attached to these backbones is relatively insensitive to salt concentration. In addition, PNAs are not degraded by cellular enzymes, and thus can be more stable.

The nucleic acids may be single stranded or double stranded, as specified, or contain portions of both double stranded or single stranded sequence. The depiction of a single strand also defines the sequence of the complementary strand; thus the sequences described herein also provide the complement of the sequence. The nucleic acid may be DNA, both genomic and cDNA, RNA, or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc. "Transcript" typically refers to a naturally occurring RNA, e.g., a pre-mRNA, hnRNA, or mRNA. As used herein, the term "nucleoside" includes nucleotides and nucleoside and nucleotide analogs, and modified nucleosides such as amino modified nucleosides. In addition, "nucleoside" includes non-naturally occurring analog structures. Thus, e.g., the individual units of a peptide nucleic acid, each containing a base, are referred to herein as a nucleoside.

A "label" or a "detectable moiety" is a composition detectable by spectroscopic, photochemical, biochemical, immunochemical, physiological, chemical, or other physical means. In general, labels fall into three classes; a) isotopic labels, which may be radioactive or heavy isotopes; b) immune labels, which may be antibodies, antigens, or epitope tags; and c) colored or fluorescent dyes. The labels may be incorporated into CS1 nucleic acids, proteins, and antibodies. For example, the label should be capable of producing, either directly or indirectly, a detectable signal. The detectable moiety may be a radioisotope, such as 3H, 14C, 32p, 35S, or 125I, electron-dense reagents, a fluorescent or chemiluminescent compound, such as fluorescein isothiocyanate, rhodamine, or luciferin, or an enzyme (e.g., as commonly used in an ELISA), biotin, digoxigenin, or haptens and proteins or other entities which can be made detectable such as alkaline phosphatase, beta-galactosidase, or horseradish peroxidase. Methods are known for conjugating the antibody to the label. See, e.g., Hunter, et al. (1962) Nature 144:945; David, et al. (1974) Biochemistry 13:1014-1021; Pain, et al.

(1981) J. Immunol. Meth. 40:219-230; and Nygren (1982) J. Histochem. and Cytochem. 30:407-412.

An "effector" or "effector moiety" or "effector component" is a molecule that is bound (or linked, or conjugated), either covalently, through a linker or a chemical bond, or noncovalently, through ionic, van der Waals, electrostatic, or hydrogen bonds, to an antibody. The "effector" can be a variety of molecules including, e.g., detection moieties including radioactive compounds, fluorescent compounds, enzymes or substrates, tags such as epitope tags, toxins; activatable moieties, chemotherapeutic agents; lipases; antibiotics; chemoattracting moieties, immune modulators (mica/B), or radioisotopes, e.g., emitting "hard" beta, radiation.

A "labeled nucleic acid probe or oligonucleotide" is one that is bound, e.g., covalently, through a linker or a chemical bond, or noncovalently, through ionic, van der Waals, electrostatic, or hydrogen bonds to a label such that the presence of the probe may be detected by detecting the presence of the label bound to the probe. Alternatively, methods using high affinity interactions may achieve the same results where one of a pair of binding partners binds to the other, e.g., biotin, streptavidin.

As used herein a "nucleic acid probe or oligonucleotide" is a nucleic acid capable of binding to a target nucleic acid of complementary sequence through one or more types of chemical bonds, usually through complementary base pairing, e.g., through hydrogen bond formation. As used herein, a probe may include natural (e.g., A, G, C, or T) or modified bases (7-deazaguanosine, inosine, etc.). In addition, the bases in a probe may be joined by a linkage other than a phosphodiester bond, preferably one that does not functionally interfere with hybridization. Thus, e.g., probes may be peptide nucleic acids in which the constituent bases are joined by peptide bonds rather than phosphodiester linkages. Probes may bind target sequences lacking complete complementarity with the probe sequence depending upon the stringency of the hybridization conditions. The probes are preferably directly labeled, e.g., with isotopes, chromophores, lumiphores, chromogens, or indirectly labeled, e.g., with biotin to which a streptavidin complex may later bind. By assaying for the presence or absence of the probe, one can detect the presence or absence of the select sequence or subsequence. Diagnosis or prognosis may be based at the genomic level, or at the level of RNA or protein expression.

The term "recombinant" when used with reference, e.g., to a cell, or nucleic acid, protein, or vector, indicates that the cell, nucleic acid, protein, or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed, or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, e.g., using the in vivo cellular machinery of the host cell rather than in vitro manipulations; however, such nucleic acids, once produced recombinantly, although subsequently replicated non-recombinantly, are still considered recombinant for the purposes of the invention.

Similarly, a "recombinant protein" is a protein made using recombinant techniques, e.g., through the expression of a recombinant nucleic acid as depicted above. A recombinant protein is distinguished from naturally occurring protein by at least one or more characteristics. The protein may be isolated or purified away from some or most of the proteins and compounds with which it is normally associated in its wild type host, and thus may be substantially pure. An isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of a CS1 protein from one organism in a different organism or host cell. Alternatively, the protein may be made at a significantly higher concentration than is normally seen, through the use of an inducible promoter or high expression promoter, such that the protein is made at increased concentration levels. Alternatively, the protein may be in a form not normally found in nature, as in the addition of an epitope tag or amino acid substitutions, insertions and deletions, as discussed below.

The term "heterologous" when used with reference to portions of a nucleic acid indicates that the nucleic acid comprises two or more subsequences that are not normally found in the same relationship to each other in nature. For instance, the nucleic acid is typically recombinantly produced, having two or more sequences, e.g., from unrelated genes arranged to make a new functional nucleic acid, e.g., a promoter from one source and a coding region from another source. Similarly, a heterologous protein will often refer to two or more subsequences that are not found in the same relationship to each other in nature (e.g., a fusion protein).

A "promoter" is typically an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is active under environmental or developmental regulation. The term "operably linked" refers to a functional linkage between a nucleic acid expression control sequence (such as a promoter, or array of transcription factor binding sites) and a second nucleic acid sequence, e.g., wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed in operable linkage to a promoter.

The phrase "selectively (or specifically) hybridizes to" refers to the binding, duplexing, or hybridizing of a molecule selectively to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in "Overview of principles of hybridization and the strategy of nucleic acid assays" in Tijssen (1993) Hybridization with Nucleic Probes (Laboratory Techniques in Biochemistry and Molecular Biology) (vol. 24) Elsevier. Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal is typically at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. For PCR, a temperature of about 36° C. is typical for low stringency amplification, although annealing temperatures may vary between about 32°-48° C. depending on primer length. For high stringency PCR amplification, a temperature of about 62° C. is typical, although high stringency annealing temperatures can range from about 50-65° C., depending on the primer length and specificity. Typical cycle conditions for both high and low stringency amplifications include a denaturation phase of 90-95° C. for 30-120 sec, an annealing phase lasting 30-120 sec, and an extension phase of about 72° C. for 1-2 min. Protocols and guidelines for low and high stringency amplification reactions are provided, e.g., in Innis, et al. (1990) PCR Protocols: A Guide to Methods and Applications Academic Press, NY.

Nucleic acids that do not hybridize to each other under stringent conditions are still substantially identical if the polypeptides which they encode are substantially identical. This occurs, e.g., when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is typically at least twice background. Alternative hybridization and wash conditions can be utilized to provide conditions of similar stringency. Additional guidelines for determining hybridization parameters are provided in numerous references, e.g., Ausubel, et al. (eds. 1991 and supplements) Current Protocols in Molecular Biology Wiley.

The phrase "changes in cell morphology" or "changes in cellular characteristics" refers to any change in cell morphology or proliferation characteristics in vitro or in vivo, such as cell viability, cell growth, secretion of growth or chemokine factors, changes in cell morphology, gaining or losing inflammation-specific markers, ability to induce or suppress inflammation when injected into suitable animal hosts, and/or induction of a disease state in suitable hosts, e.g. autoimmune disorders and cancerous conditions. See, e.g., pp. 231-241 in Freshney (1994) Culture of Animal Cells a Manual of Basic Technique (2d ed.) Wiley-Liss.

"Diseased cells" refers to spontaneous or induced phenotypic changes that do not necessarily involve the uptake of new genetic material. For example, although myeloma formation can arise from infection with a transforming virus and incorporation of new genomic DNA, or uptake of exogenous DNA, it can also arise spontaneously or following exposure to an agent, thereby inducing expression or alteration of an existing gene. Tumor growth is associated with phenotypic and protein expression changes, such as morphological changes, aberrant cell growth, and/or nonmorphological changes. See, Freshney (2000) Culture of Animal Cells: A Manual of Basic Technique (4th ed.) Wiley-Liss. Similarly, cells affected by autoimmune disease processes are also associated with phenotypic and protein expression changes.

By "an effective" amount of a molecule, or an antibody, or a drug or pharmacologically active agent or pharmaceutical formulation is meant a sufficient amount of the molecule, antibody, drug, agent or formulation to provide the desired effect.

A "subject" or "patient" is used interchangeably herein, which refers to a vertebrate, preferably a mammal, more preferably a human.

As used herein, the term "antibody" or "immunoglobulin" refers to a protein consisting of one or more polypeptides substantially encoded by immunoglobulin genes. The recognized immunoglobulin genes include the kappa, lambda, alpha, gamma ($IgG_1$, $IgG_2$, $IgG_3$, $IgG_4$), delta, epsilon and mu constant region genes, as well as the myriad immunoglobulin variable V region genes (as indicated below, there are V genes for both H—heavy- and L—light-chains). Full-length immunoglobulin "light chains" (about 25 Kd or 214 amino acids) are encoded by a variable region gene, V-kappa or V-lambda, at the NH2-terminus (about 110 amino acids) and, respectively, a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to the tetrameric antibodies, immunoglobulins may exist in a variety of other forms including, for example, Fv, Fab, and (Fab')2, as well as bifunctional hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986), which are incorporated herein by reference).

An immunoglobulin light or heavy chain variable region consists of a "framework" region interrupted by three hypervariable regions, also called complementarity determining regions (CDR's). The extent of the framework region and CDR's have been precisely defined (see, "Sequences of Proteins of Immunological Interest," E. Kabat et al., U.S. Department of Health and Human Services, (1983); which is incorporated herein by reference). The sequences of the framework regions of different light or heavy chains are relatively conserved within a species. As used herein, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDR's. The CDR's are primarily responsible for binding to an epitope of an antigen.

Antibodies also exist, e.g., as a number of well-characterized fragments produced by digestion with various peptidases. Thus, e.g., pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see Paul (ed. 1999) Fundamental Immunology (4th ed.) Raven. While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty, et al. (1990) Nature 348:552-554).

A "chimeric antibody" is an antibody molecule in which (a) the constant region, or a portion thereof, is altered, replaced, or exchanged so that the antigen binding site (variable region) is linked to a constant region of a different or altered class, and/or species, or an entirely different molecule which confers new properties to the chimeric antibody, e.g., an enzyme, toxin, hormone, growth factor, drug, effector function, chemoattractant, immune modulator, etc.; or (b) the variable region, or a portion thereof, is altered, replaced, or exchanged with a variable region having a different or altered antigen specificity.

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. See, e.g. Queen et al., U.S. Pat. Nos. 5,5301,101; 5,585,089; 5,693,761; 5,693,762; and 6,180,370 (These and the other U.S. patents/patent applications are incorporated by reference in their entirety).

For preparation of antibodies, e.g., recombinant, monoclonal, or polyclonal antibodies, many techniques known. See, e.g., Kohler and Milstein (1975) Nature 256:495-497; Kozbor, et al. (1983) Immunology Today 4:72; Cole, et al. (1985) pp. 77-96 in Reisfeld and Sell (1985) Monoclonal Antibodies and Myeloma Therapy Liss; Coligan (1991) Current Protocols in Immunology Lippincott; Harlow and Lane (1988) Antibodies: A Laboratory Manual CSH Press; and Goding (1986) Monoclonal Antibodies: Principles and Practice (2d ed.) Academic Press. Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens. See, e.g., McCafferty, et al. (1990) Nature 348:552-554; Marks, et al. (1992) Biotechnology 10:779-783.

The term "epitope" refers to any portion (determinant) of a protein that is capable of eliciting an immune response and being specifically bound by an antibody. Epitope determinants usually consist of active surface groupings of molecules such as amino acids or GAG side chains and usually have specific three-dimensional structural characteristics, as well as specific charge characteristics. Two antibodies are said to bind to substantially the same epitope of a protein (or the overlapping epitope of a protein) if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody. The determination of whether two antibodies bind substantially to the same epitope is accomplished by the methods known in the art, such as a competition assay. In conducting an antibody competition study between a control antibody (for example, one of the anti-CS1 antibodies described herein) and any test antibody, one may first label the control antibody with a detectable label, such as, biotin, enzymatic, radioactive label, or fluorescent label to enable the subsequent identification. A test (unlabeled) antibody that binds to substantially the same epitope as the control (labeled) antibody should be able to block control antibody binding and thus should reduce control antibody binding.

In an exemplary embodiment, if an antibody binds substantially to the same epitope of a Luc monoclonal antibody (Luc monoclonal antibodies refer to the produced anti-CS1 monoclonal antibodies of the present invention), the antibody should bind to an epitope of CS1 that overlaps with the CS1 epitope that the Luc monoclonal antibody binds to. The overlapping region can range from one amino acid residue to several hundred amino acid residues. This antibody should then compete with and/or block the binding of the Luc monoclonal antibody to CS1 and thereby decrease the binding of the Luc monoclonal antibody to CS1, preferably by at least about 50% in a competition assay.

An epitope is recognized by an antibody when the epitope binds to the antibody with a binding affinity of at least $10^5$ $M^{-1}$, preferably $10^6$ to $10^7$ $M^{-1}$, more preferably $10^8$ to $10^9$ $M^{-1}$, even more preferably $10^{10}$ $M^{-1}$ or stronger.

The term "derived from" means "obtained from" or "produced by" "or "descending from".

CS1 Antigens and Antibodies

SEQ ID NO:2 depicts the amino acid sequences of the full-length wild-type human CS1. A "functionally active" CS1 fragment or derivative exhibits one or more functional activities associated with a full-length, wild-type CS1 protein, such as antigenic or immunogenic activity, ability to bind natural cellular substrates, etc. The functional activity of CS1 proteins, derivatives and fragments can be assayed by various methods known to one skilled in the art (Current Protocols in Protein Science, Coligan et al., eds., John Wiley & Sons, Inc., Somerset, N.J. (1998)). For purposes herein, functionally active fragments also include those fragments that comprise one or more structural domains of a CS1 polypeptide, such as a binding domain. Protein domains can be identified using the PFAM program (Bateman A., et al., Nucleic Acids Res. 27: 260-2 (1999)).

CS1 polypeptide derivatives typically share a certain degree of sequence identity or sequence similarity with SEQ ID NO:2 or a fragment thereof. CS1 derivatives can be produced by various methods known in the art. The manipulations that result in their production can occur at the gene or protein level. For example, a cloned CS1 gene sequence (e.g. SEQ ID NO:1) can be cleaved at appropriate sites with restriction endonuclease(s) (Wells et al., Philos. Trans. R. Sot. London SerA 317: 415 (1986)), followed by further enzymatic modification, if desired, then isolated, and ligated in vitro, and expressed to produce the desired derivative. Alternatively, a CS1 gene can be mutated in vitro or in vivo to create and/or destroy translation, initiation, and/or termination sequences, or to create variations in coding regions and/or to form new restriction endonuclease sites or destroy pre-existing ones, to facilitate further in vitro modification. A variety of mutagenesis techniques are known in the art such as chemical mutagenesis, in vitro site-directed mutagenesis (Carter et al., Nucl. Acids Res. 13: 4331 (1986)), or use of TAB linkers (available from Pfizer, Inc.).

In one aspect, the antibodies of the present invention neutralize at least one, or preferably all, biological activities of CS1. The biological activities of CS1 include: 1) binding activities of its cellular substrates, such as its ligands (for instance, these neutralizing antibodies should be capable of competing with or completely blocking the binding of CS1 to at least one, and preferably all, of its ligands); 2) signaling transduction activities; and 3) cellular responses induced by CS1.

The present invention provides for the hybridoma cell lines: Luc2, Luc3, Luc15, Luc22, Luc23, Luc29, Luc32, Luc34, Luc35, Luc37, Luc38, Luc39, Luc56, Luc60, Luc63, Luc69, LucX.1, LucX.2 or Luc90. The hybridoma cell line Luc90 has been deposited with the American Type Culture Collection (ATCC) at P.O. Box 1549, Manassas, Va. 20108, as accession number PTA 5091. The deposit of this hybridoma cell line was received by the ATCC on Mar. 26, 2003. The hybridoma cell line Luc63.2.22, which produces the monoclonal antibody Luc63, has also been deposited with the ATCC at the address listed above. The deposit of the Luc63-producing hybridoma was received by the ATCC on May 6, 2004, and the hybridoma was assigned deposit number PTA-5950.

The present invention provides for monoclonal antibodies produced by the hybridoma cell lines: Luc2, Luc3, Luc15, Luc22, Luc23, Luc29, Luc32, Luc34, Luc35, Luc37, Luc38, Luc39, Luc56, Luc60, Luc63, Luc69, LucX.1, LucX.2 or Luc90 (ATCC Accession Number PTA 5091). These monoclonal antibodies are named as the antibodies: Luc2, Luc3, Luc15, Luc22, Luc23, Luc29, Luc32, Luc34, Luc35, Luc37, Luc38, Luc39, Luc56, Luc60, Luc63, Luc69, LucX.1, LucX.2 and Luc90, respectively, hereafter.

The present invention provides for antibodies, preferably monoclonal antibodies, that bind substantially to the same epitope as any one of the Luc monoclonal antibodies described herein.

The present invention provides for antibodies, preferably monoclonal antibodies, that do not bind substantially to the same epitope as one or more of the Luc monoclonal antibodies described above.

A variety of immunological screening assays for the assessment of the antibody competition can be used to identify the antibodies that bind to substantially the same epitope of an antibody of the present invention or bind to a different epitope from that of an antibody of the present invention.

In conducting an antibody competition study between a control antibody and any test antibody (irrespective of species or isotype), one may first label the control with a detectable label, such as, biotin or an enzymatic (or even radioactive) label to enable subsequent identification. In this case, one would pre-mix or incubate the unlabeled antibody with cells expressing the CS1 protein. The labeled antibody is then added to the pre-incubated cells. The intensity of the bound label is measured. If the labeled antibody competes with the unlabeled antibody by binding to an overlapping epitope, the intensity will be decreased relative to the binding by negative control unlabeled antibody (a known antibody that does not bind CS1).

The assay may be any one of a range of immunological assays based upon antibody competition, and the control antibodies would be detected by means of detecting their label, e.g., by using streptavidin in the case of biotinylated antibodies or by using a chromogenic substrate in connection with an enzymatic label (such as 3,3'5,5'-tetramethylbenzidine (TMB) substrate with peroxidase enzyme) or by simply detecting a radioactive label or a fluorescence label. An antibody that binds to the same epitope as the control antibodies will be able to effectively compete for binding and thus will significantly reduce (for example, by at least 50%) the control antibody binding, as evidenced by a reduction in the bound label.

The reactivity of the (labeled) control antibodies in the absence of a completely irrelevant antibody would be the control high value. The control low value would be obtained by incubating the unlabeled test antibodies with cells expressing CS1 and then incubate the cell/antibody mixture with labeled control antibodies of exactly the same type, when competition would occur and reduce binding of the labeled antibodies. In a test assay, a significant reduction in labeled antibody reactivity in the presence of a test antibody is indicative of a test antibody that recognizes substantially the same epitope.

Antibodies against CS1 of all species of origins are included in the present invention. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal after being immunized with an antigen, such as a polypeptide, preferably a human polypeptide. In a preferred embodiment, the antibody of the present invention is an isolated natural antibody that binds to and/or neutralizes CS1.

The genetically altered anti-CS1 antibodies should be functionally equivalent to the above-mentioned natural antibodies. Modified antibodies providing improved stability or/and therapeutic efficacy are preferred. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this invention can be modified post-translationally (e.g., acetylation, and/or phosphorylation) or can be modified synthetically (e.g., the attachment of a labeling group). Preferred genetically altered antibodies are chimeric antibodies and humanized antibodies.

The chimeric antibody is an antibody having a variable region and a constant region derived from two different antibodies, preferably derived from separate species. Preferably, the variable region of the chimeric antibody is derived from murine and the constant region is derived from human.

In one embodiment, the murine variable regions are derived from any one of the monoclonal antibodies described herein. In order to produce the chimeric antibodies, the portions derived from two different species (e.g., human constant region and murine variable or binding region) can be joined together chemically by conventional techniques or can be prepared as single contiguous proteins using genetic engineering techniques. The DNA molecules encoding the proteins of both the light chain and heavy chain portions of the chimeric antibody can be expressed as contiguous proteins. The method of making chimeric antibodies is disclosed in U.S. Pat. Nos. 5,677,427; 6,120,767; and 6,329,508, each of which is incorporated by reference in its entirety.

The genetically altered antibodies used in the present invention include humanized antibodies that bind to and neutralize CS1. In one embodiment, said humanized antibody comprising CDRs of a mouse donor immunoglobulin and heavy chain and light chain frameworks and constant regions of a human acceptor immunoglobulin. In one example, the humanized antibodies are the humanized versions of any one of the antibodies described herein. The method of making humanized antibody is disclosed in U.S. Pat. Nos. 5,530,101; 5,585,089; 5,693,761; 5,693,762; and 6,180,370 each of which is incorporated herein by reference in its entirety.

Anti-CS1 fully human antibodies are also included in the present invention. In a preferred embodiment of the present invention, said fully human antibodies are isolated human antibodies that neutralize the activities of CS1 described herein.

Fully human antibodies against CS1 are produced by a variety of techniques. One example is trioma methodology. The basic approach and an exemplary cell fusion partner, SPAZ-4, for use in this approach have been described by Oestberg et al., Hybridoma 2:361-367 (1983); Oestberg, U.S. Pat. No. 4,634,664; and Engleman et al., U.S. Pat. No. 4,634,666 (each of which is incorporated by reference in its entirety).

Human antibodies against CS1 can also be produced from non-human transgenic animals having transgenes encoding at least a segment of the human immunoglobulin locus. The production and properties of animals having these properties are described in detail by, see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety.

Various recombinant antibody library technologies may also be utilized to produce fully human antibodies. For example, one approach is to screen a DNA library from human B cells according to the general protocol outlined by Huse et al., Science 246:1275-1281 (1989). Antibodies binding CS1 or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated by reference in its entirety). In these methods, libraries of phage are produced in which members display different antibodies on their outer surfaces. Antibodies are usually displayed as Fv or Fab fragments. Phage displaying antibodies with a desired specificity are selected by affinity enrichment to CS1 or fragment thereof.

Eukaryotic ribosomes can also be used as means to display a library of antibodies and isolate the binding human antibodies by screening against the target antigen, such as CS1, as described in Coia G, et al., J. Immunol. Methods 1: 254 (1-2):191-7 (2001); Hanes J. et al., Nat. Biotechnol. 18 (12): 1287-92 (2000); Proc. Natl. Acad. Sci. U.S.A. 95 (24):14130-5 (1998); Proc. Natl. Acad. Sci. U.S.A. 94 (10): 4937-42 (1997), each of which in incorporated by reference in its entirety.

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212-20 (2002); Boeder, E. T., et al., Nat. Biotechnol. 15(6):553-7 (1997), each of which is herein incorporated by reference in its entirety. Alternatively, human antibody libraries may be expressed intracellularly and screened via yeast two-hybrid system (WO0200729A2, which is incorporated by reference in its entirety).

Fragments of the anti-CS1 antibodies, which retain the binding specificity to CS1, are also included in the present invention. Examples of these antigen-binding fragments include, but are not limited to, partial or full heavy chains or light chains, variable regions, or CDR regions of any anti-CS1 antibodies described herein.

In a preferred embodiment of the invention, the antibody fragments (antigen binding fragments) are truncated chains (truncated at the carboxyl end). Preferably, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CH1 domains); Fv fragments (consisting of VL and VH domains of a single chain of an antibody); dab fragments (consisting of a VH domain); isolated CDR regions; (Fab')2 fragments, bivalent fragments (comprising two Fab fragments linked by a disulphide bridge at the hinge region). The truncated chains can be produced by conventional biochemistry techniques, such as enzyme cleavage, or recombinant DNA techniques, each of which is known in the art. These polypeptide fragments may be produced by proteolytic cleavage of intact antibodies by methods well known in the art, or by inserting stop codons at the desired locations in the vectors using site-directed mutagenesis, such as after CHI to produce Fab fragments or after the hinge region to produce (Fab')2 fragments. Single chain antibodies may be produced by joining VL and VH_coding regions with a DNA that encodes a peptide linker connecting the VL and VH protein fragments Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated by reference in its entirety) to produce fusion proteins (e.g., immunotoxins) or conjugates having novel properties.

The present invention comprises the use of anti-CS1 antibodies in immunotoxins. Conjugates that are immunotoxins including antibodies have been widely described in the art. The toxins may be coupled to the antibodies by conventional coupling techniques or immunotoxins containing protein toxin portions can be produced as fusion proteins. The conjugates of the present invention can be used in a corresponding way to obtain such immunotoxins. Illustrative of such immunotoxins are those described by Byers, B. S. et al., Seminars Cell Biol 2:59-70 (1991) and by Fanger, M. W. et al., Immunol Today 12:51-54 (1991).

Recombinant DNA techniques can be used to produce the recombinant anti-CS1 antibodies, as well as the chimeric or humanized anti-CS1 antibodies or any other anti-CS1 genetically-altered antibodies and the fragments or conjugate thereof in any expression systems including both prokaryotic and eukaryotic expression systems, such as bacteria, yeast, insect cells, plant cells, and mammalian cells (for example, NSO cells).

Once produced, the whole antibodies, their dimers, individual light and heavy chains, or other immunoglobulin forms of the present invention can be purified according to standard procedures of the art, including ammonium sulfate precipitation, affinity columns, column chromatography, gel electrophoresis and the like (see, generally, Scopes, R., Protein Purification (Springer-Verlag, N.Y., 1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extra corporeally) or in developing and performing assay procedures, immunofluorescent stainings, and the like. (See, generally, Immunological Methods, Vols. I and II (Lefkovits and Pernis, eds., Academic Press, NY, 1979 and 1981). The isolated or purified anti-CS1 antibodies can be further screened for their ability of neutralizing the biological activities of CS1 as described in the Examples.

CS1 Structural Model

The open reading frame of the human CS1 gene (SEQ ID NO. 1) encodes a polypeptide of 335 amino acid residues (SEQ ID NO. 2). The predicted protein sequence had a putative signal peptide sequence and an extracellular domain of about 225 amino acid residues, followed by a single transmembrane domain of about 25 amino acid residues and an intracellular domain of about 85 amino acid residues. The extracellular domain contained seven putative N-linked glycosylation sites. The homology of the predicted protein sequence of CS1 indicates that it is a member of the Ig superfamily. Alignment of the CS1 protein sequence indicates a similar structure with many conserved residues compared to other CD2 subset receptors. The cytoplasmic region contains two of the novel tyrosine motifs observed in 2B4 and SLAM.

A structural model of the extracellular domain of CS1 is predicted to consist of two immunoglobulin-like domains. The N-terminal domain 1 (V domain) is a member of the V subset, and domain 2 (C2 domain) a member of the C2 subset of immunoglobulin-like domains, as in CD2 (PDB code: 1HNF). The extracellular domain is linked at its C-terminal end to the transmembrane domain starting at about amino acid residue 226.

In V domain (from about amino acid residue 23 to about amino acid residue 122), Trp-53 at the core of the domain is conserved, and all residues in the immediate vicinity are either identical with those of CD2 (Leu-90 and Val-105) or conservatively substituted (Tyr-120 for Phe in CD2). As in CD2, there is no infra-domain disulphide bridge in the V domain. In C2 domain (from about amino acid residue 128 to about amino acid residue 225), the two intra-domain disulphide bonds are conserved (Cys-151-Cys-195; Cys-145-Cys 215), and all residues in the immediate vicinity of the former, in the core of the domain, are either identical with those of CD2 (Pro-131) or conservatively substituted (Val-133, Ile-161, Leu-180 in CS1, for Ile, Leu and Ile respectively in CD2). The inter-domain linker region (from about amino acid residue 123 to about amino acid residue 127) is also identical in length between CS1 and CD2 and shows some conservation (Val-Tyr-Glu-His-Leu in CS1 versus Ile-Gln-Glu-Arg-Val in CD2).

There are seven potential N-linked glycosylation sites, two in V domain (Asn-56 and Asn-98), and five in C2 domain (Asn-142, Asn-148, Asn-172, Asn-176 and Asn-204).

Structural similarity in the context of sequences and motifs between CS1 and proteins defined by CD antigens suggests that CS1 proteins may be a potential target for diseases such as inflammation, cancer, and immune disorders. Therapeutic uses of anti-CS1 antibodies, such as Luc antibodies, include inhibition of immunoglobulin production, inhibition of leukocyte function in autoimmune diseases and in cancers expressing CS1 proteins.

Use of CS1 Nucleic Acids

As described above, CS1 sequences is initially identified by substantial nucleic acid and/or amino acid sequence homology or linkage to the CS1 sequences of Table 2. Such homology can be based upon the overall nucleic acid or amino acid sequence, and is generally determined using either homology programs or hybridization conditions. Typically, linked sequences on an mRNA are found on the same molecule.

Percent identity of a sequence can be determined using an algorithm such as BLAST. A preferred method utilizes the BLASTN module of WU-BLAST-2 set to the default parameters, with overlap span and overlap fraction set to 1 and 0.125, respectively. Alignment may include the introduction of gaps in the sequences to be aligned. In addition, for sequences which contain either more or fewer nucleotides than those of the nucleic acids described, the percentage of homology may be determined based on the number of homologous nucleosides in relation to the total number of nucleosides. Thus, e.g., homology of sequences shorter than those of the sequences identified will be determined using the number of nucleosides in the shorter sequence.

In one embodiment, nucleic acid homology is determined through hybridization studies. Thus, e.g., nucleic acids which hybridize under high stringency to a described nucleic acid, or its complement, or is also found on naturally occurring mRNAs is considered a homologous sequence. In another embodiment, less stringent hybridization conditions are used; e.g., moderate or low stringency conditions may be used; see Ausubel, supra, and Tijssen, supra.

The CS1 nucleic acid sequences of the invention, e.g., the sequences in Table 2, can be fragments of larger genes, e.g., they are nucleic acid segments. "Genes" in this context includes coding regions, non-coding regions, and mixtures of coding and non-coding regions. Accordingly, using the sequences provided herein, extended sequences, in either direction, of the CS1 genes can be obtained, using techniques well known for cloning either longer sequences or the full length sequences; see Ausubel, et al., supra. Much can be done by informatics and many sequences can be clustered to include multiple sequences corresponding to a single gene, e.g., systems such as UniGene.

The CS1 nucleic acids of the present invention are used in several ways. In one embodiment, nucleic acid probes to CS1 are made and attached to biochips to be used in screening and diagnostic methods, as outlined below, or for administration, e.g., for gene therapy, vaccine, RNAi, and/or antisense applications. Alternatively, CS1 nucleic acids that include coding regions of CS1 protein can be put into expression vectors for the expression of CS1 protein, again for screening purposes or for administration to a patient.

In another embodiment, nucleic acid probes to CS1 nucleic acid (both the nucleic acid sequences outlined in the figures and/or the complements thereof) are made. The nucleic acid probes attached to the biochip are designed to be substantially complementary to the CS1 nucleic acid, e.g., the target sequence (either the target sequence of the sample or to other probe sequences, e.g., in sandwich assays), such that hybridization of the target sequence and the probes of the present invention occurs. As outlined below, this complementarity need not be perfect; there may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A nucleic acid probe is generally single stranded but can be partially single and partially double stranded. The strandedness of the probe is dictated by the structure, composition, and properties of the target sequence. In general, the nucleic acid probes range from about 8-100 bases long, with from about 10-80 bases being preferred, and from about 30-50 bases being particularly preferred. That is, generally whole genes are not used. In some embodiments, much longer nucleic acids can be used, up to hundreds of bases.

In another embodiment, more than one probe per sequence is used, with either overlapping probes or probes to different sections of the target being used. That is, two, three, four or more probes, with three being preferred, are used to build in a redundancy for a particular target. The probes can be overlapping (e.g., have some sequence in common), or separate. In some cases, PCR primers may be used to amplify signal for higher sensitivity.

Nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal as outlined. The binding can typically be covalent or non-covalent. By "non-covalent binding" and grammatical equivalents herein is meant one or more of electrostatic, hydrophilic, and hydrophobic interactions. Included in non-covalent binding is the covalent attachment of a molecule, e.g., streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds, and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant a material that can be modified for the attachment or association of the nucleic acid probes and is amenable to at least one detection method. Often, the substrate may contain discrete individual sites appropriate for individual partitioning and identification. The number of possible substrates is very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably fluoresce. See WO 0055627.

Generally the substrate is planar, although other configurations of substrates may be used as well. For example, the probes may be placed on the inside surface of a tube for flow-through sample analysis to minimize sample volume. Similarly, the substrate may be flexible, such as a flexible foam, including closed cell foams of particular plastics.

In one embodiment, the surface of the biochip and the probe may be derivatized with chemical functional groups for subsequent attachment of the two. Thus, e.g., the biochip is. derivatized with a chemical functional group including, but not limited to, amino groups, carboxy groups, oxo groups, and thiol groups, with amino groups being particularly preferred. Using these functional groups, the probes can be attached using functional groups on the probes. For example, nucleic acids containing amino groups can be attached to surfaces comprising amino groups, e.g., using linkers; e.g., homo- or hetero-bifunctional linkers as are well known (see 1994 Pierce Chemical Company catalog, technical section on cross-linkers, pages 155-200). In addition, in some cases, additional linkers, such as alkyl groups (including substituted and heteroalkyl groups) may be used.

In this embodiment, oligonucleotides are synthesized, and then attached to the surface of the solid support. Either the 5' or 3' terminus may be attached to the solid support, or attachment may be via linkage to an internal nucleoside. In another embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface. For example, photoactivation techniques utilizing photopolymerization compounds and techniques are used. In another embodiment, the nucleic acids can be synthesized in situ, using known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affymetrix GENECHIP® (DNA Microarray chip) technology.

Often, amplification-based assays are performed to measure the expression level of CS1-associated sequences. These assays are typically performed in conjunction with reverse transcription. In such assays, a CS1-associated nucleic acid sequence acts as a template in an amplification reaction (e.g., Polymerase Chain Reaction, or PCR). In a quantitative amplification, the amount of amplification product will be proportional to the amount of template in the original sample. Comparison to appropriate controls provides a measure of the amount of CS1-associated A. Methods of quantitative amplification are well known. Detailed protocols for quantitative PCR are provided, e.g., in Innis, et al. (1990) PCR Protocols: A Guide to Methods and Applications Academic Press.

In some embodiments, a TAQMAN® (a fluorogenic oligonucleotide probe) based assay is used to measure expression. TAQMAN® based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AMPLITAQ® (DNA polymerase), results in the cleavage of the TAQMAN® probe. This cleavage separates the 5' fluorescent dye and the 3' quenching agent, thereby resulting in an increase in fluorescence as a function of amplification (see, e.g., literature provided by Perkin-Elmer).

Other suitable amplification methods include, but are not limited to, ligase chain reaction (LCR) (see Wu and Wallace (1989) Genomics 4:560-569, Landegren, et al. (1988) Science 241:1077-1080, and Barringer, et al. (1990) Gene 89:117-122), transcription amplification (Kwoh, et al. (1989) Proc. Natl. Acad. Sci. USA 86:1173-1177), self-sustained sequence replication (Guatelli, et al. (1990) Proc. Natl. Acad. Sci. USA 87:1874-1878), dot PCR, linker adapter PCR, etc.

Expression of CS1 Protein from Nucleic Acids

In one embodiment, CS1 nucleic acid, e.g., encoding CS1 protein, are used to make a variety of expression vectors to express CS1 protein which can then be used in developing reagents for diagnostic assays as described below. Expression vectors and recombinant DNA technology are well known (see, e.g., Ausubel, supra, and Fernandez and Hoeffler (eds. 1999) Gene Expression Systems Academic Press) to express proteins. The expression vectors may be either self-replicating extrachromosomal vectors or vectors which integrate into a host genome. Generally, these expression vectors include transcriptional and translational regulatory nucleic acid operably linked to the nucleic acid encoding the CS1 protein. The term "control sequences" refers to DNA sequences used for the expression of an operably linked coding sequence in a particular host organism. Control sequences that are suitable for prokaryotes, e.g., include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is typically accomplished by ligation at convenient restriction sites. If such sites do not exist, synthetic oligonucleotide adaptors or linkers are used in accordance with conventional practice. Transcriptional and translational regulatory nucleic acid will generally be appropriate to the host cell used to express the CS1 protein. Numerous types of appropriate expression vectors and suitable regulatory sequences are known for a variety of host cells.

In general, transcriptional and translational regulatory sequences may include, but are not limited to, promoter sequences, ribosomal binding sites, transcriptional start and stop sequences, translational start and stop sequences, and enhancer or activator sequences. In one embodiment, the regulatory sequences include a promoter and transcriptional start and stop sequences.

Promoter sequences may be either constitutive or inducible promoters. The promoters may be either naturally occurring promoters or hybrid promoters. Hybrid promoters, which combine elements of more than one promoter, are also known, and are useful in the present invention.

An expression vector may comprise additional elements. For example, the expression vector may have two replication systems, thus allowing it to be maintained in two organisms, e.g., in mammalian or insect cells for expression and in a prokaryotic host for cloning and amplification. Furthermore, for integrating expression vectors, the expression vector often contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are available. See, e.g., Fernandez and Hoeffler, supra; and Kitamura, et al. (1995) Proc. Nat'l Acad. Sci. USA 92:9146-9150.

In addition, in another embodiment, the expression vector contains a selectable marker gene to allow the selection of transformed host cells. Selection genes are well known and will vary with the host cell used.

The CS1 protein of the present invention are usually produced by culturing a host cell transformed with an expression vector containing nucleic acid encoding a CS1 protein, under the appropriate conditions to induce or cause expression of the CS1 protein. Conditions appropriate for CS1 protein expression will vary with the choice of the expression vector and the host cell, and will be easily ascertained through routine experimentation or optimization. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archaebacteria, fungi, and insect and animal cells, including mammalian cells. Of particular interest are *Saccharomyces cerevisiae* and other yeasts, *E. coli, Bacillus subtilis*, Sf9 cells, C129 cells, 293 cells, Neurospora, BHK, CHO, COS, HeLa cells, HUVEC (human umbilical vein endothelial cells), THP1 cells (a macrophage cell line), and various other human cells and cell lines.

In one embodiment, the CS1 proteins are expressed in mammalian cells. Mammalian expression systems may be used, and include retroviral and adenoviral systems. One expression vector system is a retroviral vector system such as is generally described in PCT/US97/01019 and PCT/US97/01048. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter (see, e.g., Fernandez and Hoeffler, supra). Typically, transcription termination and polyadenylation sequences recognized by mammalian cells are regulatory regions located 3' to the translation stop codon and thus, together with the promoter elements, flank the coding sequence. Examples of transcription terminator and polyadenlyation signals include those derived from SV40.

Methods of introducing exogenous nucleic acid into mammalian hosts, as well as other hosts, are available, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In another embodiment, CS1 protein is expressed in bacterial systems. Promoters from bacteriophage may also be used. In addition, synthetic promoters and hybrid promoters are also useful; e.g., the tac promoter is a hybrid of the trp and lac promoter sequences. Furthermore, a bacterial promoter can include naturally occurring promoters of non-bacterial origin that have the ability to bind bacterial RNA polymerase and initiate transcription. In addition to a functioning promoter sequence, an efficient ribosome binding site is desirable. The expression vector may also include a signal peptide sequence that provides for secretion of the CS1 protein in bacteria. The protein is either secreted into the growth media (gram-positive bacteria) or into the periplasmic space, located between the inner and outer membrane of the cell (gram-negative bacteria). The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin, and tetracycline. Selectable markers also include biosynthetic genes, such as those in the histidine, tryptophan, and leucine biosynthetic pathways. These components are assembled into expression vectors. Expression vectors for bacteria are well known, and include vectors for *Bacillus subtilis*, *E. coli*, *Streptococcus cremoris*, and *Streptococcus lividans*, among others (e.g., Fernandez and Hoeffler, supra). The bacterial expression vectors are transformed into bacterial host cells using techniques such as calcium chloride treatment, electroporation, and others.

In one embodiment, CS1 protein is produced in insect cells using, e.g., expression vectors for the transformation of insect cells, and in particular, baculovirus-based expression vectors.

In another embodiment, a CS1 protein is produced in yeast cells. Yeast expression systems are well known, and include expression vectors for *Saccharomyces cerevisiae*, *Candida albicans* and *C. maltosa*, *Hansenula polymorpha*, *Kluyveromyces fragilis* and *K. lactis*, *Pichia guillerimondii* and *P. pastoris*, *Schizosaccharomyces pombe*, and *Yarrowia lipolytica*.

The CS1 protein may also be made as a fusion protein, using available techniques. Thus, e.g., for the creation of monoclonal antibodies, if the desired epitope is small, the CS1 protein may be fused to a carrier protein to form an immunogen. Alternatively, the CS1 protein may be made as a fusion protein to increase expression, or for other reasons. For example, when the CS1 protein is a CS1 peptide, the nucleic acid encoding the peptide may be linked to other nucleic acid for expression purposes. Fusion with detection epitope tags can be made, e.g., with FLAG, His6, myc, HA, etc.

In yet another embodiment, the CS1 protein is purified or isolated after expression. CS1 protein may be isolated or purified in a variety of ways depending on what other components are present in the sample and the requirements for purified product, e.g., natural conformation or denatured. Standard purification methods include ammonium sulfate precipitations, electrophoretic, molecular, immunological, and chromatographic techniques, including ion exchange, hydrophobic, affinity, and reverse-phase HPLC chromatography, and chromatofocusing. For example, the CS1 protein may be purified using a standard anti-CS1 protein antibody column Ultrafiltration and diafiltration techniques, in conjunction with protein concentration, are also useful. See, e.g., Walsh (2002) Proteins: Biochemistry and Biotechnology Wiley; Hardin, et al. (eds. 2001) Cloning, Gene Expression and Protein Purification Oxford Univ. Press; Wilson, et al. (eds. 2000) Encyclopedia of Separation Science Academic Press; and Scopes (1993) Protein Purification Springer-Verlag. The degree of purification necessary will vary depending on the use of the CS1 protein. In some instances no purification will be necessary.

Once expressed and purified if necessary, the CS1 proteins and nucleic acids are useful in a number of applications. They may be used as immunoselection reagents, as vaccine reagents, as screening agents, therapeutic entities, for production of antibodies, as transcription or translation inhibitors, etc.

Variants of CS1 Proteins

Also included within one embodiment of CS1 proteins are amino acid variants of the naturally occurring sequences, as determined herein. Preferably, the variants are preferably greater than about 75% homologous to the wild-type sequence, more preferably greater than about 80%, even more preferably greater than about 85%, and most preferably greater than 90%. In some embodiments the homology will be as high as about 93-95% or 98%. As for nucleic acids, homology in this context means sequence similarity or identity, with identity being preferred. This homology will be determined using standard techniques, as are outlined above for nucleic acid homologies.

CS1 protein of the present invention may be shorter or longer than the wild type amino acid sequences. Thus, in one embodiment, included within the definition of CS1 proteins are portions or fragments of the wild type sequences herein. In addition, as outlined above, the CS1 nucleic acid of the invention may be used to obtain additional coding regions, and thus additional protein sequence.

In one embodiment, CS1 proteins are derivative or variant CS1 proteins as compared to the wild-type sequence. That is, as outlined more fully below, the derivative CS1 peptide will often contain at least one amino acid substitution, deletion, or insertion, with amino acid substitutions being particularly preferred. The amino acid substitution, insertion, or deletion may occur at many residue positions within the CS1 peptide.

Also included within one embodiment of CS1 proteins of the present invention are amino acid sequence variants. These variants typically fall into one or more of three classes: substitutional, insertional, or deletional variants. These variants ordinarily are prepared by site specific mutagenesis of nucleotides in the DNA encoding the CS1 protein, using cassette or PCR mutagenesis or other techniques, to produce DNA encoding the variant, and thereafter expressing the DNA in recombinant cell culture as outlined above. However, variant CS1 protein fragments having up to about 100-150 residues may be prepared by in vitro synthesis using established techniques. Amino acid sequence variants are characterized by the predetermined nature of the variation, a feature that sets them apart from naturally occurring allelic or interspecies variation of the CS1 protein amino acid sequence. The variants typically exhibit a similar qualitative biological activity as a naturally occurring analogue, although variants can also be selected which have modified characteristics.

While the site or region for introducing an amino acid sequence variation is often predetermined, the mutation per se need not be predetermined. For example, in order to optimize the performance of a mutation at a given site, random mutagenesis may be conducted at the target codon or region and the expressed CS1 variants screened for the optimal combination of desired activity. Techniques for making substitution mutations at predetermined sites in DNA having a known sequence are well known, e.g., M13 primer mutagenesis and PCR mutagenesis. Screening of mutants is often done using assays of CS1 protein activities.

Amino acid substitutions are typically of single residues; insertions usually will be on the order of from about 1-20 amino acids, although considerably larger insertions may be tolerated. Deletions generally range from about 1-20 residues, although in some cases deletions may be much larger.

Substitutions, deletions, insertions, or combination thereof may be used to arrive at a final derivative. Generally these changes are done on a few amino acids to minimize the alteration of the molecule. However, larger changes may be tolerated in certain circumstances. When small alterations in the characteristics of the CS1 protein are desired, substitutions are generally made in accordance with the amino acid substitution relationships described.

The variants typically exhibit essentially the same qualitative biological activity and will elicit the same immune response as a naturally-occurring analog, although variants also are selected to modify the characteristics of CS1 proteins as needed. Alternatively, the variant may be designed such that a biological activity of the CS1 protein is altered. For example, glycosylation sites may be added, altered, or removed.

Substantial changes in function or immunological identity are sometimes made by selecting substitutions that are less conservative than those described above. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. Substitutions which generally are expected to produce the greatest changes in the polypeptide's properties are those in which (a) a hydrophilic residue, e.g., serine or threonine is substituted for (or by) a hydrophobic residue, e.g., leucine, isoleucine, phenylalanine, valine, or alanine; (b) a cysteine or proline is substituted for (or by) another residue; (c) a residue having an electropositive side chain, e.g., lysine, arginine, or histidine, is substituted for (or by) an electronegative residue, e.g., glutamic or aspartic acid; (d) a residue having a bulky side chain, e.g., phenylalanine, is substituted for (or by) one not having a side chain, e.g., glycine; or (e) a proline residue is incorporated or substituted, which changes the degree of rotational freedom of the peptidyl bond.

Variants typically exhibit a similar qualitative biological activity and will elicit the same immune response as the naturally-occurring analog, although variants also are selected to modify the characteristics of the skin CS1 proteins as needed. Alternatively, the variant may be designed such that the biological activity of the CS1 protein is altered. For example, glycosylation sites may be altered or removed.

Covalent modifications of CS1 polypeptides are included within the scope of this invention. One type of covalent modification includes reacting targeted amino acid residues of a CS1 polypeptide with an organic derivatizing agent that is capable of reacting with selected side chains or the N- or C-terminal residues of a CS1 polypeptide. Derivatization with bifunctional agents is useful, for instance, for crosslinking CS1 polypeptides to a water-insoluble support matrix or surface for use in a method for purifying anti-CS1 polypeptide antibodies or screening assays, as is more fully described below. Commonly used crosslinking agents include, e.g., 1,1-bis(diazoacetyl)-2-phenylethane, glutaraldehyde, N-hydroxysuccinimide esters, e.g., esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-((p-azidophenyl)dithio) propioimidate.

Other modifications include deamidation of glutaminyl and asparaginyl residues to the corresponding glutamyl and aspartyl residues, respectively, hydroxylation of proline and lysine, phosphorylation of hydroxyl groups of serinyl, threonyl, or tyrosyl residues, methylation of the amino groups of the lysine, arginine, and histidine side chains (e.g., pp. 79-86, Creighton (1992) Proteins: Structure and Molecular Properties Freeman), acetylation of the N-terminal amine, and amidation of a C-terminal carboxyl group.

Another type of covalent modification of the CS1 polypeptide included within the scope of this invention comprises altering the native glycosylation pattern of the polypeptide. "Altering the native glycosylation pattern" is intended for purposes herein to mean deleting one or more carbohydrate moieties found in native sequence CS1 polypeptide, and/or adding one or more glycosylation sites that are not present in the native sequence CS1 polypeptide. Glycosylation patterns can be altered in many ways. Different cell types to express CS1-associated sequences can result in different glycosylation patterns.

Addition of glycosylation sites to CS1 polypeptides may also be accomplished by altering the amino acid sequence thereof. The alteration may be made, e.g., by the addition of, or substitution by, one or more serine or threonine residues to the native sequence CS1 polypeptide (for O-linked glycosylation sites). The CS1 amino acid sequence may optionally be altered through changes at the DNA level, particularly by mutating the DNA encoding the CS1 polypeptide at preselected bases such that codons are generated that will translate into the desired amino acids.

Another means of increasing the number of carbohydrate moieties on the CS1 polypeptide is by chemical or enzymatic coupling of glycosides to the polypeptide. See, e.g., WO 87/05330; pp. 259-306 in Aplin and Wriston (1981) CRC Crit. Rev. Biochem.

Removal of carbohydrate moieties present on the CS1 polypeptide may be accomplished chemically or enzymatically or by mutational substitution of codons encoding for amino acid residues that serve as targets for glycosylation. Chemical deglycosylation techniques are applicable. See, e.g., Sojar and Bahl (1987) Arch. Biochem. Biophys. 259:52-57 and Edge, et al. (1981) Anal. Biochem. 118:131-137. Enzymatic cleavage of carbohydrate moieties on polypeptides can be achieved by the use of a variety of endo- and exo-glycosidases. See, e.g., Thotakura, et al. (1987) Meth. Enzymol. 138:350-359.

Another type of covalent modification of CS1 polypeptides comprises linking the CS1 polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192, or 4,179,337.

CS1 polypeptides of the present invention may also be modified in a way to form chimeric molecules comprising a CS1 polypeptide fused to another heterologous polypeptide or amino acid sequence. In one embodiment, such a chimeric molecule comprises a fusion of a CS1 polypeptide with a tag polypeptide which provides an epitope to which an anti-tag antibody can selectively bind. The epitope tag is generally placed at the amino- or carboxyl-terminus of the CS1 polypeptide. The presence of such epitope-tagged forms of a CS1 polypeptide can be detected using an antibody against the tag polypeptide. Also, provision of the epitope tag enables the CS1 polypeptide to be readily purified by affinity purification using an anti-tag antibody or another type of affinity matrix that binds to the epitope tag. In an alternative embodiment, the chimeric molecule may comprise a fusion of a CS1 polypeptide with an immunoglobulin or a particular region of an immunoglobulin. For a bivalent form of the chimeric molecule, such a fusion could be to the Fc region of an IgG molecule.

Various tag polypeptides and their respective antibodies are available. Examples include poly-histidine (poly-his) or poly-histidine-glycine (poly-his-gly) tags; HIS6 and metal chelation tags, the flu HA tag polypeptide and its antibody 12CA5 (Field, et al. (1988) Mol. Cell. Biol. 8:2159-2165); the c-myc tag and the 8F9, 3C7, 6E10, G4, B7, and 9E10 antibodies thereto (Evan, et al. (1985) Molecular and Cellular Biology 5:3610-3616); and the Herpes Simplex virus glycoprotein D (gD) tag and its antibody (Paborsky, et al. (1990) Protein Engineering 3(6):547-553). Other tag polypeptides include the Flag-peptide (Hopp, et al. (1988) BioTechnology 6:1204-1210); the KT3 epitope peptide (Martin, et al. (1992) Science 255:192-194); tubulin epitope peptide (Skinner, et al. (1991) J. Biol. Chem. 266:15163-15166); and the T7 gene 10 protein peptide tag (Lutz-Freyermuth, et al. (1990) Proc. Natl. Acad. Sci. USA 87:6393-6397).

Also included are CS1 proteins from other organisms, such as chimpanzee, cynos monkey and rhesus monkey, which are cloned and expressed as outlined below. Thus, probe or degenerate polymerase chain reaction (PCR) primer sequences may be used to find other related CS1 proteins from humans or other organisms. Particularly useful probe and/or PCR primer sequences include the unique areas of the CS1 nucleic acid sequence. Preferred PCR primers are from about 15-35 nucleotides in length, with from about 20-30 being preferred, and may contain inosine as needed. The conditions for PCR reaction have been well described (e.g., Innis, PCR Protocols, supra).

Further included are chimeric CS1 proteins constructed to contain amino acid segments from different organisms. For example, chimeric CS1 proteins are constructed by fusing amino acid 1-67 of human CS1 to amino acid 68-224 of mouse CS1, or alternatively fusing amino acid 1-151 of human CS1 to amino acid 149-224 of mouse CS1, or further alternatively fusing amino acid 1-169 of human CS1 to amino acid 167-224 of mouse CS1. Conversely, chimeric CS1 proteins are also constructed by fusing amino acid 1-67 of mouse CS1 to amino acid 68-227 of human CS1, or alternatively fusing amino acid 1-131—of mouse CS1 to amino acid 135-227 of human CS1, or further alternatively fusing amino acid 1-166 of mouse CS1 to amino acid 170-227 of human CS1.

In addition, CS1 proteins can be made that are longer than those encoded by the nucleic acids of the Table 2, e.g., by the elucidation of extended sequences, the addition of epitope or purification tags, the addition of other fusion sequences, etc.

CS1 proteins may also be identified as being encoded by CS1 nucleic acids. Thus, CS1 proteins are encoded by nucleic acids that will hybridize to the sequences of the sequence listings, or their complements, as outlined herein.

Binding Partners to CS1 Proteins
CS1 Antibodies

The CS1 antibodies of the invention specifically bind to CS1 proteins. By "specifically bind" herein is meant that the antibodies bind to the protein with a $K_d$ of at least about 0.1 µM, more usually at least about 1 mM, preferably at least about 0.1 µM or better, and most preferably, 0.01 µM or better. Selectivity of binding to the specific target and not to related sequences is often also important.

In one embodiment, when the CS1 protein is to be used to generate binding partners, e.g., antibodies for immunodiagnosis, the CS1 protein should share at least one epitope or determinant with the full length protein. By "epitope" or "determinant" herein is typically meant a portion of a protein which will generate and/or bind an antibody or T-cell receptor in the context of MHC. Thus, in most instances, antibodies made to a smaller CS1 protein will be able to bind to the full-length protein, particularly linear epitopes. In another embodiment, the epitope is unique; that is, antibodies generated to a unique epitope show little or no cross-reactivity. In yet another embodiment, the epitope is selected from a protein sequence set out in the table.

Methods of preparing polyclonal antibodies exist (e.g., Coligan, supra; and Harlow and Lane, supra). Polyclonal antibodies can be raised in a mammal, e.g., by one or more injections of an immunizing agent and, if desired, an adjuvant. Typically, the immunizing agent and/or adjuvant will be injected in the mammal by multiple subcutaneous or intraperitoneal injections. The immunizing agent may include a protein encoded by a nucleic acid of Table 2 or fragment thereof or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). Various immunization protocols may be used.

The antibodies may, alternatively, be monoclonal antibodies. Monoclonal antibodies may be prepared using hybridoma methods, such as those described by Kohler and Milstein (1975) Nature 256:495. In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro. The immunizing agent will typically include a polypeptide encoded by a nucleic acid of the table or fragment thereof, or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (e.g., pp. 59-103 in Goding (1986) Monoclonal Antibodies: Principles and Practice Academic Press) Immortalized cell lines are usually transformed mammalian cells, particularly cells of rodent, bovine, or human origin. Usually, rat or mouse cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

In one embodiment, the antibodies are bispecific antibodies. Bispecific antibodies are monoclonal, preferably human or humanized, antibodies that have binding specificities for at least two different antigens or that have binding specificities for two epitopes on the same antigen. In one embodiment, one of the binding specificities is for a protein encoded by a nucleic acid of the table or a fragment thereof, the other one is for another antigen, and preferably for a cell-surface protein or receptor or receptor subunit, preferably one that is CS1 specific. Alternatively, tetramer-type technology may create multivalent reagents.

In another embodiment, the antibodies have low levels or lack fucose. Antibodies lacking fucose have been correlated with enhanced ADCC (antibody-dependent cellular cytotoxicity) activity, especially at low doses of antibody. Shields, R. L., et al., (2002) J. Biol. Chem. 277:26733-26740; Shinkawa, T. et al., (2003), J. Biol. Chem. 278:3466. Methods of preparing fucose-less antibodies include growth in rat myeloma YB2/0 cells (ATCC CRL 1662). YB2/0 cells express low levels of FUT8 mRNA, which encodes an enzyme (a 1,6-fucosyltransferase) necessary for fucosylation of polypeptides.

Alternative methods for increasing ADDC activity include mutations in the Fc portion of a CS1 antibody, particularly mutations which increase antibody affinity for an FcγR receptor. A correlation between increased FcγR binding with mutated Fc has been demonstrated using targeted cytoxicity cell-based assays. Shields, R. L. et al. (2001) J. Biol. Chem 276:6591-6604; Presta et al. (2002), Biochem Soc. Trans. 30:487-490. Methods for increasing ADCC activity through specific Fc region mutations include the Fc variants comprising at least one amino acid substitution at a position selected from the group consisting of: 234, 235, 239, 240, 241, 243, 244, 245, 247, 262, 263, 264, 265, 266, 267, 269, 296, 297, 298, 299, 313, 325, 327, 328, 329, 330 and 332, wherein the numbering of the residues in the Fc region is that of the EU index as in Kabat. In a preferred embodiment, said Fc variants comprise at least one substitution selected from the group consisting of L234D, L234E, L234N, L234Q, L234T, L234H, L234Y, L234I, L234V, L234F, L235D, L235S, L235N, L235Q, L235T, L235H, L235Y, L235I, L235V, L235F, S239D, S239E, S239N, S239Q, S239F, S239T, S239H, S239Y, V240I, V240A, V240T, V240M, F241W, F241L, F241Y, F241E, F241R, F243W, F243L, F243Y, F243R, F243Q, P244H, P245A, P247V, P247G, V262I, V262A, V262T, V262E, V263I, V263A, V263T, V263M, V264L, V264I, V264W, V264T, V264R, V264F, V264M, V264Y, V264E, D265G, D265N, D265Q, D265Y, D265F, D265V, D265I, D265L, D265H, D265T, V266I, V266A, V266T, V266M, S267Q, S267L, E269H, E269Y, E269F, E269R, Y296E, Y296Q, Y296D, Y296N, Y296S, Y296T, Y296L, Y296I, Y296H, N297D, N297E, A298H, T299I, T299L, T299A, T299S, T299V, T299H, T299F, T299E, W313F, N325Q, N325L, N325I, N325D, N325E, N325A, N325T, N325V, N325H, A327N, A327L, L328M, L328D, L328E, L328N, L328Q, L328F, L328I, L328V, L328T, L328H, L328A, P329F, A330L, A330Y, A330V, A330I, A330F, A330R, A330H, I332D, I332E, I332N, I332Q, I332T, I332H, I332Y and I332A, wherein the numbering of the residues in the Fc region is that of the EU index as in Kabat. Fc variants may also be selected from the group consisting of V264L, V264I, F241W, F241L, F243W, F243L, F241L/F243L/V262I/V264I, F241W/F243W, F241W/F243W/V262A/V264A, F241L/V262I, F243L/V264I, F243L/V262I/V264W, F241Y/F243Y/V262T/V264T, F241E/F243R/V262E/V264R, F241E/F243Q/V262T/V264E, F241R/F243Q/V262T/V264R, F241E/F243Y/V262T/V264R, L328M, L328E, L328F, I332E, L3238M/I332E, P244H, P245A, P247V, W313F, P244H/P245A/P247V, P247G, V264I/I332E, F241E/F243R/V262E/V264R/I332E, F241E/F243Q/V262T/V264E/I332E, F241R/F243Q/V262T/V264R/I332E, F241E/F243Y/V262T/V264R/I332E, S298A/I332E, S239E/I332E, S239Q/I332E, S239E, D265G, D265N, S239E/D265G, S239E/D265N, S239E/D265Q, Y296E, Y296Q, T299I, A327N, S267Q/A327S, S267L/A327S, A327L, P329F, A330L, A330Y, I332D, N297S, N297D, N297S/I332E, N297D/I332E, N297E/I332E, D265Y/N297D/I332E, D265Y/N297D/T299I/I332E, D265F/N297E/I332E, L328I/I332E, L328Q/I332E, I332N, I332Q, V264T, V264F, V240I, V263I, V266I, T299A, T299S, T299V, N325Q, N325L, N325I, S239D, S239N, S239F, S239D/I332D, S239D/I332E, S239D/I332N, S239D/I332Q, S239E/I332D, S239E/I332N, S239E/I332Q, S239N/I332D, S239N/I332E, S239N/I332N, S239N/I332Q, S239Q/I332D, S239Q/I332N, S239Q/I332Q, Y296D, Y296N, F241Y/F243Y/V262T/V264T/N297D/I332E, A330Y/I332E, V264I/A330Y/I332E, A330L/I332E, V264I/A330L/I332E, L234D, L234E, L234N, L234Q, L234T, L234H, L234Y, L234I, L234V, L234F, L235D, L235S, L235N, L235Q, L235T, L235H, L235Y, L235I, L235V, L235F, S239T, S239H, S239Y, V240A, V240T, V240M, V263A, V263T, V263M, V264M, V264Y, V266A, V266T, V266M, E269H, E269Y, E269F, E269R, Y296S, Y296T, Y296L, Y296I, A298H, T299H, A330V, A330I, A330F, A330R, A330H, N325D, N325E, N325A, N325T, N325V, N325H, L328D/I332E, L328E/I332E, L328N/I332E, L328Q/I332E, L328V/I332E, L328T/I332E, L328H/I332E, L328I/I332E, L328A, I332T, I332H, I332Y, I332A, S239E/V264I/I332E, S239Q/V264I/I332E, S239E/V264I/A330Y/I332E, S239E/V264I/S298A/A330Y/I332E, S239D/N297D/I332E, S239E/N297D/I332E, S239D/D265V/N297D/I332E, S239D/D265V/N297D/I332E, S239D/D265L/N297D/I332E, S239D/D265F/N297D/I332E, S239D/D265Y/N297D/I332E, S239D/D265H/N297D/I332E, S239D/D265T/N297D/I332E, V264E/N297D/I332E, Y296D/N297D/I332E, Y296E/N297D/I332E, Y296N/N297D/I332E, Y296Q/N297D/I332E, Y296H/N297D/I332E, Y296T/N297D/I332E, N297D/T299V/I332E, N297D/T299I/I332E, N297D/T299L/I332E, N297D/T299F/I332E, N297D/T299H/I332E, N297D/T299E/I332E, N297D/A330Y/I332E, N297D/S298A/A330Y/I332E, S239D/A330Y/I332E, S239N/A330Y/I332E, S239D/A330L/I332E, S239N/A330L/I332E, V264I/S298A/I332E, S239D/S298A/I332E, S239N/S298A/I332E, S239D/V264I/I332E, S239D/V264I/S298A/I332E, AND S239D/264I/A330L/I332E, wherein the numbering of the residues in the Fc region is that of the EU index as in Kabat. See also PCT WO 2004/029207, Apr. 8, 2004, incorporated by reference herein.

Antibody-associated ADCC activity can be monitored and quantified through measurement of lactate dehydrogenase (LDH) release in the supernatant, which is rapidly released upon damage to the plasma membrane.

Other alternative embodiments for promoting cytotoxicity of cells with antibody treatment include antibody-mediated stimulation of signaling cascades resulting in cell death to the antibody bound cell. In addition antibody-mediated stimulation of the innate immune system (e.g. through NK cells) may also result in the death of tumor cells or virally-infected cells.

Detection of CS1 Sequence for Diagnostic Applications

In one aspect, the RNA expression levels of genes are determined for different cellular states in the autoimmune disorder or cancerous, e.g. myeloma, phenotype. Expression levels of genes in normal tissue (e.g., not undergoing a disorder) and in diseased tissue (and in some cases, for varying severities of disorders that relate to prognosis, as outlined below) are evaluated to provide expression profiles. A gene expression profile of a particular cell state or point of development is essentially a "fingerprint" of the state of the cell. While two states may have a particular gene similarly expressed, the evaluation of a number of genes simultaneously allows the generation of a gene expression profile that is reflective of the state of the cell. By comparing expression profiles of cells in different states, information regarding which genes are important (including both up- and down-regulation of genes) in each of these states is obtained. Then, diagnosis may be performed or confirmed to determine whether a tissue sample has the gene expression profile of normal or diseased tissue. This will provide for molecular diagnosis of related conditions.

"Differential expression," or grammatical equivalents as used herein, refers to qualitative or quantitative differences in the temporal and/or cellular gene expression patterns within and among cells and tissue. Thus, a differentially expressed gene can qualitatively have its expression altered, including an activation or inactivation, in, e.g., normal versus diseased tissue. Genes may be turned on or turned off in a particular state, relative to another state thus permitting comparison of two or more states. A qualitatively regulated gene will exhibit an expression pattern within a state or cell type which is detectable by standard techniques. Some genes will be expressed in one state or cell type, but not in both. Alternatively, the difference in expression may be quantitative, e.g., in that expression is increased or decreased; e.g., gene expression is either upregulated, resulting in an increased amount of transcript, or downregulated, resulting in a decreased amount of transcript. The degree to which expression differs need only be large enough to quantify via standard characterization techniques as outlined below, such as by use of Affymetrix GENECHIP® (DNA microchip array) expression arrays. See, Lockhart (1996) Nature Biotechnology 14:1675-1680. Other techniques include, but are not limited to, quantitative reverse transcriptase PCR, northern analysis, and RNase protection. As outlined above, preferably the change in expression (e.g., upregulation or downregulation) is at least about 50%, more preferably at least about 100%, more preferably at least about 150%, more preferably at least about 200%, with from 300 to at least 1000% being especially preferred.

Evaluation may be at the gene transcript or the protein level. The amount of gene expression may be monitored using nucleic acid probes to the RNA or DNA equivalent of the gene transcript, and the quantification of gene expression levels, or, alternatively, the final gene product itself (protein) can be monitored, e.g., with antibodies to CS1 protein and standard immunoassays (ELISAs, etc.) or other techniques, including mass spectroscopy assays, 2D gel electrophoresis assays, etc. Proteins corresponding to CS1, e.g., those identified as being important in a disease phenotype, can be evaluated in a disease diagnostic test. In another embodiment, gene expression monitoring is performed simultaneously on a number of genes. Multiple protein expression monitoring can be performed as well.

In this embodiment, the CS1 nucleic acid probes are attached to biochips as outlined herein for the detection and quantification of CS1 sequences in a particular cell. The assays are further described below in the example. PCR techniques can be used to provide greater sensitivity.

In one embodiment nucleic acids encoding CS1 are detected. Although DNA or RNA encoding CS1 protein may be detected, of particular interest are methods wherein an mRNA encoding a CS1 protein is detected. Probes to detect mRNA can be a nucleotide/deoxynucleotide probe that is complementary to and hybridizes with the mRNA and includes, but is not limited to, oligonucleotides, cDNA, or RNA. Probes also should contain a detectable label, as defined herein. In one method the mRNA is detected after immobilizing the nucleic acid to be examined on a solid support such as nylon membranes and hybridizing the probe with the sample. Following washing to remove the non-specifically bound probe, the label is detected. In another method, detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding a myelomaprotein is detected by binding the digoxygenin with an anti-digoxygenin secondary antibody and developed with nitro blue tetrazolium and 5-bromo-4-chloro-3-indoyl phosphate.

In another embodiment, various proteins from the three classes of proteins as described herein (secreted, transmembrane, or intracellular proteins) are used in diagnostic assays. The CS1 proteins, antibodies, nucleic acids, modified proteins, and cells containing CS1 sequences are used in diagnostic assays. This can be performed on an individual gene or corresponding polypeptide level. In one embodiment, the expression profiles are used, preferably in conjunction with high throughput screening techniques to allow monitoring for expression profile genes and/or corresponding polypeptides.

As described and defined herein, CS1 protein finds use as a disease marker of autoimmune disorders, such as SLE, RA, and IBD, and cancerous conditions, such as myeloma and plasma cell leukemia. Additionally, CS1 finds use as a marker for prognostic or diagnostic purposes. Detection of these proteins in putative diseased tissue allows for detection, prognosis, or diagnosis of such conditions, and for selection of therapeutic strategy. In one embodiment, antibodies are used to detect CS1. A preferred method separates proteins from a sample by electrophoresis on a gel (typically a denaturing and reducing protein gel, but may be another type of gel, including isoelectric focusing gels and the like). Following separation of proteins, CS1 is detected, e.g., by immunoblotting with antibodies raised against CS1.

In another method, antibodies to CS1 find use in in situ imaging techniques, e.g., in histology. See, e.g., Asai, et al. (eds. 1993) Methods in Cell Biology: Antibodies in Cell Biology (vol. 37) Academic Press. In this method, cells are contacted with from one to many antibodies to the myeloma protein(s). Following washing to remove non-specific antibody binding, the presence of the antibody or antibodies is detected. In one embodiment the antibody is detected by incubating with a secondary antibody that contains a detectable label. In another method the primary antibody to CS1 contains a detectable label, e.g., an enzyme marker that can act on a substrate. In another embodiment each one of multiple primary antibodies contains a distinct and detectable label. This method finds particular use in simultaneous screening for CS1 along with other markers of the aforementioned conditions. Many other histological imaging techniques are also provided by the invention.

In one embodiment the label is detected in a fluorometer which has the ability to detect and distinguish emissions of different wavelengths. In addition, a fluorescence activated cell sorter (FACS) can be used in the method.

In another embodiment, antibodies find use in diagnosing autoimmune disorders, such as SLE, RA, and IBD, and cancer, such as myeloma and plasma cell leukemia, from blood, serum, plasma, stool, and other samples. Such samples, therefore, are useful as samples to be probed or tested for the presence of CS1. Antibodies can be used to detect CS1 by previously described immunoassay techniques including ELISA, immunoblotting (Western blotting), immunoprecipitation, BIACORE technology and the like. Conversely, the presence of antibodies may indicate an immune response against an endogenous CS1 protein.

In another embodiment, in situ hybridization of labeled CS1 nucleic acid probes to tissue arrays is done. For example, arrays of tissue samples, including diseased tissue and/or normal tissue, are made. In situ hybridization (see, e.g., Ausubel, supra) is then performed. When comparing the fingerprints between an individual and a standard, a diagnosis, a prognosis, or a prediction may be based on the findings. It is further understood that the genes which indicate the diagnosis may differ from those which indicate the prognosis and molecular profiling of the condition of the cells may lead to distinctions between responsive or refractory conditions or may be predictive of outcomes.

In one embodiment, CS1 proteins, antibodies, nucleic acids, modified proteins, and cells containing CS1 sequences are used in prognosis assays. As above, gene expression profiles can be generated that correlate to a disease state, clinical, pathological, or other information, in terms of long term prognosis. Again, this may be done on either a protein or gene level, with the use of genes being preferred. Single or multiple genes may be useful in various combinations. As above, CS1 probes may be attached to biochips for the detection and quantification of CS1 sequences in a tissue or patient. The assays proceed as outlined above for diagnosis. PCR method may provide more sensitive and accurate quantification.

Genes useful in prognostic assays are genes that are differentially expressed according to the stage of illness of the patient. In one embodiment, the genes may be uniquely expressed according to the stage of the patient. In another embodiment, the genes may be expressed at differential levels according to the stage of the patient. For example, in myeloma, patients are accorded three different stages according to the extent and location of the disease: Stages I, II and III. In Stage I, symptoms are mild to non-existent, with many patients showing no symptoms of myeloma. A positive diagnosis is the presence of tumor cells; however, the number of red blood cells is normal or slightly below normal range, there is no detectable increase in calcium in the blood, there are very low levels of M-protein in the blood or urine, and no detectable bone damage can be seen in X-rays. In Stage 11, cancer cells are prevalent in higher numbers. Kidney function may be affected, which worsens the prognostic diagnosis for most patients. Stage III brings about anemia, hypercalcemia, advanced bone damage and high levels of M-protein in the blood and urine. Correlation of protein expression with different stages in autoimmune disorder could also prove useful in determining the prognosis of such disorders. The correlation of genes expressed in the different stages, either uniquely expressed or have differential expression levels according to the stage, may be used to determine the viability of inducing remission in a patient. This would be especially useful in the earlier stages of the disease, where myeloma patients exhibit few symptoms. In addition, genes that are expressed indicating onset of long-term complications, such as beta-2 microglobulin (indicator of kidney damage), as well as high levels of serum albumin and lactate dehydrogenase, may also be useful as a prognostic tool.

The correlation of genes expressed in different stages, either uniquely expressed or having differential expression levels according to the stage, may also be monitored to determine the efficacy of treatment using the therapeutics disclosed in the present invention. For example, patients treated with antagonists of the present invention may be monitored for therapeutic efficacy of said antagonists through the monitoring of markers, including for example, CS1 or CS1 in combination with disorder-specific markers (e.g. the monitoring of M-protein for myeloma treatment. Monitoring of these specific markers will be important in determining the efficacy of therapeutic invention, as well as determining dosage and method of treatment considerations for the different indications of the present invention.

Induction of Disease Disorders as Model Systems In Vivo
Inflammatory Bowel Disease Experimental in vivo models have been developed for the investigation of pathological processes of inflammatory bowel disease. Sartor R B, Aliment. Pharmacol. Ther. 11:89-96 (1997). For example, knock-out transgenic mice can be made, in which the inflammatory bowel disease gene is disrupted or in which an inflammatory bowel disease gene is inserted. Knock-out transgenic mice can be made by insertion of a marker gene or other heterologous gene into the endogenous inflammatory bowel disease gene site in the mouse genome via homologous recombination. Such mice can also be made by substituting the endogenous inflammatory bowel disease gene with a mutated version of the inflammatory bowel disease gene, or by mutating the endogenous inflammatory bowel disease gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi, et al. (1989) Science 244:1288-1292). Chimeric targeted mice can be derived according to Hogan, et al. (1988) Manipulating the Mouse Embryo: A Laboratory Manual CSH Press; and Robertson (ed. 1987) Teratocarcinomas and Embryonic Stem Cells: A Practical Approach IRL Press, Washington, D.C.

Other models can be constructed using non-genetic manipulation of animal models. One model in particular has been used extensively in small molecule screening. This model induces colitis in rats or mice by a single intracolonic challenge with a solution of the hapten 2, 4, -trinitrobenzene sulfonic acid (TNBS). Morris G P et al., Gastroenterology 96:795-803 (1989); Boughton-Smith N K, Br. J. Pharmacol. 94:65-72 (1988). Treatment with TNBS produces an intense local inflammatory response that reaches its nadir after 2 to 3 days, and can last up to 21 days, depending on the severity of the challenge.

The inflammatory response produced by TNBS treatment is considered to reproduce many of the macroscopic, histological, and immunological hallmarks of Crohn's disease. Grisham M B et al., Gastroenterology 101:540-547 (1991); Yamada Y et al., Gastroenterology 102:524-534 (1992); Torres M I et al., Dig. Dis. Sci 44:2523-29 (1999); Neruath M, Fuss I, Strober W, Int. Rev. Immunol. 19:51-62 (2000). Open ulceration is observed, with transmural inflammation and thickening of the bowel wall. Histological features include distorted crypt architecture, crypt atrophy, granulomata, giant cells, basal lymphoid aggregates, and the presence of an inflammatory infiltrate.

The model has been used to study and validate colonic inflammation, and address aspects of inflammatory bowel disease. Hoffman P et al., Gut 41:195-202 (1997); Jacobson K, McHugh K, Collins S M, Gastroenterology 112:156-62 (1997).

Other animal models include HLA-B27 transgenic rats (Hammer R E et al., Spontaneous inflammatory disease in transgenic rats expressing HLA-B27 and Human b2M: An animal model of HLA-B27 associated human disorders, *Cell*

63:1088-1112 (1990)), transgenic IL-2 deficient mice (Baumgart D C et al., Mechansisms of intestinal epithelial cell injury and colitis in interleukin 2 deficient mice, *Cell Immunol.* 187:52-66 (1998)), mdrla deficient mice (Panwala C M et al., A Novel Model of Inflammatory Bowel Disease: Mice deficient for the multiple drug resistance gene, mdrla, spontaneously develop colitis, J. Immunol. 161:5733-44 (1998)), and IL 10 deficient mice (Freeman H J, Studies on the interleukin-10 gene in animal models of colitis, Canadian Gastroenterology (2003)).

Myeloma

Experimental in vivo models have been developed for the investigation of pathological processes of myeloma. Sartor R B, Aliment. Pharmacol. Ther. 11:89-96 (1997). For example, knock-out transgenic mice can be made, in which the myeloma gene is disrupted or in which a myeloma gene is inserted. Knock-out transgenic mice can be made by insertion of a marker gene or other heterologous gene into the endogenous myeloma gene site in the mouse genome via homologous recombination. Such mice can also be made by substituting the endogenous myeloma gene with a mutated version of the myeloma gene, or by mutating the endogenous myeloma gene, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi, et al. (1989) Science 244:1288-1292). Chimeric targeted mice can be derived according to Hogan, et al. (1988) Manipulating the Mouse Embryo: A Laboratory Manual CSH Press; and Robertson (ed. 1987) Teratocarcinomas and Embryonic Stem Cells: A Practical Approach IRL Press, Washington, D.C.

Other models can be constructed using non-genetic manipulation of animal models. For example, injecting C57BL/6J mice with B-cell tumors (e.g. LLC cells) can induce lung metastasis. Other animal models utilize SCID mice and inject B-cell tumor lines (e.g. HsSultan cells (ATCC) or multiple myeloma lines, (for example but not limited to, L363, LP-1, OPM-2, or RPMI 8226) to induce myeloma-like characteristics. Still other animal models include an NOD/SCID mouse model for human multiple myeloma generated by implanting human fetal bones (FBs) into subcutaneous sites of NOD/SCID mice, followed by inoculation with primary bone marrow mononuclear cells obtained from patients with multiple myeloma into the FBs. See Shang-Yi H., et al., Amer. J. Invest. Pathol. 164:747-756 (2004). Mouse plasmacytoma models, whose formation is induced through pristane oil (2,6, 10, 12-tetramethylpentadecane) treatment may also be used. In addition, mouse models in which injection of myeloma cells directly into the bone marrow (orthotopic injection model) of SCID, SCID/beige or NOD/SCID mice, may also be used.

Cells undergoing transformation, as in myeloma cells, release an increased amount of certain factors (hereinafter "myeloma specific markers") than their normal counterparts. For example, CD38, CD9, CD10, HLA-DR, and CD20 are increased in expression in myeloma cells. Ruiz-Arugelles G J and San Miguel J F, Cell Surface Markers in Multiple Myeloma, Mayo Clin. Proc. 69:684-90 (1994).

Various techniques which measure the release of these factors are described in Freshney (1998), supra. Also, see, Unkeless, et al. (1974) J. Biol. Chem. 249:4295-4305; Strickland and Beers (1976) J. Biol. Chem. 251:5694-5702; Whur, et al. (1980) Br. J. Cancer 42:305-312; Gullino "Angiogenesis, tumor vascularization, and potential interference with tumor growth" pp. 178-184 in Mihich (ed. 1985) Biological Responses in Cancer Plenum; Freshney (1985) Cancer Res. 5:111-130.

Therapeutic Methods

Autoimmune Disease Treatment

In one aspect, the present invention is directed to a method of reducing the proliferation, adhesion, differentiation, activation and/or co-activation of leukocytes, comprising contacting the leukocytes with an antagonist of CS1 described herein.

In another aspect, the present invention is directed to a method of reducing the secretion (or production) of immunoglobulin by lymphocytes (such as B cells), comprising contacting the lymphocytes with an antagonist of CS1 described herein. Antagonists of the present invention can reduce the production of immunoglobulin (such as, IgM, IgG, IgD, IgA, and IgE) by at least 5%, 10%, 20%, 30%, 40%, or 50%. The percentage change is calculated by subtracting the immunoglobulin concentration prior to the administration of the first dose of the antibody (day 0) from the immunoglobulin concentration post dose (day x), dividing by the immunoglobulin concentration prior to the first dose (day 0), and multiplying by 100, e.g., [(day x−day 0)/day 0]×100.

In yet another aspect, the present invention is directed to a method of inducing apoptosis or cytolysis of cells expressing CS1 comprising contacting the cells with an antibody against CS1 described herein. In a preferred embodiment, the induction is achieved via antibody-dependent cellular cytotoxicity (ADCC). In general, antibodies of the present invention bind antigens on the surface of target cells (cells that express CS1) in the presence of effector cells (such as natural killer cells or macrophages). Fc receptors on effector cells recognize bound antibodies. The cross-linking of Fc receptors signals the effector cells to kill the target cells by cytolysis or apoptosis. Cytolysis can be detected via detection of either the release of label or lactate dehydrogenase from the lysed cells, or detection of reduced target cell viability (e.g. annexin assay). Assays for apoptosis may be performed by terminal deoxy-nucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.). Preferably, the antibodies of the present invention induce at least 10%, 20%, 30%, 40%, 50%, 60%, or 80% cytotoxicity of the target cells. The percentage is calculated by the methods disclosed in the Examples.

The antagonists can make contact with the leukocytes in vitro (such as, by adding the antagonists into a cell culture environment where the leukocytes are cultivated), ex vivo, or in vivo (for example, by administering the antagonists into a subject).

In a preferred embodiment, the leukocytes are a) activated lymphocytes, such as B cells and/or T cells, preferably $CD19^+$ B cells and/or $CD3^+$ T cells; b) $CD14^+$ activated and/or naïve cells; c) activated and/or unactivated dendritic cells; and/or c) $CD56^+$ NK and/or NKT cells.

In a preferred aspect, the present invention provides for a method of reducing the secretion of immunoglobulin by B cells, in a subject in need thereof, comprising administering an effective amount of an antagonist of CS1 into said subject.

In another preferred aspect the present invention provides for a method of inducing cytotoxicity, cytolysis, and/or apoptosis of cells expressing CS1 in a subject in need thereof, comprising administering an effective amount of an antibody of CS1 into said subject.

The antagonists, preferably antibodies of the present invention, can be used for the prevention or treatment of autoimmune diseases, including, but not limited to, Addison's disease, autoimmune diseases of the ear, autoimmune diseases of the eye such as uveitis, autoimmune hepatitis, Crohn's disease, diabetes (Type I), epididymitis, glomerulonephritis, Graves' disease, Guillain-Barre syndrome, Hashimoto's disease, hemolytic anemia, systemic lupus erythematosus (SLE), multiple sclerosis, myasthenia gravis, pemphigus vulgaris, psoriasis, rheumatoid arthritis, sarcoidosis, scleroderma, psoriasis, Sjogren's syndrome, spondyloarthropathies, thyroiditis, ulcerative colitis and/or vasculitis.

In a preferred embodiment, the autoimmune disease that can be prevented and/or treated with the methods of the present invention is SLE, RA, or IBD. After being administered into a subject who has developed the symptoms of SLE, RA, or IBD, the anti-CS1 antibodies should be able to reduce the severity of the symptoms. Alternatively, the anti-CS1 antibodies can be administered to a subject before the subject developed any clinical manifestations of SLE, RA, or IBD. Such a preventive administration of the antibodies should completely prevent the subject from developing any SLE, RA, or IBD symptoms or at least prevent the subject from developing as severe symptoms as in the condition without the antibody treatment. The severity of symptoms of SLE, RA, or IBD can be measured by the standard clinical test for SLE, RA, or IBD known in the art, such as serum level of anti-DNA antibodies, proteinuria, and the mortality rate of the patients.

Therapeutic methods are usually applied to human patients but may be applied to other mammals.

Cancer Treatment

Therapeutic methods for reducing the proliferation of myeloma cells is also included, comprising contacting myeloma cells with an antagonist of a myeloma protein, preferably an antibody or other antagonist, such as the CS1 antibodies described herein. For example, the antibodies can make contact with myeloma cells in vitro (such as, by adding the antagonists into a cell culture environment where the myeloma cells are cultivated), ex vivo, or in vivo (for example, by administering the antagonists into a subject). In another aspect, the present invention provides for a method of reducing the proliferation of myeloma cells, comprising administering an effective amount of a myeloma protein antagonist into said subject.

In one aspect, the antagonists, preferably antibodies of the present invention, can be used for the prevention or treatment of myeloma. After being administered into a subject who has developed the symptoms of myeloma, the antibodies or antagonist should be able to reduce the severity of the symptoms. Alternatively, the antibodies of the present invention can be administered to a subject before the subject developed any clinical manifestations of myeloma. The severity of symptoms of myeloma can be measured by the standard clinical test for myeloma known in the art, such as bone-density X-ray analysis, beta-2 microglobulin levels or hypercalcemia. Therapeutic methods are usually applied to human patients but may be applied to other mammals.

In yet another aspect, the present invention is directed to a method of inducing apoptosis or cytolysis of cells expressing CS1 comprising contacting the cells with an antibody against CS1 described herein. In a preferred embodiment, the induction is achieved via antibody-dependent cellular cytotoxicity (ADCC). In general, antibodies of the present invention bind antigens on the surface of target cells (cells that express CS1) in the presence of effector cells (such as natural killer cells or macrophages). Fc receptors on effector cells recognize bound antibodies. The cross-linking of Fc receptors signals the effector cells to kill the target cells by cytolysis or apoptosis. Cytolysis can be detected via detection of either the release of label or lactate dehydrogenase from the lysed cells, or detection of reduced target cell viability (e.g. annexin assay). Assays for apoptosis may be performed by terminal deoxynucleotidyl transferase-mediated digoxigenin-11-dUTP nick end labeling (TUNEL) assay (Lazebnik et al., Nature: 371, 346 (1994). Cytotoxicity may also be detected directly by detection kits known in the art, such as Cytotoxicity Detection Kit from Roche Applied Science (Indianapolis, Ind.). Preferably, the antibodies of the present invention induce at least 10%, 20%, 30%, 40%, 50%, 60%, or 80% cytotoxicity of the target cells. The percentage is calculated by the methods disclosed in the Examples.

The antagonists can also make contact with leukocytes in vitro (such as, by adding the antagonists into a cell culture environment where the leukocytes are cultivated), ex vivo, or in vivo (for example, by administering the antagonists into a subject).

In a preferred embodiment, the leukocytes are a) activated lymphocytes, such as B cells and/or T cells, preferably $CD19^+$ B cells and/or $CD3^+$ T cells; b) $CD14^+$ activated and/or naïve cells; c) activated and/or unactivated dendritic cells; and/or c) $CD56^+$ NK and/or NKT cells.

In a preferred aspect, the present invention provides for a method of reducing the secretion of immunoglobulin by B cells, in a subject in need thereof, comprising administering an effective amount of an antagonist of CS1 into said subject. Such reduction of immunoglobulin secretion by B cells may help relieve complications of myeloma, including hyperviscocity syndrome.

In another preferred aspect the present invention provides for a method of inducing cytotoxicity, cytolysis, and/or apoptosis of cells expressing CS1 in a subject in need thereof, comprising administering an effective amount of an antibody of CS1 into said subject.

Administration of Therapeutic Agents

There are various methods of administering the antagonists, for example, antibodies of the present invention. Parenteral administration is preferred. The antibody may be administered to a patient intravenously as a bolus or by continuous infusion over a period of time; or by intramuscular, subcutaneous, intraperitoneal, or infra-cerebrospinal routes. Oral, topical, inhalation routes, or other delivery means known to those skilled in the art are also included in the present invention.

The pharmaceutical compositions of the present invention commonly comprise a solution of antagonists (for example, antibodies), or a cocktail thereof dissolved in an acceptable carrier, preferably an aqueous carrier. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc. to make isotonic. The carrier can also contain excipients such as human serum albumin, polysorbate 80, sugars or amino acids to protect the active protein. The concentration of an antagonist (for example, antibody) in these formulations varies widely from about 0.1 to 100 mg/ml but is often in the range 1 to 10 mg/ml. The formulated monoclonal antibody is particularly suitable for parenteral administration, and can be administered as an intravenous infusion or by subcutaneous, intramuscular or intravenous injection. Actual methods for preparing parentally administrable compositions are known or apparent to those skilled in the art and are described in more detail in, for example, Remington's Pharmaceutical Science (15th Ed., Mack Publishing Company, Easton, Pa., 1980), which is incorporated herein by reference. The present invention provides for a pharmaceutical composition comprising any one of the antibodies described herein.

The compositions can be administered for prophylactic and/or therapeutic treatments, comprising inhibiting the interactions between a CS1 and its cellular substrate, inhibiting the adhesion of diseased cells, or preventing and/or reducing the clinical symptoms of the disorders above. An amount adequate to accomplish any one of these desired effects is defined as an "effective amount". The antibodies can be delivered into a patient by single or multiple administrations.

For the purpose of treatment of disease, the appropriate dosage of the antagonists (for example, antibodies) will depend on the severity and course of disease, the patient's clinical history and response, the toxicity of the antibodies, and the discretion of the attending physician. The antagonists are suitably administered to the patient at one time or over a series of treatments. The initial candidate dosage may be administered to a patient. The proper dosage and treatment regimen can be established by monitoring the progress of therapy using conventional techniques known to the people skilled of the art.

Additionally, the antagonist (such as antibodies) can be utilized alone in substantially pure form, or together with therapeutic agents for autoimmune diseases known to those of skill in the art. Other therapies that may be used in conjunction with treatment with the antibodies include administration of anti-sense nucleic acid molecules or biologicals, such as additional therapeutic antibodies. Thus, the treatment of the present invention is formulated in a manner allowing it to be administered serially or in combination with another agent for the treatment of autoimmune diseases. For treating autoimmune disorders and myeloma, the antibody will often be administered after or in combination with one or more other immunosuppressive drugs and immunomodulators.

Kits for Use in Diagnostic and/or Prognostic Applications

For use in diagnostic and research applications suggested above, kits are also provided by the invention. In diagnostic and research applications, such kits may include at least one of the following: assay reagents, buffers, CS1-specific nucleic acids or antibodies, hybridization probes and/or primers, antisense polynucleotides, ribozymes, dominant negative CS1 polypeptides or polynucleotides, small molecule inhibitors of CS1-associated sequences etc.

In addition, the kits may include instructional materials containing instructions (e.g., protocols) for the practice of the methods of this invention. While the instructional materials typically comprise written or printed materials, they are not limited to such. A medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include addresses to internet sites that provide such instructional materials.

The present invention also provides for kits for screening for modulators of CS1-associated sequences. Such kits can be prepared from readily available materials and reagents. For example, such kits can comprise one or more of the following materials: a CS1-associated polypeptide or polynucleotide, reaction tubes, and instructions for testing CS1-associated activity. Optionally, the kit contains biologically active CS1 protein. A wide variety of kits and components can be prepared according to the present invention, depending upon the intended user of the kit and the particular needs of the user. Diagnosis would typically involve evaluation of a plurality of genes or products. The genes will typically be selected based on correlations with important parameters in disease which may be identified in historical or outcome data.

EXAMPLES

Example 1

Isolation and Identification of CS1

CS1 was identified from a cDNA subtraction library of B-cell subsets (naïve vs. memory+plasma B cells) from normal healthy adult peripheral blood. CS1 was preferentially expressed among the memory and plasma B cells. Subtraction libraries were produced by following the protocol described below:

Isolation of B-Cell Subsets:

Peripheral blood mononuclear cells (PBMCs) were isolated from nine healthy adult donors with standard Ficoll-hypaque gradients. B cells were isolated from the PBMCs by following a standard negative selection protocol. PBMCs were incubated in an antibody cocktail of purified mouse anti-human CD2, CD3, CD4, CD14, CD16, CD56, CD66 and glycophorin A. After incubation and washing, goat-anti-mouse magnetic Dynal beads were added at 7-10 beads per cell. Subsequently, the antibody-bound cells were isolated with a standard Dynal magnetic holder to leave enriched B cells in the supernatants. The collected supernatants were then washed with RPMI+10% fetal bovine serum (FBS).

Sorting of B-Cell Subsets (Naïve vs. Memory+Plasma B Cells):

Dynal-enriched B cells were stained with IgD-FITC, CD38-cychrome, CD19-APC, and CD27-PE by following the standard staining protocols. The two separate populations of naïve B cells ($IgD^+$ $CD19^+$ $CD38^{int/-}$ $CD27^-$) versus memory and plasma B cells ($IgD^+$ $CD19^+$ $CD38^{int/-}$ $CD27^+$) were sorted on a MoFlo High Performance Flow cytometer-MLS, which is equipped with a spectra physics air-cooled argon laser (488 nm) and a 635-nm diode laser and with filters for detection of FITC at 530/40 nm, PE at 580/30 nm, APC at 670/20 nm, and cychrome (PE-Cy5) at 670/30 nm. The sorted B cells were analyzed on the MoFlo cytometer for purity and were found to be of 97% (memory and plasma B cells) and 98% (naïve B cells) purity. The sorted cells were placed in Trizol and stored at −70° C.

cDNA Library Production:

The cDNA subtraction libraries were made from the sorted B cell subsets by using a standard representational difference analysis subtractive hybridization protocol. The subtraction libraries included the memory+plasma B cell cDNA library, where the naïve cDNA was subtracted twice, and the naïve B cell cDNA library, where the memory+plasma cDNA was subtracted twice. With standard molecular biology techniques, the cDNA subtraction library was ligated into a standard plasmid vector and transformed into electrocompetent E. coli (DH-10B) cells. The transformed E. coli cells were plated on LB agar plates in the presence of selection antibiotics. Single bacterial colonies, each representing one specific insert, were amplified using standard colony PCR.

Screening and Confirming Differential Expression:

The cDNA subtraction library inserts were denatured and blotted onto 2 identical nylon filters and hybridized separately with two different labeled, denatured probes—(memory+plasma)—naïve cDNA (subtracted twice) and naïve—(memory+plasma) cDNA (subtracted twice). A subtraction library cDNA insert was considered positive if the insert selectively hybridized preferentially with one of the two probes. The cDNA clones for CS1 hybridized preferentially with the (memory+plasma)—naïve cDNA probe (twice subtracted).

Identification of CS1:

Bacterial cells transformed with positive clones were grown and DNA was isolated with a Qiagen® Mini-Prep kit (in vitro diagnostic preparations) following the manufacturer's protocol (Qiagen, Valencia, Calif.). The purified plasmids were sequenced and the identity of the DNA sequence was determined by searching NCBI databases.

Characterization and Confirmation of CS1 Gene Expression:

Preferential expression of the selected positive clones, including CS1, was confirmed by dot blot analysis. Equal amounts of (unsubtracted) cDNA (20 ng) isolated from sorted native versus memory+plasma B cells were spotted on nylon filters and hybridized with labeled cDNA insert for the positive clone. For these assays, cDNA was synthesized from peripheral blood B cell subsets obtained from 2 separate sorts (n=9 healthy adults and n=10 healthy adults, purity >97% and >98%, respectively). Filters were washed and signal from hybridized probes was detected by autoradiography. A clone was considered positive if cDNA hybridized preferentially to the memory+plasma B cell cDNA across both sets of sorted naïve versus memory+plasma B cells. The data indicated that CS1 is expressed predominantly in plasma and memory B cells.

CS1 is Expressed Primarily in Lymphoid Tissue:

Dot blots were prepared from cDNA synthesized from polyA+ RNA, which was purchased from Clontech (Palo Alto, Calif.) and made from the following tissues: spleen, lymph node, bone marrow, small intestine, brain, lung, skeletal muscle, heart, kidney, and liver. Dot blots were probed with digoxygenin (DIG) labeled CS1 DNA and visualized by chemiluminescence (alkaline phosphatase labeled anti-DIG antibody and CDP-Star) following the manufacturer's recommendations (Boehringer-Mannheim DIG kit). The results indicate that CS1 is expressed primarily in lymphoid tissues (spleen, lymph node, bone marrow and small intestine-possibly due to residual lymphocytes in Peyer's patches) and is absent or low in other non-lymphoid organs (brain, lung, skeletal muscle, heart, kidney, and liver).

Example 2

Differential Expression of CS1

Human Cells:

Peripheral blood mononuclear cells (PBMCs) were obtained by isolation from standard Ficoll-hypaque gradients. Isolated PBMCs were then resuspended at 2×106 cells/ml in a fresh culture medium. PBMCs were stimulated with phytohemagglutinin (PHA) at a concentration of 3 µg/ml for 3 days, or with pokeweed mitogen (PWM) at a concentration of 10 µg/ml for 8 days. Unstimulated control PBMCs were prepared without any stimulus. Cells were cultured at 37° C. in 7% CO2 in RPMI medium with 10% FBS, penicillin, streptomycin, and glucose additives.

Mouse Cells:

Spleens were obtained from two Balb/c mice. The spleens were placed on 100 micron filter. Cells were disaggregated and washed with PBS, and centrifuged at 1,500 rpm for 10 minutes. Red blood cells were lysed with 2 ml of lysis buffer at 37° C. for 2 minutes. Cells were washed twice, resuspended in 10 ml of the medium and counted. A portion of the unstimulated cells was frozen directly. The remaining cells were stimulated with conA at a concentration of 5 µg/ml for 3 days, or with LPS at a concentration of 1 µg/ml for 3 days. Cells were cultured in a DMEM medium with 10% FBS, antibiotics, and glucose additives.

B Lymphocytes from Lupus Patient Versus Age-Matched Healthy Individuals:

B cells were sorted from peripheral blood mononuclear cells of lupus patient and healthy individuals, by staining the cells with FITC-labeled anti-human CD19 antibody. Cells were sorted on a MoFLo High Performance Flow Cytometer-MLS as described in Example 1. Cells were collected into sterile medium for RNA synthesis.

Total RNA Isolation for Real-Time PCR:

Cells were washed once and placed in Trizol™ (Life Technologies, Gaithersburg, Md.), and total RNA was isolated following the manufacturer's protocol. Total RNA was treated with RNase-free DNase (GenHunter, Nashville, Tenn.). DNase-digested RNA was extracted with phenol/chloroform and precipitated overnight with ethanol. RNA was washed with 75% ethanol and dissolved in nuclease-free water. The isolated RNA was quantitated and its integrity was analyzed on an agarose gel.

Real-Time PCR:

Total RNA (2 µg) was reverse-transcribed from the lupus patient's versus healthy individuals' sorted B lymphocytes in 100 µl of reaction mixture by using standard Taqman reverse transcription reagents (Applied Biosystems, Foster City, Calif.). PCR reactions were set up using SYBR green PCR master mix from Applied Biosystems. CS1 primers were incorporated in the mix to examine the expression levels of CS1 in lupus patient's and healthy individuals' cDNA. CS1 primers were designed from the published sequences (Genbank accession number XM-001635, AF390894). (β-Actin and 18S rRNA primers were used as controls for normalization. The primers were designed using Primer Express software purchased from Applied Biosystems. The PCR amplified products were 85 bp for CS1 primers, 84 bp for β-actin primers, and 61 bp for 18S rRNA primers. Real-Time PCR was performed in a GeneAmp 5700 SDS system from Applied Biosystems, using the recommended protocol.

Real-Time PCR of Mouse Novel Ly9:

Total RNA (2 µg) was reverse transcribed from conA, LPS, and unstimulated samples in 100 µl of reaction mixture using standard Taqman reverse transcription reagents (Applied Biosystems). A PCR reaction was set up using SYBR green PCR master mix from Applied Biosystems. Primers specific for mouse novel Ly9 were designed from the published sequence (Genbank accession number AF467909) and incorporated in the mix to examine the expression levels in stimulated vs. unstimulated cDNA samples. The 18S rRNA primers were used for normalization. The primers were designed by using Primer Express software purchased from Applied Biosystems. The PCR amplified products were 65 bp for the mouse Ly9 primers and 61 bp for the 18S rRNA primers. Real-Time PCR was performed in a GeneAmp 5700 Sequence Detection System from Applied Biosystems, using the recommended protocol.

Microarray Assays: Sample Preparation, Labeling Microchips and Fingerprints

Expression profiles of activated and non-activated leukocytes populations were determined and analyzed using gene chips. The custom Affymetrix GeneChip® oligonucleotide microarray allows interrogation of approximately 35,000 unique mRNA transcripts.

RNA was isolated and gene chip analysis was performed as described (See Henshall et al. (2003) Cancer Research 63:4196-4203; Henshall et al. (2003) Oncogene 22:6005-12; Glynne, et al. (2000) Nature 403:672-676; Zhao, et al. (2000) Genes Dev. 14:981-993, herein incorporated in its entirety).

Purify Poly A+ mRNA from Total RNA or Clean Up Total RNA with Qiagen's RNEASY® (Purification of Poly A+ mRNA from Total RNA) Kit The oligotex suspension was heated to 37° C. and mixed immediately before adding to RNA. The Elution Buffer was incubated at 70° C. Note that the 2× Binding Buffer may be warmed up at 65° C. if there is precipitate in the buffer. Total RNA was mixed with DEPC-treated water, 2× Binding Buffer, and Oligotex according to Table 2 on page 16 of the Oligotex Handbook. The mixture was incubated for 3 minutes at 65° C., and then incubated for 10 minutes at room temperature.

The tubes were centrifuged for 2 minutes at 14,000 to 18,000 g. Note that if the centrifuge has a "soft setting," it should be used. The supernatant was removed without disturbing the Oligotex pellet. A small amount of solution may be left behind to reduce the loss of Oligotex. The supernatant should be saved until certain that satisfactory binding and elution of poly A+ mRNA has occurred.

The pellet was gently resuspended in Wash Buffer OW2 and pipetted onto the spin column. The spin column was centrifuged at full speed (soft setting if possible) for 1 minute.

After centrifugation, the spin column was transferred to a new collection tube and gently resuspended in Wash Buffer OW2 and re-centrifuged as describe herein.

The spin column was transferred to a new tube and eluted with 20 to 100 µl of preheated (70° C.) Elution Buffer. The Oligotex resin was gently resuspended by pipetting up and down, and then centrifuged as above. The elution procedure was repeated with fresh elution buffer. Otherwise if low elution volume is necessary, the first eluate only may be used.

The absorbance was read, using diluted Elution Buffer as the blank.

Ethanol Precipitation

Before proceeding with cDNA synthesis, the mRNA was precipitated.

Some component leftover or in the Elution Buffer from the Oligotex purification procedure will inhibit downstream enzymatic reactions of the mRNA.

0.4 vol. of 7.5 M $NH_4OAc$+2.5 vol. of cold 100% ethanol was added to the eluate. The solution was precipitated at −20° C. 1 hour to overnight (or 20-30 min. at −70° C.). The precipitated solution was centrifuged at 14,000-16,000×g for 30 minutes at 4° C. The pellet was washed with 0.5 ml of 80% ethanol (−20° C.) then centrifuged at 14,000-16,000×g for 5 minutes at room temperature. The 80% ethanol wash was repeated 1×. The pellet was dried in the hood. (Do not speed vacuum). The pellet was suspended in DEPC $H_2O$ at 1 µg/µl concentration.

Cleaning Up Total RNA Using Qiagen's RNeasy Kit

No more than 100 µg RNA should be added to an RNeasy column. The sample volume was adjusted to 100 µl with RNase-free water, and 350 µl Buffer RLT then 250 µl ethanol (100%) was added to the sample. The solution was mixed by pipetting (do not centrifuge) then the sample applied to an RNeasy mini spin column. The mini spin column was centrifuged for 15 sec at >10,000 rpm. If concerned about yield, the flowthrough can be reapplied to the column and centrifuged again.

The column was transferred to a new 2-ml collection tube and 500 µl of Buffer RPE was added and centrifuged for 15 sec at >10,000 rpm. The flowthrough was discarded. 500 µl Buffer RPE was added to the mini-spin column again, and centrifuged for 15 sec at >10,000 rpm. The flowthrough was again discarded, then centrifuged for 2 min at maximum speed to dry column membrane. The column was transferred to a new 1.5-ml collection tube and 30-50 µl of RNase-free water was applied directly onto column membrane. The column was centrifuged for 1 min at >10,000 rpm, and the elution repeated.

An absorbance reading was taken. If necessary, the eluate may be precipitated with ammonium acetate and 2.5× volume 100% ethanol.

Making cDNA using Gibco's "SUPERSCRIPT® Choice System for cDNA Synthesis" kit

First Strand cDNA Synthesis

5 µg of total RNA or 1ug of polyA+ mRNA was used as starting material. For total RNA, 2 µl of SUPERSCRIPT® RT (kit with reverse transcriptase for cDNA synthesis) was used (for polyA+ mRNA, use 1 µl of SUPERSCRIPT® RT). The final volume of the first strand synthesis mix should be 20 µl. RNA must be in a volume no greater than 10 µl. The RNA was incubated with 1 µl of 100 µmol T7-T24 oligo for 10 min at 70 C. On ice, 7 µl of: 4 µl 5×$1^{st}$ Strand Buffer, 2 µl of 0.1M DTT, and 1 µl of 10 mM dNTP mix was added. The mixture was incubated at 37 C for 2 min, then SUPERSCRIPT® RT was added.

The mixture was incubated at 37° C. for 1 hour.

Second Strand Synthesis

The 1st strand reactions were placed on ice.

To the Mixture was Added:

91 µl DEPC H2O
30 µl 5×$2^{nd}$ Strand Buffer
3 µl 10 mM dNTP mix
1 µl 10 U/µl *E. coli* DNA Ligase
4 µl 10 U/µl *E. coli* DNA Polymerase
1 µl 2 U/µl RNase H The above should be made into a mix if there are more than 2 samples. The added mixture was incubated for 2 hours at 16 C.

2 µl T4 DNA Polymerase was added and further incubated for 5 min at 16 C. 10 µl of 0.5M EDTA was added to stop the reaction.

Clean Up cDNA

The cDNA was cleaned up using Phenol:Chloroform:Isoamyl Alcohol (25:24:1) purification in gel tubes:

The PLG (phase lock gel) tubes were centrifuged for 30 sec at maximum speed, and transferred to a new PLG tube. An equal volume of phenol:chloroform:isamyl alcohol was added and shaken vigorously (do not vortex). The tubes were centrifuged for 5 minutes at maximum speed. The top aqueous layer solution was transferred to a new tube. The aqueous solution was ethanol precipitated by adding 7.5×5M NH4Oac and 2.5× volume of 100% ethanol. The tubes were centrifuged immediately at room temp. for 20 min, maximum speed. The supernatant was removed and the pellet washed 2× with cold 80% ethanol. Remove as much ethanol wash as possible then let pellet air dry. The pellet was resuspended in 3 µl RNase-free water.

In Vitro Transcription (IVT) and Labeling with Biotin 1.5 µl of cDNA was pipetted into a thin-wall PCR tube. NTP labeling mix was added at room temperature to the PCR tube.

NTP Labeling Mix:

2 µl T7 10×ATP (75 mM) (Ambion)
2 µl T7 10×GTP (75 mM) (Ambion)
1.5 µl T7 10×CTP (75 mM) (Ambion)
1.5 µl T7 10×UTP (75 mM) (Ambion)
3.75 µl 10 mM Bio-11-CTP
0.75 µl 10 mM Bio-16-UTP
2 µl 10× T7 transcription buffer (Ambion)
2 µl 10× T7 enzyme mix (Ambion)

The final volume of the total reaction was 20 µl. The tubes were incubated for 6 hours at 37° C. in a PCR machine.

RNeasy Clean-Up of IVT Product

See above for procedure.

The labeled cRNA is ethanol precipitated and resuspended in a volume compatible with the fragmentation step.

Fragmentation

Approximately 15 ug of labeled RNA was fragmented using the following technique. The fragmentation reaction volume was minimized to approximately 10 µl volume, but not more than 20 µl due to magnesium precipitation problems with the hybridization buffer.

The RNA was fragmented by incubating at 94° C. for 35 minutes in 1× Fragmentation buffer.

5× Fragmentation buffer:
200 mM Tris-acetate, pH 8.1
500 mM KOAc
150 mM MgOAc

The labeled RNA transcript was analyzed before and after fragmentation. Samples were heated to 65° C. for 15 minutes and electrophoresed on 1% agarose/TBE gels to get an approximate idea of the transcript size range.

Microchip Array

The EOS HuO3 microchip array used in all experiments is a customized Affymetrix GENECHIP® oligonucleotide array comprising 59,680 probesets representing 46,000 unique sequences including both known and FGENESH predicted exons that were based on the first draft of the human genome. The HuO3 probesets consist of perfect match probes only, most probesets having 6 or 7 probes.

Hybridization On Microchip Array

200 µl (Mug cRNA) of hybridization mix was pipetted onto the chip. If multiple hybridizations are to be done (such as cycling through a 5 chip set), then it is recommended that an initial hybridization mix of 300 µl or more be made.

Hybridization Mix: Fragmented Labeled RNA (50 ng/µl Final Conc)
50 pM 948-b control oligo
1.5 pM BioB
5 pM BioC
25 pM BioD
100 pM CRE
0.1 mg/ml herring sperm DNA
0.5 mg/ml acetylated BSA
to 300 µl with 1×MES hybridization buffer Hybridization signals were visualized using phycoerythrin-conjugated streptavidin.

Normalization of the Gene Expression Data

The gene expression data was normalized by fitting the probe-level intensity data from each array to a fixed γ-distribution, using an inverse γ function to map the empirical cumulative distribution of intensities to the desired γ distribution. This procedure is akin to other per-chip normalization procedures, such as fixing the mean and SD of each chip to a standard value, except it is more stringent in that it fixes the entire distribution of intensities rather than one or two parameters. The purpose of per-chip normalization is to remove between-chip variations, on the assumption that it is attributable to nonbiological factors, i.e. technical noise. The scale parameter for the distribution was chosen to yield a distribution with an arbitrary mean value of 300, and the shape parameter of 0.81 was chosen to reproduce the typical shape of the empirical distribution seen in good samples.

A single measure of average intensity was calculated for each probeset using Tukey's trimean of the intensity of the constituent probes. The trimean is a measure of central tendency that is resistant to the effects of outliers. Finally, a background subtraction was applied to each average intensity measure to correct for nonspecific hybridization. The average intensity measure of a "null" probeset consisting of 491 probesets with scrambled sequence was subtracted from all of the other probesets on the chip.

The instruction manuals for the products used herein are incorporated herein in their entirety.

Labeling Protocol Provided Herein

Hybridization Reaction:
Start with non-biotinylated IVT (purified by RNeasy columns)
(see example 1 for steps from tissue to IVT)
IVT antisense RNA; 4 µg: µl
Random Hexamers (1 µg/µl): 4 µl
$H_2O$: µl
Total Volume: 14 µl
Incubate 70° C., 10 min. Put on ice.

Reverse Transcription:
5× First Strand (BRL) buffer: 6 µl
0.1 M DTT: 3 µl
50× dNTP mix: 0.6 µl
$H_2O$: 2.4 µl
Cy3 or Cy5 dUTP (1 mM): 3 µl
SS RT II (B): 1 µl
Total volume: 16 µl
Add to hybridization reaction.
Incubate 30 min., 42° C.
Add 1 µl SSII and let go for another hour.
Put on ice.
50× dNTP mix (25 mM of cold dATP, dCTP, and dGTP, 10 mM of dTTP: 25 µl each of 100 mM dATP, dCTP, and dGTP; 10 µl of 100 mM dTTP to 15 µl H2O)

RNA degradation:
Add 1.5 µl 1 M NaOH/2 mM EDTA, incubate at 65° C., 10 min.
H2O 86 µl
10N NaOH 10 µl
50 mM EDTA 4 µl
U-Con 30
500 µl TE/sample spin at 7000 g for 10 min, save flow through for purification Qiagen Purification:
suspend u-con recovered material in 500 µl buffer PB
proceed w/ normal Qiagen protocol DNAse Digest:
Add 1 µl of 1/100 dil of DNAse/30 µl Rx and incubate at 37° C. for 15 min.
5 min 95° C. to denature enzyme Sample Preparation:
Add:
Cot-1 DNA: 10 µl
50× dNTPs: 1 µl
20×SSC: 2.3 µl
Na pyro phosphate: 7.5 µl
10 mg/ml Herring sperm DNA 1 µl of 1/10 dilution
Final Volume: 21.8 µl
Dry down in speed vac.
Resuspend in 15 µl $H_2O$.
Add 0.38 µl 10% SDS.
Heat 95° C., 2 min.
Slow cool at room temp. for 20 min.
Put on slide and hybridize overnight at 64° C.

Washing after the Hybridization:
3×SSC/0.03% SDS: 2 min 37.5 mls 20×SSC+0.75 mls 10% SDS in 250 mls $H_2O$
1×SSC: 5 min 12.5 mls 20×SSC in 250 mls $H_2O$
0.2×SSC: 5 min. 2.5 mls 20×SSC in 250 mls $H_2O$
Dry slides in centrifuge, 1000 RPM, 1 min.

Scan at appropriate Photomultiplier Tube settings and fluorescence channels.

CS1 is Over-Expressed in Leukocytes but not in Various Types of Nonlymphoid Tissues To evaluate the expression profile of CS1, mRNA isolated from leukocytes and other tissues was analyzed by real-time PCR. The results indicate that the mRNA expression level was much higher in leukocytes than that of most other normal adult tissues. Other normal adult tissues that did not show CS1 expression above baseline levels included adipose, adrenal gland, aorta, aortic valve, appendix, coronary artery, bladder, bone, bone marrow, breast, bronchus, cervix, brain, spinal cord, diaphragm, endometrium, epididymis, esophagus, gallbladder, ganglion, heart, larynx, lip, liver, lung, muscle, myometrium, vagus nerve, omentum, oral mucosa, ovary, pancreas, parathyroid, pharyngeal mucosa, placenta, prostate, retina, salivary gland, skin, stomach, synovium, testis, thymus, thyroid, tongue, trachea, umbilical cord, ureter, uterus, vagina, or vein. CS1 mRNA was expressed in selected samples of colon (2/11), kidney (1/20), small intestine (1/3), spleen, and tonsil (2/4). The results indicated that CS1 is primarily expressed in leukocytes and should be a good target for autoimmune diseases.

CS1 Expression Increases in Multiple Activated Leukocyte Populations

To evaluate the correlation between the CS1 expression and activation of leukocytes, CS1 mRNA expression was analyzed in multiple activated and non-activated leukocytes populations. The results indicate that CS1 expression increased in activated B cells, mature DC cells, activated CD3 cells (low to moderate increase), activated CD4 cells (low level increase), and activated CD8 cells (low to moderate increase, depending on donor) in comparison to their corresponding non-activated control populations. These results indicated that CS1 over-expression correlates with the activation of several leukocyte subsets.

Example 3

Production of Antigens for Generating Monoclonal Antibodies Against CS1 Cloning

The extracellular domain (ECD) of human CS1 was isolated from Raji cells using primers flanking the extracellular domain of CS1 (CS1 ECD). The PCR product was gel purified and ligated into a vector encoding the constant region of IgG3 (human Fc-γ3). The plasmid containing CS1 ECD-Fcγ3 was purified on a large scale and confirmed by DNA sequencing.

CS1 ECD-Fcγ3 Stable Transfection:

50 µg of CS1 ECD-Fcγ3 plasmid was linearized with Fsp1 enzyme, and the DNA was precipitated in ethanol, washed, and resuspended in 500 µl of sterile PBS. NSO cells were washed twice in cold PBS, and resuspended at $2 \times 10^7$ per one ml of PBS. An amount of $1 \times 10^7$ cells was used for transfection.

500 µl of NSO cells were combined with 500 µl of DNA in PBS. Cells were electroporated at 1.5V and 3 µF by a BioRad Gene pulses. Cells were added to 100 ml of DMEM complete media and plated into ten 96-well plates. Mycophenolic selection media at 1 µg/ml was added 24 hours after the transfection. Positive transfectants were screened after day 10 and expanded into 48- and 24-well plates. Positive transfectants were re-screened and high producers were expanded for protein purification.

Purification of CS1 ECD-Fcγ3 Protein:

Stable transfectants expressing the CS1-ECD Fcγ3 fusion protein were expanded into 600 ml of DMEM complete media with glucose additives for five days. The fusion protein was purified on a protein G Sepharose column and dialyzed against 1×PBS. Reduced and non-reduced forms of CS1 ECD-Fcγ3 were analyzed by Coomassie. CS1 ECD Fcγ3 was also analyzed by Western blot using anti-HuIgG, and confirmed by N-terminal sequencing. The purified CS1-Fc-γ3 fusion protein was used to immunize mice.

Production of CS1 ECD-myc-GPI Fusion Protein:

The extracellular domain (ECD) of human CS1 was isolated from Raji cells using primers flanking the extracellular domain of CS1. The PCR product was gel-purified and litigated into a vector expressing a myc tag and glycosyl phosphatidylinositol linkage for cell surface expression (myc-GPI vector). The plasmid containing CS1 ECD-myc-GPI was purified on a large scale and confirmed by DNA sequencing.

CS1 ECD-myc-GPI Stable Transfection:

50 µl of CS1 ECD-myc-GPI plasmid was linearized with Fsp1 enzyme, and the DNA was precipitated in ethanol, washed, and resuspended in 500 µl of sterile PBS. NSO cells were washed twice in cold PBS and resuspended at $2 \times 10^8$ per one ml of PBS. An amount of $1 \times 10^8$ cells was used for transfection.

500 µl of NSO cells were combined with 500 µl of DNA in PBS. Cells were electroporated at 1.5 V and 3 µF by a Biorad Gene pulser. Cells were grown in at 37° C. in 5% $CO_2$ with 1 µg/ml of mycophenolic selection, and were later subcloned into 96-well plates. Positive transfectants were screened with anti-myc antibody. High producers of CS1 ECD-myc-GPI transfectants were selected and expanded for in vitro assays.

Example 3

Production of Anti-CS1 Monoclonal Antibodies

Immunogens for Human CS1:

The purified recombinant human CS1 ECD-γ3 fusion protein was used to immunize Balb/c mice via footpads (CS1 ECD refers to the extracellular domain of CS1 described above). Briefly, mice were immunized in the hind footpads with 10 µg protein with an equal volume of Ribi adjuvant in a total volume of 25 µl. Footpad immunizations were performed 4 times at 4- or 5-day intervals.

a. Cell Fusion:

Two mice immunized with CS1 ECD-γ3 were sacrificed. The popliteal femoral and sacral lymph nodes were removed from the mice. Lymphocytes were isolated from the tissues, and hybridomas were generated by standard procedures. Briefly, hybridomas were generated by polyethylene glycol (PEG) 1500 mediated fusion between lymphocytes and a murine myeloma cell line (NSO cells). Fused cells were plated into 96-well plates at a density of $10^7$ cells per plate. Selection of fused cells was accomplished using HAT (hypoxanthine, aminopterin, thymidine) media.

b. Screening of Hybridomas

Specificity of antibodies secreted by hybridomas was determined by a flow cytometry (FACS) based binding assay to CS1 expressing cells. FACS assay was performed using standard protocols. NSO stable transfectants expressing surface CS1 extracellular domain ($2 \times 10^5$) were resuspended in 50 µl ice cold PBS with 50 µl hybridoma culture supernatant on ice for 1 hour. After extensive washing, cells were incubated with phycoerythrin-conjugated goat anti-mouse IgG specific antibodies for 1 hour on ice. Cells were washed again and cell-surface-bound antibodies were detected by FACS using a Becton Dickinson FACScan. As shown in Table 1, the antibodies: Luc2, Luc3, Luc15, Luc20, Luc22, Luc23, Luc29, Luc32, Luc34, Luc35, Luc37, Luc38, Luc39, Luc56, Luc60, Luc63, or Luc90, bound strongly to the NSO-CS1 cells transfected with CS1, but not to NSO-FcRn. Anti-human CS1 antibodies bound to K562 and Daudi cells (which are known to express native CS1) but not to negative control Jurkat cells. The data show that the produced anti-CS1 antibodies are capable of binding specifically to CS1. Also shown in the table were results from assaying (by ELISA) binding of Luc antibodies to CS1-γ3 fusion protein versus negative control AR-G3 (γ3 fusion protein). Luc antibodies bound specifically to CS1-γ3 and not to the negative control AR-γ3 fusion protein.

TABLE 1

Anti-human CS1 MABs generated from fusion 342

| | | FACS (MFI) | | | | Elisa (capture) | | | |
|---|---|---|---|---|---|---|---|---|---|
| Results | | | | | | | | | |
| MAB | NSO-CS1 | NSO-FcRn | K562 | Daudi | Jurkat | CS1-G3 | AR-G3 | Subclones | Mouse Ig ISO |
| 1 Luc2 | 162 | <5 | 13.4 | 10.5 | <5 | 1.0 | 0.2 | Luc2-1 | IgG1 |
| 2 Luc3 | 377 | <5 | 25.7 | 7.8 | <5 | 0.9 | 0.5 | Luc3-F | IgG1, G2b |
| 3 Luc15 | 110 | <5 | 14.0 | 12.4 | <5 | 1.1 | 0.3 | Luc15-1 | ND |
| 4 Luc20 | 89 | <5 | 8.0 | 12.6 | <5 | 1.2 | 0.2 | Luc20-1 | ND |
| 5 Luc22 | 228 | <5 | 14.7 | 6.1 | <5 | 0.6 | 0.2 | Luc22-1 | IgG2b |
| 6 Luc23 | 164 | <5 | 19.6 | 10.2 | <5 | 0.6 | 0.2 | Luc23-1 | IgG1 |
| 7 Luc29 | 86 | <5 | 24.1 | 11.9 | <5 | 0.9 | 0.2 | Luc29-D6, C8 | IgG1 |
| 8 Luc32 | 201 | <5 | 9.8 | 10.7 | <5 | 0.8 | 0.2 | Luc32-1 | IgG2b |
| 9 Luc34 | 127 | <5 | 26.2 | 10.3 | <5 | 1.2 | 0.3 | Luc34-1, 34-3 | IgG1 |
| 10 Luc35 | 184 | <5 | 10.6 | 29.7 | <5 | 0.7 | 0.2 | Luc35-1 | IgG2a |
| 11 Luc37 | 366 | <5 | 12.8 | 7.2 | <5 | 0.6 | 0.2 | Luc37-C12, F11 | IgG2b |
| 12 Luc38 | 112 | <5 | 31.4 | 11.6 | <5 | 0.8 | 0.2 | Luc38-1 | IgG2b |
| 13 Luc39 | 117 | <5 | 12.0 | 17.5 | <5 | 0.4 | 0.2 | Luc39-E10 | IgG2a |
| 14 Luc56 | 132 | <5 | 12.6 | 9.7 | <5 | 1.0 | 0.2 | Luc56-1 | IgG2a |
| 15 Luc60 | 230 | <5 | 14.6 | 10.4 | <5 | 0.9 | 0.3 | Luc60-2 | IgG2b |
| 16 Luc63 | 214 | <5 | 15.8 | 12.7 | <5 | 0.6 | 0.2 | Luc63-1 | IgG2a |
| 17 Luc90 | 237 | <5 | 9.7 | 10.1 | <5 | 0.8 | 0.1 | Luc90-H1, D9 | IgG2b |
| ISO control | 14 | 3 | 5.41 | 6.02 | <5 | 0.16 | 0.14 | | |
| Anti-Myc | 193 | 335 | 6.62 | 6.85 | <5 | 0.19 | 0.15 | | |

The Amino Acid Sequences of the Produced Anti-CS1 Monoclonal Antibodies

Antibody heavy and light chain variable regions were cloned using standard techniques. Briefly, total RNA from $1-5 \times 10^6$ cells was used to prepare cDNA using a SMART RACE cDNA Amplification Kit (BD Biosciences Clontech) and variable regions were PCR amplified using gene specific primers complementary to the mouse heavy and light chain constant regions.

The amino acid sequences of the mature heavy chain and the mature light chain of the antibodies Luc90, Luc63, and Luc34 are shown in Table 4 which provides amino acid sequences of the heavy chain variable region (SEQ ID NO: 3) and light chain variable region (SEQ ID NO: 4) of Luc90; the amino acid sequences of the heavy chain variable region (SEQ ID NO: 5) and light chain variable region (SEQ ID NO: 6) of Luc63; and the amino acid sequences of the heavy chain variable region (SEQ ID NO: 7) and light chain variable region (SEQ ID NO: 8) of Luc34. SEQ ID NOS: 9, 10 and 11 depict the amino acid sequences of the Luc90 heavy chain CDR1, CDR2, and CDR3, respectively. SEQ ID NOS: 12, 13, and 14 depict the amino acid sequences of the Luc90 light chain CDR1, CDR2, and CDR3, respectively. SEQ ID NOS: 15, 16, and 17 depict the amino acid sequences of the Luc63 heavy chain CDR1, CDR2, and CDR3, respectively. SEQ ID NOS: 18, 19, and 20, depict the amino acid sequences of the Luc63 light chain CDR1, CDR2, and CDR3, respectively. SEQ ID NOS: 21, 22, and 23, depict the amino acid sequences of the Luc34 heavy chain CDR1, CDR2, and CDR3, respectively. SEQ ID NOS: 24, 25, and 26 depict the amino acid sequences of the Luc34 light chain CDR1, CDR2, and CDR3, respectively.

TABLE 4

Amino Acid Sequences of CS1 Antibodies

Luc-90 VH-
SEQ ID NO: 3

QVQLQQPGAELVRPGASVKLSCKASGYSFT<u>TYWMN</u>WVKQRPGQGLEWIG<u>MIHPSDSETRLNQ</u>
            SEQ ID NO: 9     SEQ ID NO: 10

KFKDKATLTVDKSSTAYMQLSSPTSEDSAVYYCAR<u>STMIATRAMDY</u>WGQGTSVTVSS
                SEQ ID NO: 11

Luc-90 VL-
SEQ ID NO: 4

DIVMTQSQKSMSTSVGDRVSITC<u>KASQDVITGVA</u>WYQQKPGQSPKLLIY<u>SASYRYT</u>GVPDRF
         SEQ ID NO: 12      SEQ ID NO: 13

TGSGSGTDFTFTISNVQAEDLAVYYC<u>QQHYSTPLT</u>FGAGTKLELK
           SEQ ID NO: 14

Luc-63 VH-
SEQ ID NO: 5

EVKLLESGGGLVQPGGSLKLSCAASGFDFS<u>RYWMS</u>WVRQAPGKGLEWTG<u>EINPDSSTINYTP</u>
            SEQ ID NO: 15     SEQ ID NO: 16

<u>SLKDKFIISRDNAKNTLYLQMSKVRSEDTALYYCARPDGNYWYFDV</u>WGAGTTVTVSS
                SEQ ID NO: 17

TABLE 4-continued

Amino Acid Sequences of CS1 Antibodies

```
Luc-63 VL-
                                                         SEQ ID NO: 6
DIVMTQSHKPMSTSVGDRVSITCKASQDVGIAVAWYQQKPGQSPKLLIYWASTRHTGVPDRF
                 SEQ ID NO: 18          SEQ ID NO: 19

TGSGSGTDFTLTISNVQSEDLADYFCQQYSSYPYTFGGGTKLEIK
                         SEQ ID NO: 20

Luc-34 VH-
                                                         SEQ ID NO: 7
QVQLQQSGAELARPGASVKLSCKASGYTFTSYWMQWVKQRPGQGLEWIGAIYPGDGDTRYTQ
                    SEQ ID NO: 21           SEQ ID NO: 22

KFKGKATLTADKSSSTAYMQLSSLASEDSAVYYCARGKVYYGSNPFAYWGQGTLVTVSA
                                      SEQ ID NO: 23

Luc-34 VL-
                                                         SEQ ID NO: 8
DIQMTQSSSYLSVSLGGRVTITCKASDHINNWLAWYQQKPGNAPRLLISGATSLETGVPSRF
                   SEQ ID NO: 24           SEQ ID NO: 25

SGSGSGKDYTLSITSLQTEDVATYYCQQYWSTPWTFGGGTKLEIK
                       SEQ ID NO: 26
```

Example 4

Characterization of CS1 Antibodies

A flow cytometry competition assay was used to determine the epitope specificity of 15 different anti-CS1 monoclonal antibodies. NSO stable transfectants expressing surface CS1 ($2\times10^5$) were incubated on ice for 1 hour with 50 μl anti-CS1 antibodies, including pairwise combinations of Luc23, Luc29 Luc34, Luc35, Luc37, Luc38, Luc 63, and Luc 90. In parallel, isotype control antibody (AIP-13) was used as a negative control. Biotinylated anti-CS1 monoclonal antibodies (Luc23, Luc34, Luc37, Luc38, Luc63, and Luc90) were incubated at 1 μg/ml with the cell/antibody mixture for additional 30 minutes on ice. After extensive washing, cells were incubated with phycoerythrin-conjugated streptavidin for 1 hour on ice. Cells were washed and cell surface-bound biotinylated antibodies were detected by FACS using a Becton Dickinson FACScan.

The unlabeled antibodies: Luc23, Luc34, Luc37, Luc38, Luc63, and Luc90 were tested for the ability to compete with each other at a concentration of 15 μg/ml, 3 μg/ml, and 0.6 μg/ml and the competing or blocking antibodies were added at 1 μg/ml. AIP-13 was used as a negative control, since this antibody does not bind CS1 or compete with any of the Luc antibodies. A significant decrease in the MFI indicated competition for cell surface CS1 by biotinylated anti-CS1 by Mab versus unlabeled anti-CS1 Mab, by at least 50% compared to the MFI of the control antibody.

The competition assays indicated that several of the Luc antibodies contact distinct epitopes. Luc38 contacts an epitope distinct from the Luc37, 23, 90, and 63 epitopes. Luc63 contacts a separate, non-overlapping epitope that is distinct from the Luc37, 23, 90, and 38 epitopes. Luc90 contacts a different, non-overlapping epitope, distinct from the Luc 37, 23, 63, and 38 epitopes. Luc 23 contacts another non-overlapping epitope, distinct from the Luc90, 63, and 38 epitopes. Luc37 contacts an additional non-overlapping epitope, distinct from the epitopes contacted by Luc90, 63, and 38. Luc63 contacts an overlapping epitope with Luc34, while Luc90 contacts an overlapping epitope with Luc34. Luc37 contacts an epitope that overlaps with the epitope of Luc23. Luc34 blocks or significantly decreases binding of all Luc antibodies, and may either contact a broad, exposed epitope or may have higher affinity for CS1. Luc37, Luc23, and Luc38 do not block binding to CS1 by the Luc34 antibody. Epitopes for Luc37, Luc23, and Luc38 may be "buried" within the CS1 secondary structure, or the affinity for CS1 may be lower than the affinity of the Luc34 antibody.

The relative affinities of three monoclonal antibodies were also tested by Biacore analysis. Kinetic Analysis of CS1 MAbs by SPRKinetics measurements between human CS1-Fc fusion protein and anti-human CS1 monoclonal mouse antibodies Luc34.1, 63.2, and 90H1 were performed using BIAcore 2000 (BIAcore, Sweden). Regeneration condition was established by immobilizing over 10 000 RUs of each antibody onto different flow cells and injecting CS1-Fc over the surface, followed by testing a series of different buffers until the best one was found to optimize the clearance of CS1-Fc from each antibody. A buffer of 10 mM Glycine, pH2.0 was found to be the optimal regeneration buffer and was immediately tested for its reproducibility over 10 cycles of CS1-Fc injection and buffer regeneration. The buffer was found to be suitable for regenerating the antibody surface reproducibly. Hence 10 mM Glycine, pH2.0 was the designated regeneration buffer for the CS1-Fc and antibody BIAcore experiments.

CS1 antibody produced in-house was immobilized with low response units (RUs) ranging from 99.4 RUs to 133.7 RUs on the Research-grade CM5 sensor chip by the BIAcore amine coupling reagents (N-ethyl-N'-dimethylaminopropyl-carbodiimide, EDC; N-hydroxysuccinimide, NHS; and ethanolamine HCl, pH 8.5). Assays were run at a flow rate of 30 ul/min at room temperature. A three-minute association phase of CS1-Fc was followed by ten-minute injection of running buffer (10 mM Hepes, 300 mM sodium chloride, 3 mM EDTA, 0.05% P-20, pH7.4) to monitor dissociation for each binding cycle, with different CS1-Fc concentrations per cycle. The regeneration surface was regenerated with 10 mM Glycine, pH2.0. The binding kinetics of each CS1-Fc and antibody pair was calculated from a global analysis of sensorgram data collected from twelve different concentrations of CS1-Fc (1024 nM, 512 nM, 256 nM, 128 nM, 64 nM, 32 nM, 16 nM, 8 nM, 4 nM, 2 nM, 1 nM, 0.5 nM) in duplicate, using the BIAevaluate program. Double referencing was applied in each analysis to eliminate background responses from reference surface and buffer only control. The affinity ($K_D$) of binding was obtained by simultaneously fitting the association and dissociation phases of the sensorgram from the analyte concentration series using the bivalent analyte model from BIAevaluate software. The experiment was performed three times to study the standard deviation of the data.

The binding affinities of Luc 90.H1, Luc63.2, and Luc34.1 are summarized below. Luc90.H1 has highest binding affinity among these three antibodies. The binding affinity of Luc90.H1 is 5.5 fold higher than that of Luc 63.2 and 28 fold higher than that of Luc34.1.

|  | Ka (1/Ms) | Kd (1/s) | KD (M) |
| --- | --- | --- | --- |
| Luc 90.H1 | 4.56e4 | 2.81e−4 | 6.29e−9 +/− 2.06e−9 |
| Luc63.2 | 8.71e3 | 3.01e−4 | 3.46e−8 +/− 8.86e−9 |
| Luc34.1 | 7.48e3 | 1.27e−3 | 1.73e−7 +/− 3.46e−8 |

Immunohistological Staining with Anti-CS1 Antibodies:

The CS1-transfected cells were also examined for immunohistological staining with anti-CS1 antibodies. An amount of 10 µg/ml of primary monoclonal anti-CS1 antibody was added to the cells transfected with CS1. The cells were then blocked with serum and incubated with the biotin-anti-mouse-Ig. Avidin-peroxidase was then mixed with the cells and developed with AEC (a standard peroxidase reagent). The red color of AEC indicated the positive staining while the nuclei of the tested cells were counter-stained with hematoxylin (blue). The data indicated that CS1-transfected cells were positively stained with the anti-CS1 antibodies Luc 23, Luc 38 and Luc 63, showing that the produced anti-CS1 antibodies are capable of binding to CS1 expressed on the cell surface. Thus, the anti-CS1 antibodies are suitable for use not only in detecting expression on the surface of peripheral blood cells in solution, but also in detecting by immunohistochemistry (IHC), which is typically used to analyze tissue sections (for example, patient lymph nodes or tissue biopsies).

Immunohistological staining of inflamed tonsil was illustrated with two anti-CS1 antibodies, Luc90 and Luc63, Staining with CD138 stains plasma cells and epithelial cells. From the overlapping pattern of the staining, it is evident that CS1 antibodies stain plasma cells in inflamed tonsil.

Immunohistological staining of synovial tissue from the joint of a patient with rheumatoid arthritis was demonstrated with anti-CS1 Luc63. Plasma cells have infiltrated in the synovium as seen by the staining with CD138. From the overlapping pattern of the staining, it is evident that anti-CS1 antibodies stain plasma cells in the joints of patients with rheumatoid arthritis.

These results indicate that plasma cells expressing CS1 were present in both inflamed tonsil and the joints of patients with rheumatoid arthritis, suggesting viable use of anti-CS1 antibodies in the treatment of these diseases.

CS1 Protein Expression Pattern:

The CS1 protein expression was further examined with the produced Luc antibodies through FACS analysis. PBMCs were isolated from healthy individuals and from lupus patients by a standard Ficoll Hypaque gradient centrifugation procedure. PBMCs were stained with antibodies as indicated following standard procedures. For pokeweed mitogen (PWM) activation of PBMCs, PWM was added at 1:100 dilution to PBMCs, which were subsequently placed at 37° C. in 7% $CO_2$ for 8 days. PWM-stimulated cells were harvested and washed prior to antibody staining. The mouse anti-CS1 antibodies used herein are Luc90 ($IgG_2b$), Luc63, Luc38 and other produced anti-CS1 Luc antibodies. Isotype control antibodies were isotype matched mouse IgG antibodies.

The results indicated that CS1 was positively expressed on activated B cells, $CD8^+$ T cells (both activated and naïve), NK cells ($CD3^-CD56^+$), NKT cells ($CD56^+$ $CD3^+$), $CD14^{+/lo}$ leukocytes (monocytes and/or macrophages), and $CD4^+$ T cells (low level on in vitro activated cells). CS1 was expressed on these cell populations from both healthy adults and lupus patients. No significant CS1 protein expression was detected on unactivated $CD4^+$ T cells from healthy adults, platelets, HuVECs, kidney cells, bronchial airway cells, small airway cells, prostate cells, liver cells, and breast cells.

Staining of activated B cells is shown by staining of PWM-activated PBMCs, while isotype control staining and unactivated PBMCs was shown as the background fluoroescense. The CS1 expression pattern is significant, because a therapeutic antibody ideally binds primarily to target cells and does not bind to other cells and tissues, especially platelets. The data suggest anti-CS1 antibodies are suitable candidate therapeutic antibodies.

Example 5

Humanization of CS1 Antibodies

This example describes the humanization of the murine anti-CS1 monoclonal antibody Luc63 (MuLuc63). Humanization of MuLuc63 was carried out essentially according to the procedure of Queen, C. et al. (Proc. Natl. Acad. Sci. USA 86: 10029-10033 (1989)). First, human VH and VL segments with high homology to the MuLuc63 VH and VL amino acid sequences, respectively, were identified. Next, the CDR sequences together with framework amino acids important for maintaining the structures of the CDRs were grafted into the selected human framework sequences. The resulting humanized monoclonal antibody (HuLuc63) was expressed in the mouse myeloma cell line NS0. The humanized HuLuc63 antibody bound to recombinant human CS1 in an ELISA assay with an EC50 value of 70.1 ng/ml, similar to the EC50 value of 66.1 ng/ml determined for MuLuc63 in the same assay, indicating that HuLuc63 retained high binding affinity for human CS1.

Cloning and Sequencing of MuLuc63 Variable Region cDNAs

Total RNA was extracted from approximately $5 \times 10^7$ hybridoma cells producing MuLuc63 using TRIzol reagent (Life Technologies, Inc., Rockville, Md.). Double-stranded cDNA was synthesized using the SMART RACE cDNA Amplification Kit (BD Biosciences Clontech, Palo Alto, Calif.) following the supplier's protocol. The variable region cDNAs for the heavy and light chains were amplified by polymerase chain reaction (PCR) using 3' primers that anneal respectively to the mouse gamma and kappa chain C regions, and a 5' universal primer provided in the SMART RACE cDNA Amplification Kit. For VH PCR, the 3' primer has the sequence 5'-AGCTGGGAAGGTGTGCACAC-3' (SEQ ID NO:85). For VL PCR, the 3' primer has the sequence 5'-TTCACTGC-CATCAATCTTCC-3' (SEQ ID NO:86). The VH and VL cDNAs were subcloned into the pCR4Blunt-TOPO vector (Invitrogen Corporation, Carlsbad, Calif.) for sequence determination. DNA sequencing was carried out by PCR cycle sequencing reactions with fluorescent dideoxy chain terminators (Applied Biosystems, Foster City, Calif.) according to the manufacturer's instructions.

Four plasmid clones were sequenced for each of the heavy and light chains. Unique sequences homologous to typical mouse heavy and light chain variable regions were identified. The cDNA sequences along with deduced amino acid sequences of the heavy and light chain V regions of MuLuc63 are shown in Tables 5 and 6.

Table 5 provides amino acid sequences of the heavy chain variable region (SEQ ID NO:27) and light chain variable region (SEQ ID NO:28) of Luc 63, including respective signal peptide sequences (SEQ ID NOS:29 and 34). SEQ ID NOS:30-32 and 35-37 depict CDR's of the heavy chain and light chain variable region, respectively. SEQ ID NO:33 depicts the single amino acid mutation, from NYT to NYA (italicized), in CDR2 of the heavy chain variable region of Luc 63.

TABLE 5

Anti-CS1 Luc63 Variable Heavy Chain Region Putative Glycosylation Site (SEQ ID NO: 27)
Luc-63 VH
MDFGLIFFIVALLKGVQCEVKLLESGGGLVQPGGSLKLSCAASGFDFSRYWMSWVRQAPGKG
   SEQ ID NO: 29                              SEQ ID NO: 30
LEWIGEINPDSSTTNYTPSLKDKFIISRDNAKNTLYLQMSKVRSEDTALYYCARPDGNYWYF
      SEQ ID NO: 31                             SEQ ID NO: 32
DVWGAGTTVTVSS

NYA (SEQ ID NO: 33)

(SEQ ID NO: 28)
Luc-63 VL
METHSQVFVYMLLWLSGVEGDIVMTQSHKFMSTSVGDRVSITCKASQDVGIAV
SEQ ID NO: 34                             SEQ ID NO: 35
AWYQQKPGQSPKLLIYWASTRHTGVPDRFTGSGSGTDFTLTISNVQSEDLADYF
               SEQ ID NO: 36
CQQYSSYPYTFGGGTKLEIK
SEQ ID NO: 37

Table 6 provides amino acid sequences of the mouse Luc 63 heavy chain variable region (SEQ ID NO:38), human heavy chain variable region framework sequence (SEQ ID NO:39), human JH1 cDNA (SEQ ID NO:40) and humanized Luc 63 heavy chain variable region (SEQ ID NO:41). Also provided are amino acid sequences of the mouse light chain variable region (SEQ ID NO:42), human light chain variable region framework (SEQ ID NO:43) and humanized Luc 63 light chain variable region (SEQ ID NO:44).

TABLE 6

| Luc63 (NYA) Humanization | |
|---|---|
| MuLuc-63 VH | EVKLLESGGGLVQPGGSLKLSCAASGFDFS RYWMS |
| HumanVH cDNA | EVQLVESGGGLVQPGGSLRLSCAASGFTFS |
| HuLuc-63 VH | EVQLVESGGGLVQPGGSLRLSCAASGFDFS RYWMS |
| MuLuc-63 VH | WVRQAPGKGLEWIG EINPDSSTINYTPSLKD |
| HumanVH cDNA | WVRQAPGKGLEWVA |
| HuLuc-63 VH | WVRQAPGKGLEWIG EINPDSSTINYAPSLKD |
| MuLuc-63 VH | KFIISRDNAKNTLYLQMSKVRSEDTALYYCAR |
| Human JH1 cDNA | RFTISRDNAKNSLYLQMNSLRAEDTAVYYCAR |
| HuLuc-63 VH | KFIISRDNAKNSLYLQMNSLRAEDTAVYYCAR |

TABLE 6-continued

| Luc63 (NYA) Humanization | |
|---|---|
| MuLuc-63 VH | PDGNYWYFDV WGAGTTVTVSS |
| Human JH1 cDNA | |
| HuLuc-63 VH | PDGNYWYFDV WGQGTLVTVSS |
| MuLuc-63 VL | DIVMTQSHKFMSTSVGDRVSITC KASQDVGIAVA |
| HumanVL cDNA | DIQMTQSPSSLSASVGDRVTITC |
| HuLuc-63 VL | DIQMTQSPSSLSASVGDRVTITC KASQDVGIAVA |
| MuLuc-63 VL | WYQQKPGQSPKLLIY WASTRHT |

TABLE 6-continued

| Luc63 (NYA) Humanization | |
|---|---|
| HumanVL cDNA | WYQQKPGKVPKLLIY |
| HuLuc-63 VL | WYQQKPGKVPKLLIY WASTRHT |
| MuLuc-63 VL | GVPDRFTGSGSGTDFTLTISNVQSEDLADYFC |
| HumanVL cDNA | GVPSRFSGSGSGTDFTLTISSLQPEDVATYYC |
| HuLuc-63 VL | GVPDRFSGSGSGTDFTLTISSLQPEDVATYYC |
| MuLuc-63 VL | QQYSSYPYT FGGGTKLEIK |
| HumanVL cDNA | FGQGTKVEIK |
| HuLuc-63 VL | QQYSSYPYT FGQGTKVEIK |

Design of HuLuc63 V Regions

Humanization of the antibody V regions was carried out as outlined by Queen, C. et al. (Proc. Natl. Acad. Sci. USA 86: 10029-10033 (1989)). First, a molecular model of the MuLuc63 variable regions was constructed with the aid of the computer programs ABMOD and ENCAD (Levitt, M., J. Mol. Biol. 168: 595-620 (1983)). Next, based on a homology search against human antibody cDNA sequences, the human VH sequence E55 3-14 (Cuisinier et al, Eur. J. Imm. 23:110-118 (1993)) and the J segment JH1 (Ravetch, J. V. et al., Cell 27: 583-591 (1981)) were selected to provide the frameworks for the HuLuc63 heavy chain variable region. For the HuLuc63 light chain variable region, the cDNA VL sequence III-2R (Manheimer-Lory et al, J. Exp. Med. 174:1639-1652 (1991)) was used. The identity of the framework amino acids between MuLuc63 VH and the acceptor human frameworks was 81.6% (71/87), while the identity between MuLuc63 VL and the acceptor human frameworks was 76.3% (61/80). The alignments of MuLuc63, HuLuc63, and the human acceptor amino acid sequences for VH and VL are shown in Tables 7 and 8, respectively. Table 7 provides an alignment of the VH region amino acid sequences. The amino acid sequences of the VH regions of MuLuc63 and HuLuc63 (SEQ ID NOS:45 and 47, respectively), and the human E55 3-14 and JH1 segments (SEQ ID NO:46) are shown in single letter code. The CDR sequences are based on the definition of Kabat (Sequences of Proteins of Immunological Interest, 5th ed., National Institutes of Health, Bethesda, Md. (1991)) are underlined in the MuLuc63 VH sequence; numbering is also according to Kabat. The CDR sequences in the human VH segment are omitted in the figure. The single underlined amino acids in the HuLuc63 VH sequence were predicted to contact the CDR sequences and therefore substituted with the corresponding mouse residues. The threonine (T) to alanine (A) mutation made in CDR2 to eliminate the potential N-linked glycosylation site (NYT) is indicated with a double underline, making the heavy chain CDR2 sequence of HuLuc63 EINPDSSTNATPSLKD (SEQ ID NO:87). Table 8 provides an alignment of the VL region amino acid sequences. The amino acid sequences of the VL regions of MuLuc63 and HuLuc63 (SEQ ID NOS:48 and 50, respectively), and the human III-2R sequence (SEQ ID NO:49) are shown in single letter code. The CDR sequences based on the definition of Kabat (Sequences of Proteins of Immunological Interest, 5th ed., National Institutes of Health, Bethesda, Md. (1991)) are underlined in the MuLuc63 VL sequence; numbering is also according to Kabat. The CDR sequences in the human VL segment are omitted in the figure. The single underlined amino acids in the HuLuc63 VL sequence were predicted to contact the CDR sequences and therefore substituted with the corresponding mouse residue.

TABLE 7

Alignment of the VH regions of MuLuc63 (SEQ ID NO: 45),
E55 3-14 (SEQ ID NO: 46), HuLuc63 (SEQ ID NO: 47)

```
                        10        20        30        40
MuLuc63        EVKLLESGGGLVQPGGSLKLSCAASGFDFSRYWMSWVRQAPG

E55 3-14       EVQLVESGGGLVQPGGSLRLSCAASGFTFS-----WVRQAPG

HuLuc63        EVQLVESGGGLVQPGGSLRLSCAASGFDFSRYWMSWVRQAPG 50                                  
                   a       60        70        80    a
MuLuc-63       KGLEWIGEINPDSSTINYTPSLKDKFIISRDNAKNTLYLQMS

E55 3-14       KGLEWVA----------------RFTISRDNAKNSLYLQMN

HuLuc-63       KGLEWIGEINPDSSTINYAPSLKDKFIISRDNAKNSLYLWMN 1        1
                        9        0        1
                       bc        0ab      0
MuLuc-63       KVRSEDTALYYCARPDGNYWYFDVWGAGTTVTVSS

E55 3-14/JH1   SLRAEDTAVYYCAR----------WGQGTLVTVSS

HuLuc-63       SLRAEDTAVYYCARPDGNYWYFDVWGQGTLVTVSS
```

TABLE 8

Alignment of the VL region of MuLuc63 (SEQ ID NO: 48), III-2R
(SEQ ID NO: 49) and HuLuc63 (SEQ ID NO: 50)

```
                        10        20        30        40
MuLuc63   DIVMTQSHKFMSTSVGDRVSITCKASQDVGIAVAWYQQKPGQ

III-2R    DIQMTQSPSSLSASVGDRVTITC----------WYQQKPGK

HuLuc63   DIQMTQSPSSLSASVGDRVTITCKASQDVGIAVAWYQQKPGK 50        60        70        80
MULUC63   SPKLLIYWASTRHTGVPDRFTGSGSGTDFTLTISNVQSEDLA

III-2R    VPKLLIY-------GVPSRFSGSGSGTDFTLTISSLQPEDVA

HuLuc63   VPKLLIYWASTRHTGVPDRFSGSGSGTDFTLTISSLQPEDVA 9        1
                        0        0
                                 0
MULUC63   DYFCQQYSSYPYTFGGGTKLEIK
```

TABLE 8-continued

Alignment of the VL region of MuLuc63 (SEQ ID NO: 48), III-2R
(SEQ ID NO: 49) and HuLuc63 (SEQ ID NO: 50)

```
III-2R   TYYC---------FGQGTKVEIK

HuLuc63  TYYCQQYSSYPYTFGQGTKVEIK
```

At framework positions in which the computer model suggested significant contact with the CDRs, the amino acids from the MuLuc63 V regions were substituted for the original human framework amino acids. This was done at residues 28, 48, 49, 66 and 68 of the heavy chain (Table 7). For the light chain, replacement was made at residue 60 (Table 8). Note that the numbering system used here is that of Kabat (Sequences of Proteins of Immunological Interest, 5th ed., National Institutes of Health, Bethesda, Md. (1991)).

In addition, inspection of the MuLuc63 amino acid sequence revealed a site for potential N-linked glycosylation in CDR2 of the VH region. Such N-linked glycosylation sites have the general sequence N-X-T/S (where N=asparagine, X=any amino acid, and S/T=serine or threonine). Since the presence of N-linked glycosylation in the variable domain could have undesirable effects during development of HuLuc63 as a therapeutic antibody, the potential glycosylation site in CDR2 (N-Y-T) was eliminated by substitution of threonine with alanine mutation (N-Y-A) in the humanized design.

Construction of HuLuc63 VH and VL Genes

A gene encoding each of HuLuc63 VH and VL was designed as a mini-exon including a signal peptide, a splice donor signal, and appropriate restriction enzyme sites for subsequent cloning into a mammalian expression vector. The splice donor signals in the VH and VL mini-exons were derived from the corresponding human germline JH6 and JK4 sequences, respectively. The signal peptide sequences in the HuLuc63 VH and VL mini-exons were derived from the corresponding MuLuc63 VH and VL sequences, respectively. The nucleotide sequences of Luc63 VH and VL genes along with deduced amino acid sequences are shown in Tables 5 and 6.

The HuLuc63 VH and VL genes were constructed by extension of overlapping synthetic oligonucleotides ranging in length from 33 to 43 bases and PCR amplification. (Stemmer et al, Gene 164:49-53 (1995)). The PCR-amplified fragments were purified by Qiaquick PCR purification kit (Qiagen) and digested with MluI and XbaI. The HuLuc63 VH gene was subcloned into pHuHCg1.D to create plasmid pHuHCg1.D-HuLuc63. The HuLuc63 VL gene was subcloned into pHuCkappa.rgpt.dE, a derivative of the kappa light chain expression vector pOKT3.Vk.rg (Cole, M. S. et al., J. Immunol. 159: 3613-3621 (1997)), to create plasmid pHuCkappa.rgpt.dE-HuLuc63.

Expression of HuLuc63

HuLuc63 IgG1/κ antibody was produced by transient transfection of tissue culture cells. Human embryonic kidney cell line 293-H (Invitrogen, Carlsbad, Calif.) was maintained in DMEM (BioWhittaker, Walkersville, Md.) containing 10% FBS (HyClone, Logan, Utah) and non-essential amino acids (Invitrogen). 293-H cells were plated at $1\times10^6$ cells per well in a volume of 2.5 ml in a 6-well plate the day before transfection using regular media (DMEM+10% FBS+non-essential amino acids). On the day of transfection, 4 µg of plasmid DNA per well was diluted in 250 µl of Hybridoma-SFM (H-SFM, Invitrogen). 10 µl of lipofectamine 2000 Reagent (LF2000, Invitrogen) per well was diluted in 250 µl H-SFM. Diluted DNA was combined with diluted LF2000 and incubated for 20 minutes to allow DNA-LF2000 complexes to form. 500 µl of DNA-LF2000 complexes were added to each well and mixed by tilting the plate back and forth. Cells were incubated for 5 days before harvesting supernatant for analysis.

Expression of HuLuc63 was measured by sandwich ELISA. Immulon 4 HBX plates (Thermo Labsystems, Franklin, Mass.) were coated overnight at 4° C. with 100 µl/well of 1.8 µg/ml of goat anti-human IgG Fcγ-chain specific polyclonal antibodies (Jackson ImmunoResearch Laboratories, Inc., West Grove, Pa.) in 0.2 M sodium carbonate-bicarbonate buffer, pH 9.4, washed with Wash Buffer (PBS containing 0.1% Tween 20), and blocked for 30 min at room temperature with 150 µl/well of SuperBlock Blocking Buffer in TBS (Pierce Chemical Company, Rockford, Ill.). After washing with Wash Buffer, samples containing HuLuc63 were appropriately diluted in ELISA Buffer (PBS containing 1% BSA and 0.1% Tween 20) and 100 µl/well was applied to the ELISA plates. As a standard, humanized anti-CD33 IgG1/κ monoclonal antibody HuM195 (Co, M. S. et al., J. Immunol., 148: 1149-1154 (1992)) was used. After incubating the plates for 1 hr at room temperature and washing with Wash Buffer, bound antibodies were detected using 100 µl/well of a 1:1000 dilution of HRP-conjugated goat anti-human kappa chain polyclonal antibodies (SouthernBiotech, Birmingham, Ala.). After incubating for 1 hr at room temperature and washing with Wash Buffer, color development was performed by adding 100 µl/well of ABTS substrate (KPL, Inc., Gaithersburg, Md.). Color development was stopped by adding 100 µl/well of 2% oxalic acid. Absorbance was read at 415 nm using a VersaMax microplate reader (Molecular Devices Corporation, Sunnyvale, Calif.).

Binding Properties of MuLuc63 and HuLuc63

The affinities of MuLuc63 and HuLuc63 to human CS-1 were analyzed by direct binding ELISA. Wells of 96-well ELISA plates (Immulon 4 HBX plates, Thermo Labsystems, Franklin, Mass.) were coated with 100 µl of 1 µg/ml soluble human CS1—human Fcγ3 fusion protein in PBS overnight at room temperature. After washing with Washing Buffer, wells were blocked with 150 µl of Superblock Blocking Buffer for 30 minutes at room temperature. Transiently expressed HuLuc63 antibody or purified MuLuc63 antibody were appropriately diluted in ELISA Buffer and applied to ELISA plates (100 µl per well). ELISA plates were incubated for 1 hour at room temperature and the wells were washed with Washing Buffer. Then 100 µl of HRP-conjugated goat-anti-human CK antibody or HRP-conjugated goat-anti-mouse CK antibody (both from Southern Biotech) diluted 1:1000 in ELISA Buffer was added to each well of the HuLuC63 and MuLuc63 plates, respectively and incubated at room temperature for 1 hour. After washing with Washing Buffer, 100 µl of ABTS substrate (KPL) was added to each well. Color development was stopped by adding 100 µl of 2% oxalic acid per well. Absorbance was read at 415 nm using a VERSAmax microplate reader. The results of the ELISA binding experiments showed that MuLuc63 and HuLuc63 bind to human CS-1-Fcγ3 in a concentration-dependent manner The $EC_{50}$ value of HuLuc63, obtained using the computer software GraphPad Prism (GraphPad Software Inc., San Diego, Calif.), was 70.1 ng/ml. This is similar to the EC50 value of 66.1 ng/ml obtained for muLuc63, indicating that humanization of mouse anti-CS1 monoclonal antibody MuLuc63 was successful: HuLuc63 retained high binding affinity to human CS1.

Example 6

Role of CS1 in Autoimmune Disorders

CS1 is Highly Expressed in Stimulated T and B Cells, as Compared to Unstimulated Cells:

To determine the expression of CS1, an in-vitro assay was set up to stimulate peripheral blood B and T lymphocytes, using pokeweed mitogen (PWM) and phytohemagglutinin (PHA) stimulants. Unstimulated control peripheral blood mononuclear cells were prepared in parallel with no stimulation. PolyA$^+$ mRNA was isolated and cDNA was synthesized from these samples using standard techniques. The CS1 gene was amplified by PCR using CS1-specific oligonucleotide primers (see above) and expression was quantified using Biorad Gel Doc 2000. Signal intensities were normalized to control human β-actin. Real time PCR analysis indicated that CS1 showed about 23-fold up-regulation in activated peripheral blood B cells and about 30-fold up-regulation in activated peripheral blood T lymphocytes, as compared to unstimulated cells.

CS1 is up-regulated in the lupus patient's peripheral blood B lymphocytes as compared to those of the age-matched healthy adults:

To evaluate CS1 expression in lupus patients compared to healthy individuals, peripheral blood B lymphocytes were isolated by cell sorting of CD19$^+$ cells from a lupus patient versus a pool of healthy adults. PolyA$^+$ mRNA was isolated and cDNA was synthesized by using standard techniques. CS1 expression was evaluated by real time PCR using oligonucleotide primers specific to CS1. Real time PCR data indicated that CS1 is up-regulated about 2-fold in B lymphocytes from the lupus patient as compared to the healthy individuals. Upon normalization with β-actin, the CS1 gene was increased 2.3 fold in the lupus patient's B lymphocyte cDNA as compared to the healthy individuals' cDNA. When normalized with 18S rRNA primers, CS1 was increased 1.8 fold in the respective cDNA samples.

Up-Regulation of Mouse Novel Ly9 in Activated B and Activated T Cells:

Mouse novel Ly9 is a proposed orthologue of human CS1 (Tovar et al., Immunogenetics 54: 394-402 (2002)). The expression of mouse novel Ly9 in activated B and activated T cells was examined with real time PCR. The data showed that mouse novel Ly9 is up-regulated in activated B and activated T cells.

Mouse novel Ly9 expression was analyzed with an ABI GeneAmp 5700 Sequence Detection System (see Example 2). Upon normalization with 18S rRNA primers, the Ly9 gene was increased by 3 fold in the conA-stimulated cDNA, and up-regulated by 6 fold in LPS-stimulated cDNA as compared to the unstimulated splenic cDNA.

Upregulation of CS1 in Inflammatory Bowel Disease Tissue

The expression of IBD modulator protein(s) in IBD tissue (both Crohn's disease and ulcerative colitis) versus normal tissue was determined on microchip arrays as described above. Oligonucleotide microarrays were interrogated with cRNAs derived from multiple tissues. More specifically, cRNAs were generated by in vitro transcription assays (IVTs) from nine IBD and nine matched adjacent normal bowel specimens, and 24 colonic epithelial samples. cRNA hybridization to the oligonucleotide microarrays was measured by the average fluorescence intensity (AI), which is directly proportional to the expression level of the gene.

The data was analyzed by comparing gene expression levels in IBD to non-pathogenic adult tissues and organs. One of the genes identified with a significant increase in gene expression in inflammatory bowel disease tissue compared to normal tissue is CS1. A microarray analysis showed that CS1 gene expression is increased in ulcerative colitis and Crohn's as compared to healthy adult colonic epithelial cells.

To further evaluate CS1 expression in inflammatory bowel disease patients compared to healthy individuals, samples from diseased sections of large intestine from 2 Crohn's disease patients and 3 ulcerative colitis patients versus normal large intestine samples from 3 healthy adults were disaggregated, washed, and placed in TRIZOL®. Total RNA was isolated following the manufacturer's protocol. The total RNA was treated with Rnase free Dnase (GenHunter). The Dnase digested RNA was extracted with phenol/chloroform, and precipitated overnight with ethanol. RNA was washed with 75% ethanol and dissolved in nuclease-free water. RNA was quantified and the integrity of the RNA was analyzed on an agarose gel. Real time PCR data indicated that CS1 is up-regulated 7-fold and 6-fold in diseased large intestine from Crohn's patients (n=2) and 13-fold, 14-fold and 46-fold in diseased large intestine from ulcerative colitis patients (n=3) compared to pooled normal intestine from healthy individuals (n=3).

Example 7

CS1 Expression on Cancer Cells

CS1 Protein Expression Pattern:

CS1 protein expression was further examined with the produced Luc antibodies through FACS analysis. Cell lines were incubated with anti-CS1 Luc90.H1 antibodies or mouse IgG2b isotype control antibodies for 30 minutes on ice. Cells were washed with PBS and phycoerythrin (PE)-conjugated anti-mouse Ig was added to the cells and incubated for 30 minutes on ice. Cells were washed and analyzed by flow cytometry on a FACS Caliber (Becton Dickinson). These data show that CS1 is expressed in ARH-77 leukemia line cells, CESS and IM9 B lymphoblastoid cell lines, and L363, LP1, and OPM2 myeloma cell lines.

Samples from patients with multiple myeloma (n=21 bone marrow samples), a patients-with MGUS (monoclonal gammopathy of unknown significance; n=1), a patient with plasma cell leukemia (n=1), CD34+ stem cells mobilized from bone marrow (n=5), normal marrow cells (n=3), normal lymph node tissue (n=1), patients with Chronic Lymphoblastic Leukemia (CLL; n=15), patients with acute myelogenous leukemia (AML; n=11), a patient with non-Hodgkin's lymphoma (NHL; n=1), and a patient with Hodgkin's lymphoma (n=1) were incubated with FITC conjugated antibodies to CS1 (Luc90 or Luc63), CD45-PerCP, CD38-PE, and/or CD138-PE and processed as detailed above for FACS analysis of myeloma cells. The mouse anti-CS1 antibodies used herein are Luc90 (IgG$_2$b), Luc63 (IgG2a), Luc38 (IgG2b) and other produced anti-CS1 Luc antibodies. Isotype control antibodies were isotype matched mouse IgG antibodies.

Bone marrow aspirates were obtained from multiple myeloma patients from the Cleveland Clinic. Myeloma cell lines (LP1, L363, OPM2, NC1-H929, RPMI 8226, and U266 B1), the leukemia cell line ARH-77, B lymphoblastoid lines (IM9, CESS), and bone marrow cells were stained with anti-CS1 monoclonal antibodies versus isotype control antibodies (Becton Dickinson) following a standard staining protocol. Cells were washed, placed in staining buffer (RPMI, 10% FBS for human cells or DMEM, 10% FBS), and anti-CS1 versus isotype control antibodies were added at 0.5-1 ug antibody per million cells in 0.1 ml final volume. For patient samples, red blood cells were lysed, and cells were pelleted in a centrifuge and resuspended in staining buffer. For antibodies that were not directly conjugated to FITC, second stage antibodies were added at 0.5-1 ug antibody per million cells in 0.1 ml final volume. Cells were washed and resuspended in staining buffer for FACS analysis on a Becton Dickinson FACSCaliber using CellQuest software. To distinguish plasma cells, multiple myeloma bone marrow cells were stained with anti-CD45, anti-syndecan-1 (CD138), and anti-CD38 monoclonal antibodies. Anti-syndecan-1 (CD138) specifically stains plasma cells and not other leukocytes.

The results show that CS1 is highly expressed on plasma cells (eg CD138+ cells) from ten multiple myeloma patients and plasma cells from a plasma cell leukemia patient, as well as on several myeloma cell lines (L363, LP1, and OPM2). A total of 21 different bone marrow samples from multiple myeloma patients have been assayed by flow and for all 21 out of 21 samples, virtually all of the bone marrow plasma cells express CS1. CS1 is also expressed on ARH-77 leukemia cells and B lymphoblastoid cell lines (IM9 and CESS).

Example 8

Expression of CS1 on Plasma Cells from Myeloma Patient

Bone marrow samples from a multiple myeloma patient were stained with CD138-PE, CD45PerCP, Luc90-FITC, and/or IgG2b-FITC (isotype control antibody) and analyzed by FACS as detailed above (see Example 5). Cells were gated to contain lymphocytes, monocytes, granulocytes, erythroid cells, plasma cells, and blasts. The data showed that CS1 is expressed on plasma cells (eg CD 138+ cells) from the multiple myeloma patient.

Example 9

Anti-CS1 Monoclonal Antibody Decreases IgM Secretion by Activated Peripheral Blood B Cells Peripheral blood mononuclear cells from a normal adult were isolated by a standard Ficoll gradient, incubated with pokeweed mitogen at 10 µg/ml (GIBCO/BRL, England, the United Kingdom), and plated in a 24-well plate in a total volume of 1 ml. Monoclonal antibody (mouse anti-human CS1 (Luc63) or mouse IgG isotype control) was added to sample wells at 100 µg/ml or 10 µg/ml. The cells and the antibody were incubated at 37° C. in 7% $CO_2$ for 8 days. Supernatants from cultures were isolated and IgM was assayed by ELISA as described above. The result showed that the antibody Luc63 at 100 µg/ml or 10 µg/ml decreased the secretion of IgM of the peripheral blood mononuclear cells compared to IgM secretion by cells incubated with the isotype control at 100 µg/ml or 10 µg/ml or no antibody.

Anti-CS1 Monoclonal Antibody Decreases IgM Secretion by Auto-Immune Disease Patient Activated Peripheral Blood B Cells:

Supernatants from the cell cultures of peripheral blood mononuclear cells were isolated as detailed above and assayed by ELISA. Immulon-1 plates were coated with 100 µl of 1 µg/ml mouse anti-human IgM monoclonal antibody (catalog #05-4900, Zymed Laboratories, Inc., South San Francisco, Calif.) in PBS. The plates were blocked for 1 hour with ELISA Buffer ('EB'=PBS+0.1% BSA+0.05% Tween 20). The culture supernatants were added at various dilutions (in EB) at 100 µl/well. The supernatants and standard human IgM (catalog #009-000-012, Jackson Laboratory, Bar Harbor, Me.) were incubated for 1-2 hours at room temperature. Captured human IgM was developed with goat anti-human IgM-HRP polyclonal antibody (catalog #2020-05, Southern Biotech Association, Birmingham, Ala.) and HRP substrate, by following the manufacturer's protocol. Bound IgM was visualized by spectrophotometry (405 nm OD) on a standard ELISA plate reader. The data showed that the amount of the secreted IgM of the lupus patient PBMCs was reduced from 0.18 µg/ml when treated with an isotype controlled antibody to 0.10 µg/ml by the treatment with anti-CS1 antibodies (Luc90H1). A positive control anti-CD2 antibody which secreted IgM at 0.12 µg/ml showed that anti-CS1 is even more robust at reducing IgM production than the anti-CD2 antibody.

Anti-CS1 Monoclonal Antibody Decreases IgG Production by Peripheral Blood B Cells from Healthy Adults and from Auto-Immune Disease Patients.

IgG production by peripheral blood B cells from healthy adults and autoimmune disease (lupus) patients were analyzed the same way as the IgM production. The result showed that the total production by healthy adult peripheral blood mononuclear cells 9 days after the treatment with the anti-CS1 antibody (Luc90H.1) decreased by about 23% as compared with the IgG2b isotype control. The total production of IgG by lupus patient peripheral blood mononuclear cells 9 days after the treatment with anti-CS1 antibody (Luc90H.1) decreased by about 56% as compared with the IgG2b isotype control. Tables 3A and B summarize the inhibition of the IgG production by a number of generated anti-CS1 antibodies. As shown in Table 3A, Luc90.H1 reduced by about 40% the IgG production by PBMCs activated with lipopolysaccharide or pokeweed mitogen. Luc34.1 reduced by about 38% the IgG production by PBMCs activated with pokeweed mitogen. As shown in Table 3B, Luc 90.H1 reduced the IgG production of PBMCs of a healthy adult and a mature B cell line (IM9 cells) by about 48%. Luc 34.1 reduced the IgG production of PBMCs of the healthy adult by about 53%. Luc 63.2 reduced the IgG production of PBMCs and IM9 cells by about 47%. From these experiments, it is evident that Luc 90H.1, Luc34.1, and Luc 63.2 are the best functional antibodies. From epitope mapping, Luc90 and Luc63 have nonoverlapping epitopes.

TABLE 3A

ANTI-CS-1 DECREASES IG PRODUCTION
By In Vitro Activated B Cells
Mean Percent Decrease Compared to Isotype Control

| In Vitro Activated PBMCs | ANTI-CS-1 MAB | Average % Decrease HuIgG ± SE |
|---|---|---|
| Lipopolysaccharide | Luc 90.H1 | 41% ± 8% (n = 3) |
| Pokeweed Mitogen | Luc 90.H1 | 39% ± 9% (n = 4) |
| Pokeweed Mitogen | Luc 34.1 | 38% ± 7% (n = 4) |

TABLE 3B

Summary of Ig Production Assays with Anti-CS-1 Antibody Panel
Mean Percent Change In Ig Compared To Isotype Control

| ANTI-CS1 Mab | PMBC Donor 55 | PMBC Donor 705 | IM9 | Average % Change in Ig |
|---|---|---|---|---|
| Luc90H.1 | −44% | −56% | −43% | −48% |
| Luc37 | +11% | −43% | −11% | −14% |
| Luc23 | −13% | −4% | +6% | −4% |
| Luc63.2 | −55% | −51% | −36% | −47% |
| Luc34.1 | −64% | −49% | −45% | −53% |
| Luc38.1 | −22% | −44% | −21% | −29% |
| Luc29D6 | −43% | −44% | −25% | −37% |

Relative Decrease in Ig Production:

Group A (>45% dec): Luc 90, 63, 34
GROUP B (29-37% DEC): LUC38, 29D6
GROUP C (4-14% DEC): LUC 37, 23

The experimental results indicated that anti-CS1 antibodies decrease the production of both IgG and IgM by peripheral blood B cells in vitro.

Example 10

In Vivo Reduction of IgG by CS1 Monoclonal Antibodies in a SCID-HuPBMC Mouse Model SCID-HuPBMC Mouse Model Human peripheral blood mononuclear cells (PBMCs) were isolated by standard Ficoll-paque (Amersham Biosciences) density gradients and resuspended in phosphate buffered solution (PBS) at 2×107PBMCs/ml. Resuspended PBMCs (1 ml) were injected intraperitoneally (i.p.) into C.B-17 SCID mice. Two to three weeks after PBMC injection, serum samples were drawn from mice and assayed for human IgG by ELISA. Engrafted mice (producing >1 μg/ml human IgG in serum) were randomized into treatment groups and then treated with mouse anti-human CS-1 monoclonal antibodies (Luc90.H1 or Luc63.2.22), mouse isotype control antibodies (IgG2b or IgG2a, respectively), or PBS. Mice were dosed with 200 μg of antibody in 500 μl PBS every 3-4 days with 3 or 4 doses of antibody. Mouse serum was analyzed for human IgG by ELISA using standard protocols.

The percent change in serum human IgG was calculated for each mouse by subtracting human IgG concentration prior to the first dose of antibody (day 0) from the human IgG concentration post dose (day x), dividing by the human IgG concentration prior to the first dose (day 0), and multiplying by 100, e.g., [(day x−day 0)/day 0]×100. Data are shown as the average percent change with the standard error for each group of mice. Human IgG concentrations are the average concentration with the standard error for each group of mice. The Welch 2 sample t-test was used to compare the percent change in human IgG across treatment groups.

Anti-CS1 Antibodies Reduced the Production of Human IgG In Vivo

The data shows that anti-CS1 antibodies of the present invention reduce human immunoglobulin production substantially in the SCID-HuPBMC transfer model. As shown in FIG. 1A, Luc90.H1 held down the increase in IgG production in PBS and isotype control as early as Day 4 (4 days after the treatment with the first dose of the antibody). This reduction continued throughout the 7 weeks (Day 32) of the test period. For example, at Day 18, the human IgG production increased by 225% in IgG2b isotype control, by 181% in the PBS control, while human IgG production decreased by 14% with Luc90H.1 treatment. Luc90H.1 not only abolished the 181-225% increase in the human IgG production in the control groups, but also resulted in an additional 14% decrease in the IgG production. At Day 25, Luc90H.1 not only abolished the 3 fold increase in human IgG production in the control groups, but also gave an additional 24% decrease in human IgG production.

Figure 1B:
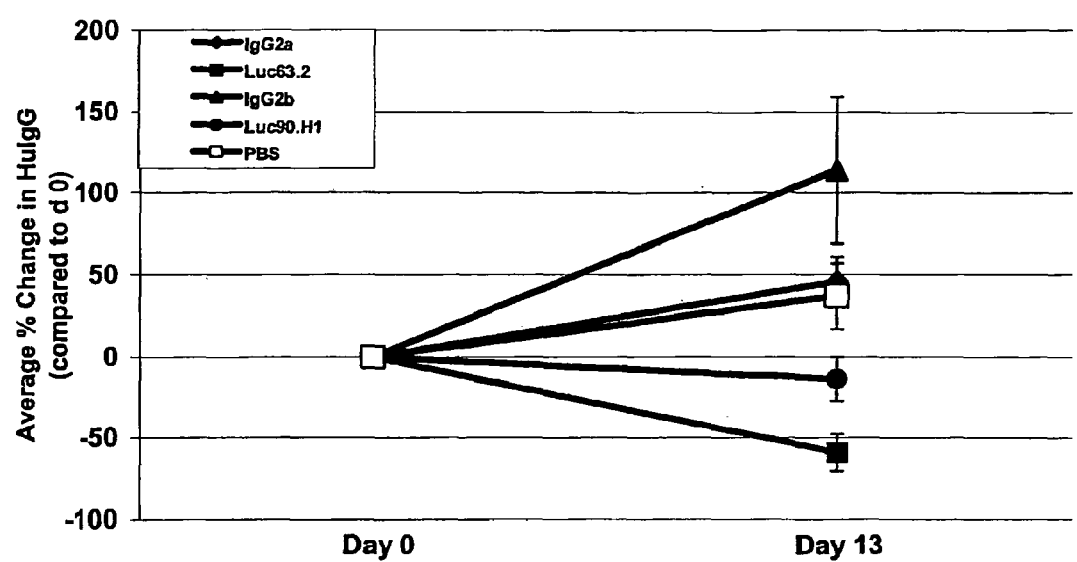
FIG. 1B shows a comparison of inhibition of in vivo human IgG production in SCID-HuPBMC mouse model by anti-CS1 monoclonal antibodies Luc 90 and 63.

Luc63.2 also effectively reduced IgG production in vivo. As shown in FIG. 1B, Luc63.2 abolished the 37-46% increase in human IgG production in the control groups (PBS and IgG2a isotype control) and gave rise to an additional 59% decrease in IgG production. In this same study, Luc90.H1 was compared with Luc63.2 and Luc90.H1 abolished the 37-114% increase in the control groups (PBS and IgG2b isotype control) and gave an additional 14% decrease in IgG production by mice engrafted with human peripheral blood mononuclear cells (PBMCs).

Figure 1C:
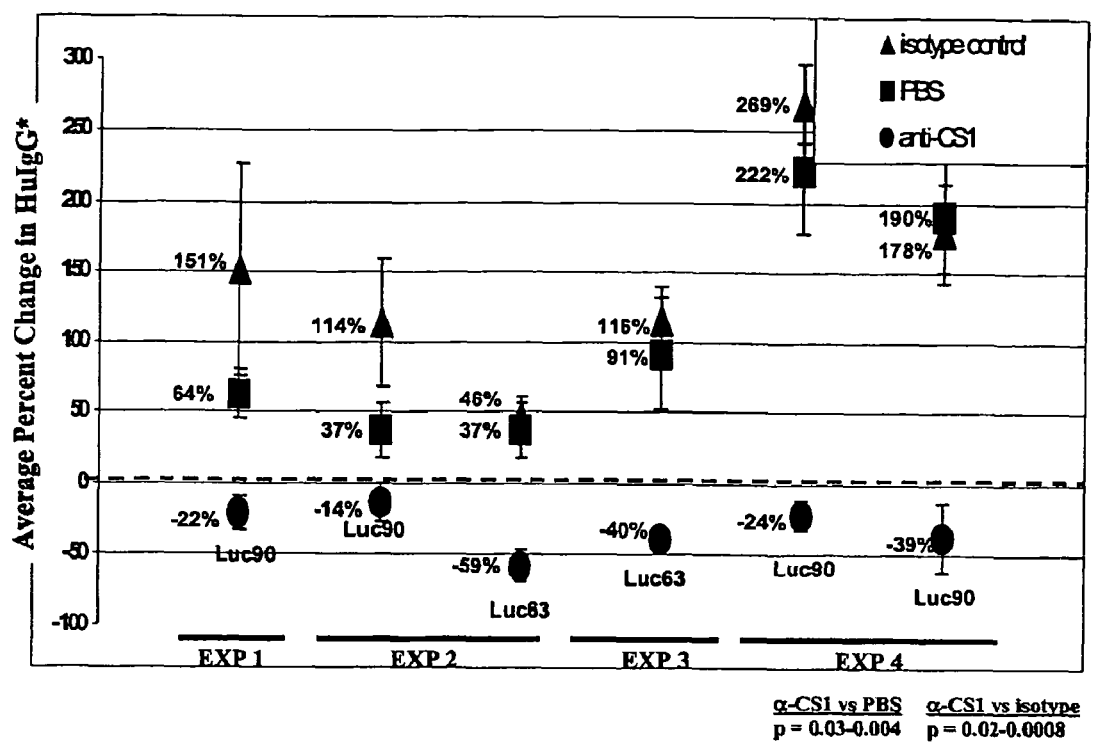
FIG. 1C shows a summary of the inhibition of in vivo human IgG production in SCID-HuPBMC mouse model by anti-CS1 monoclonal antibodies.

FIG. 1C further summarizes the reduction in the Ig production by Luc90 and Luc63 treatment in the SCIDHuPBMC model. While abolishing the increase of IgG production in mice treated with isotype and PBS controls, Luc90 caused an additional decrease in IgG production by 14%, 22%, 24%, and 39%, and Luc63 had additional decrease by 40% and 59%. Thus, we can conclude that anti-Luc treatment of SCID mice engrafted with human PBMCs (SCID-HuPBMC) not only completely abolishes the increase in human immunoglobulin normally observed in the serum of these animals, but also gives an additional decrease compared to pretreatment levels.

Example 11

ADCC Activities of Anti-CS1 Antibodies

Effector Cells Preparation:

Human peripheral blood mononuclear cells (PBMCs) (effector cells) were isolated from whole blood using standard density Ficoll-Paque (Amersham Biosciences) gradients. Cells were washed and resuspended in RPMI medium supplemented with 1% bovine serum albumin (BSA).

Target Cells Preparation:

Stable transfectant cells expressing cell surface CS-1 (target cells) were washed and resuspended in RPMI medium supplemented with 1% BSA. Cells were plated at 100,000 cells/well in 50 μl total volume. Mouse anti-human CS-1 monoclonal antibodies (Luc90.H1 or Luc63.2.22) or isotype control antibodies (mouse IgG2b or IgG2a, respectively) were added at various concentrations to the target cells in a final volume of 100 μl, and incubated for 30 minutes at room temperature.

After incubation, 100 μl of effector PBMCs were added to the target cells at a 20:1 ratio in 200 μl final volume. Target and effector cells were incubated at 37° C. for 5 hours or overnight. Cells were centrifuged at 350×g for 5 minutes, and 100 μl/well of supernatant was collected and transferred into an optically clear 96-well flat bottom microtiter plate.

Lactate Dehydrogenase Assay:

To determine the lactate dehydrogenase (LDH) activity contained in the supernatants, 100 μl reaction mixture from Cytotoxicity Detection Kit (Roche Applied Science, Indianapolis, Ind.) was added to each well, and samples were incubated for up to 30 minutes at 15-25° C. During this incubation period, the microtiter plate was protected from light. The absorbance of the samples was measured at 490 nm using an ELISA reader.

To determine the percentage of cell-mediated cytotoxicity, the average absorbance of the samples was calculated and background controls were subtracted using the following equation:

$$\text{Cytotoxicity (\%)} = \frac{LDH\ release_{sample} - SR_{effector} - SR_{target}}{MR_{target} - SR_{target}} \times 100$$

SR: Spontaneous Release
MR: Maximum Release

The experimental controls were spontaneous release of the target cells alone or the effector cells alone. The target cells were assayed in 2% Triton-X 100 (1:1) solution:

Anti-CS1 Antibodies Induce Antibody-Derived Cytotoxicity (ADCC)

The experiment showed that anti-CS1 antibodies Luc63.2 and Luc90 induced antibody-derived cytotoxicity (ADCC) of cells expressing CS1 in the presence of PBMCs (the effector cells). The results showed that Luc90 induces cytotoxicity in a dosage-dependent manner. An amount of 50 µg/ml of Luc90 induced almost 50% cytotoxicity of the target cells. Luc63.2 generally induced 60-80% cytotoxicity of the target cells with a dose range of 10-50 µg/ml. Similar results were obtained from experiments conducted with two additional donors.

Example 12

ADCC Activity with Low Fucose CS1 Antibodies

Cloning of Luc90 Variable Region cDNAs

The murine variable regions (sequence ID #3 and #4) were cloned from the Luc90 hybridoma cell line by standard methods. Briefly, total RNA was extracted and double-stranded cDNA was synthesized using the SMART 5'-RACE cDNA Amplification Kit (BD Biosciences Clontech, Palo Alto, Calif.) following the supplier's protocol. PCR fragments of the variable region cDNAs were cloned into the pCR4Blunt-TOPO vector (Invitrogen Corporation, Carlsbad, Calif.) for sequence determination. Several plasmid clones were sequenced for each of the heavy and light chains. Unique sequences homologous to typical mouse heavy and light chain variable regions were identified.

Construction of Chimeric Luc90 VH and VL Expression Vectors

A gene encoding each of Luc90 VH and VL was designed as a mini-exon including a signal peptide, a splice donor signal, Kozak initiation sequence and appropriate restriction enzyme sites for subsequent cloning into a mammalian expression vector. Primers were designed to contain the appropriate restrictions sites and complementarity for PCR from the TOPO vectors containing either the VH or VL genes. The PCR-amplified fragments were purified by Qiaquick PCR purification kit (Qiagen) and digested with M1uI and XbaI. The Luc90 VH gene was subcloned into pHuHCg1.D (wildtype) or pHuHCg1.D.AA (BS mutant) to create the plasmids pChiHuHCg1.D-MuLuc90VH and pChiHuHCg1.D.AA-MuLuc90VH, respectively. The BS mutant contains two amino acid changes (L234A/L235A) in the CH2 region of IgG1, such that binding to Fc receptors is abolished (Xu et al., (2000) Cell Immunol. 200:16-26). The Luc90 VL gene was subcloned into pVk to create the plasmid pChiVk-MuLuc90VL. Single plasmid expression vectors were created such that the heavy and light chain genes could be expressed from a single plasmid. The heavy chain vectors were digested with EcoRI to remove the entire heavy chain region and subcloned into a single EcoRI sight in the light chain vector. The BS mutant heavy chain was combined with pChiVk-MuLuc90VL vector fragment to create the plasmid pChiLuc90-BSK while the wildtype heavy chain was subcloned into pChiVk-MuLuc90VL vector to create the plasmid pChiLuc90-glK.

Expression of Chimeric Luc90

Chimeric Luc90 IgG1/κ wildtype and BS antibodies were produced by stable transfection of Sp2/0 cells with the pChiLuc90-glK and pChiLuc90-BSK vectors, respectively. A low-fucose antibody was produced by stable transfection of YB2/0 cells with the pChiLuc90-glK vector. Positive clones were selected for with mycophenolic acid media and screened by ELISA. The wildtype clone AH4, BS mutant HG12 and low-fucose clone 5E4 were selected for high expression, adapted to Gibco Hybridoma serum free media with 2% low Ig Fetal Bovine Serum. Two liter cultures were grown in roller bottles for purification. Antibodies were purified by standard Protein-G affinity column chromatography.

The results showed that anti-CS1 Luc90 chimeric antibodies stimulate antibody-dependent cellular cytotoxicity of cells expressing CS1 in a stable cell line expressing human CS1 and two human myeloma cell lines, OPM2 and L363. In each case, cytotoxicity is significantly enhanced by antibodies which have low levels of fucose (through growth in YB2/0 cells as detailed above.)

Example 13

Treatment of Myeloma with Anti-CS1 Antibodies

Figure 2:
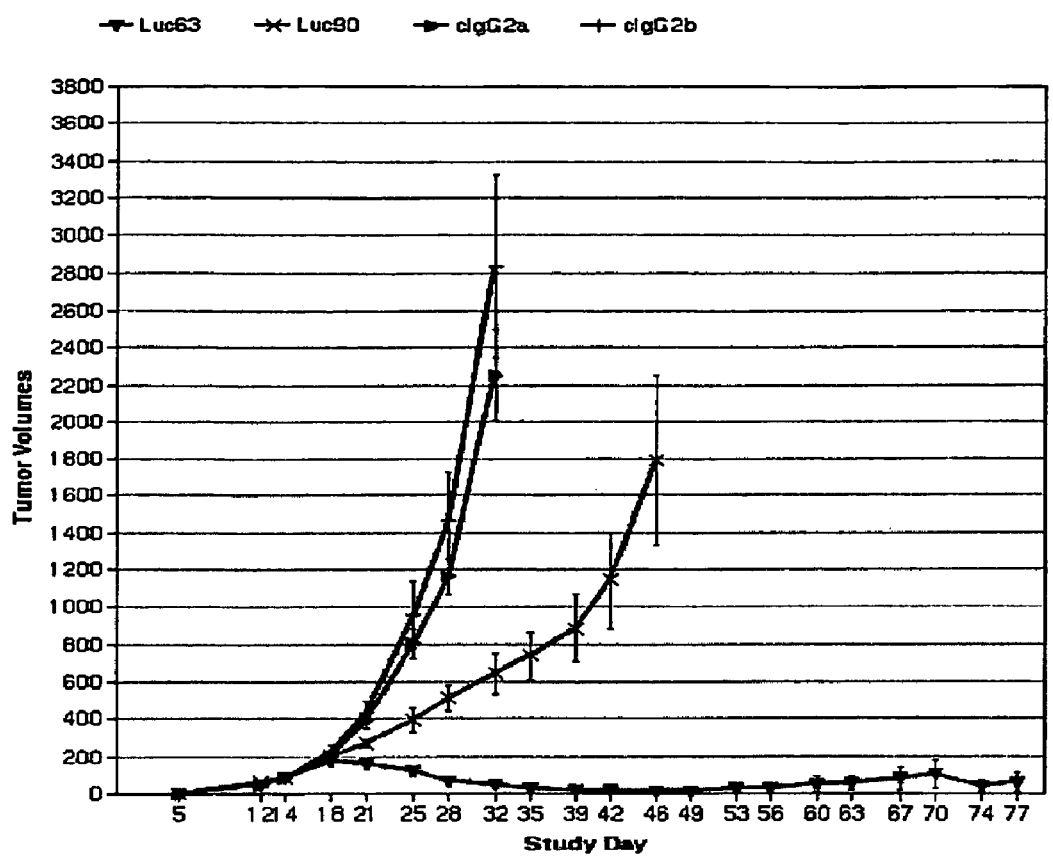
FIG. 2 shows decreased tumor volumes in mouse xenograft multiple myeloma models treated with anti-CS1 antibodies Luc 90 and Luc 63 versus isotype control antibodies.

Treatment with anti-CS1 antibody in vivo was performed on a myeloma mouse tumor model by injecting antibody intraperitoneally into the test subject. As shown in FIG. 2, anti-CS1 antibody treatment (Luc63 and Luc90) decreases tumor size compared to isotype control treated animals. In this study, $1 \times 10^7$ myeloma cells (L363 myeloma cell line) were i.p. injected into CB.17 SCID mice. Two weeks later, when tumor size reached ~80 mm3, mice were randomized into 4 groups with 8 mice per group. Mice were treated with anti-CS1 antibodies (Luc63 or Luc90) or isotype control antibodies (mouse IgG2a or mouse IgG2b). Mice were dosed with 200 µg antibody/mouse for 8 doses at 3 doses per week. The results show that mice treated with anti-CS1 antibodies have significantly reduced tumor volumes compared to isotype control antibody treated mice. By day 25 of the study (after 5 doses), Luc 63 treated mice show average tumor size ~100 mm$^3$ compared to IgG2a isotype control antibody treated mice (average tumor size ~800 mm$^3$) Luc 90 treated mice show average tumor size ~400 mm$^3$ compared to IgG2b isotype control antibody treated mice (which have average tumor size ~950 mm$^3$) Mice treated with anti-CS1 Luc63 have no measureable tumors for up to 2.5 weeks post treatment, pointing to the striking efficacy of the antibody at eliminating tumorigenic cells.

Additional model systems for myeloma include SCID mice implanted intravenously (i.v.), intraperitoneally (i.p.) or directly injected into the bone (orthotopically) with fluorescently-labeled or unlabeled myeloma or mature B-cell lines, e.g. ARH77, CESS, IM9, L363, LP1 and OPM2. These lines will be used to test the effects of antagonist treatment in myeloma animal model systems. These cell lines express the antigen recognized by anti-human CS1 antibodies. Animals are randomized into groups and subjected to a treatment regimen with anti-human CS1 antibodies or control antibodies (for example, isotype control antibodies). Antibodies are administered at several dosage levels, for example a dose of 1-10 mg/kg for a total of 9-10 doses given intraperitoneally every 3-4 days. Tumor size is measured twice weekly for 35-40 days for each treatment group. Clinical manifestations of myeloma are noted. Dates of death are recorded for each mouse.

Animal studies will also be initiated to determine the potential synergy between anti-CS1 antibody treatment and chemotherapy. Xenograft tumors are allowed to grow until they reach an approximate size of between 50-100 mm3, and for mice injected i.v., i.p. or orthotopically, cancer cells are allowed to engraft in animals. At that time, animals are randomized into groups and subjected to a treatment regimen with anti-human CS1 antibodies or control antibodies (for example, isotype control antibodies). Alternatively, animals may be subjected to treatment with anti-human CS1 antibodies or control antibodies (for example, isotype control antibodies) in combination with standard chemotherapy agents, including combinations of prednisone and melphalan or other alkylating agents (e.g. cyclophosphamide or chlorambucil), or vincristine, doxorubicin and high-dose dexamethasone (VAD) treatment, or other chemotherapy regimens known to those of skill in the art. Antibodies are administered at several dosage levels, for example a dose of 1-10 mg/kg for a total of 9-10 doses given intraperitoneally every 3-4 days. Chemotherapy is administered intraperitoneally every 3-4 days at an effective concentration, for example 1 mg/kg or other effective dose that is known to those of skill in the art. Tumor size (for s.c.injected animals) is measured twice weekly for 35-40 days for each treatment group. Clinical manifestations of myeloma are noted, including serum immunoglobulin in mice injected with cell lines that secrete human immunoglobulin (IM9, CESS, ARH-77, and LP-1). Dates of death are recorded for each mouse. The efficacy of antibody treatment in the presence and absence of chemotherapy will be evaluated.

Example 14

Treatment of Multiple Myeloma with Humanized Anti-CS1 Antibody

Treatment with a humanized anti-CS1 antibody in vivo was performed on a multiple myeloma mouse tumor model by injecting antibody intraperitoneally into the test subject, similar to the example described in Example 13. Female ICR/SCID mice were implanted sub-cutaneously (flank) with the multiple myeloma line OPM-2 (10 million cells/animal). Tumors were allowed to establish and once tumors had reached an average of 100 mm3 mice were randomized into 8 groups (8 groups of 8 mice each, average tumor volume 100 mm3).

Mice were then treated with the following antibodies, dosed 3 times per week intra-peritoneally.
Group 1 Phosphate buffered saline control (PBS)
Group 2 Murine Luc63 antibody at 10 mg/kg (MULuc63)
Group 3 An irrelevant humanized IgG1 antibody as control at 10 mg/kg (cHUIgG1)
Group 4 Humanized Luc63 at 10 mg/kg (HULuc63)
Group 5 Humanized Luc63 at 3 mg/kg (HULuc63)
Group 6 Humanized Luc63 with alanine mutations at residues 234 and 235 at 10 mg/kg (HuLuc63a,a)—this mutation is know to affect the binding of the IgG1Fc to FcRs and thus impacts on the ability of antibodies to impart Fc-dependent functions including Antibody-dependent cellular cytotoxicity (ADCC).

Figure 3:
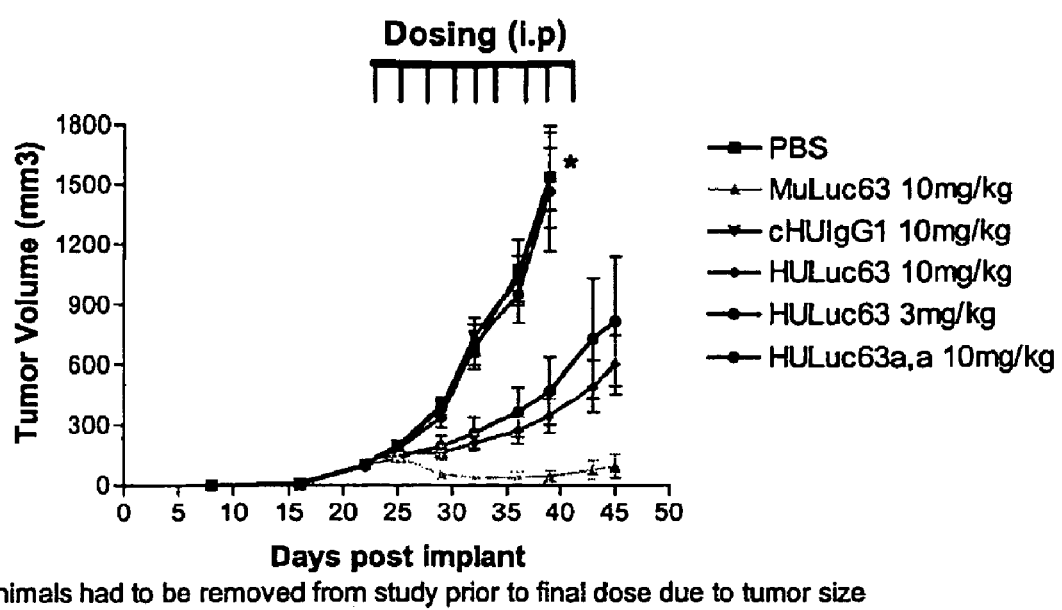
FIG. 3 shows the effect of anti-CS1 antibodies Luc63 and humanized Luc63 on OPM-2 tumor growth in vivo.

The result of this experiment is shown in FIG. 3. As observed previously the MULuc63 antibody at 10 mg/kg was effective at reducing tumor growth in vivo. At day 46 (5 days after last of 9 antibody doses) 5/8 animals had no measurable tumors. While the HULuc63 at both 3 mg/kg and 10 mg/kg was effective at reducing tumor growth the humanized antibody does not work as efficiently in mice as the murine antibody. Of interest the humanized Luc63 antibody that had been mutated at residues 234 and 235 failed to demonstrate any efficacy in this model. Indeed, like the two control groups, PBS and humanized IgG1 (cHUIgG1), the HULuc63a,a mutant—treated animals had to be sacrificed at day 39 (the day of the 8$^{th}$ antibody dose) because the tumors had become too large (and according to the IACUC regulations animals had to be sacrificed). The data generated with the HULuc63a,a mutant indicate that the Fc portion of the antibody is important in this model and suggest that one of the mechanisms by which the Luc63 antibody (and its humanized versions) work is through an imported Fc-mediated effector function such as ADCC (or possibly receptor crosslinking).

The results suggest that the efficacy of a CS1 antibody in human therapy can be enhanced by increasing the ADCC activity of the antibody. Methods for increasing ADCC activity include providing a low fucose antibody of Example 12 and generating mutation in the Fc portion of a CS1 antibody, particularly mutations which increase antibody affinity for an FcγR receptor as provided in U.S. Pat. No. 6,737,056B1 and U.S. Patent Application 2004/0132101A1, each of which is incorporated herein by reference in its entirety.

Patients may also be subjected to treatment with anti-human CS1 antibodies in combination with standard chemotherapy agents, including combinations of prednisone and melphalan or other alkylating agents (e.g. cyclophosphamide or chlorambucil), or vincristine, doxorubicin and high-dose dexamethasone (VAD) treatment, thalidomide, velcade or other chemotherapy regimens known to those of skill in the art.

Example 15

In Vivo Reduction of IgG by Humanized Anti-CS1 Antibody in a SCID-HuPBMC Mouse Model SCID-HuPBMC Mouse Model Human peripheral blood mononuclear cells (PBMCs) were isolated by standard Ficoll-paque (Amersham Biosciences) density gradients and resuspended in phosphate buffered solution (PBS) at 2×10$^7$ PBMCs/ml. Resuspended PBMCs (1 ml) were injected intraperitoneally (i.p.) into C.B-17 SCID mice. Two to three weeks after PBMC injection, serum samples were drawn from mice and assayed for human Igλ by ELISA. Engrafted mice (producing >1 µg/ml human Igλ in serum) were randomized into treatment groups and then treated with humanized Luc63 (HuLuc63), or human IgG1 isotype control antibodies. Mice were dosed with 200 µg of antibody in 500 µl PBS every 3-4 days with 4 doses of antibody. Mouse serum was analyzed for human Igλ by ELISA using standard protocols. Through detection of human Igλ we measure immunoglobulin produced by the injected human B cells, as opposed to the humanized and control human antibodies used to treat the mice, as the humanized antibodies have kappa light chains and not lambda light chains.

The percent change in serum human Igλ was calculated for each mouse by subtracting human Igλ concentration prior to the first dose of antibody (day 0) from the human Igλ concentration post dose (day x), dividing by the human Igλ concentration prior to the first dose (day 0), and multiplying by 100, e.g., [(day x−day 0)/day 0]×100. Data are shown as the average percent change with the standard error for each group of mice, comparing day 0 to day 14 of the study.

Humanized Anti-CS1 Antibody Reduced the Production of Human Immunoglobulin In Vivo The data show that the anti-CS1 antibodies of the present invention reduce human immunoglobulin production substantially in the SCID-HuPBMC transfer model. In the model, there is a ~300% increase in immunoglobulin production intrinsic to the model as seen in the isotype control treated mice. HuLuc63 abolished the ~300% increase in immunoglobulin production and resulted in an additional 2% decrease in immunoglobulin. Thus, we can conclude that, similar to treatment with the mouse-anti-human CS1, humanized anti-CS1 Luc63 antibody treatment of SCID mice engrafted with human PBMCs (SCID-HuPBMC) not only completely abolishes the increase in human immunoglobulin normally observed in the serum of these animals, but also gives an additional decrease compared to pretreatment levels. Therefore, a humanized anti-CS1 antibody will provide a useful therapeutic agent in a human patient with a disease associated with production of human immunoglobulins.

Example 16

Additional Anti-CS1 and Humanized Anti-CS1 Monoclonal Antibodies

Antibody heavy and light chain variable regions were cloned using standard techniques. Briefly, total RNA from 1-5×106 cells was used to prepare cDNA using a SMART RACE cDNA Amplification Kit (BD Biosciences Clontech) and variable regions were PCR amplified using gene specific primers complementary to the mouse heavy and light chain constant regions.

The amino acid sequences of the mature heavy chain and the mature light chain of the antibodies Luc69, LucX.1 and LucX.2 are shown in Table 9 which provides amino acid sequences of the heavy chain variable region (SEQ ID NO: 51) and light chain variable region (SEQ ID NO:52) of Luc69; the amino acid sequences of the heavy chain variable region (SEQ ID NO: 59) and light chain variable region (SEQ ID NO: 60) of LucX.1, the amino acid sequences of the heavy chain variable region (SEQ ID NO: 67) and light chain variable region (SEQ ID NO:68) of LucX.2. SEQ ID NOS: 53, 54 and 55 depict the amino acid sequences of the Luc69 heavy chain CDR1, CDR2, and CDR3, respectively. SEQ ID NOS: 56, 57, and 58 depict the amino acid sequences of the Luc69 light chain CDR1, CDR2, and CDR3, respectively. SEQ ID NOS: 61, 62, and 63 depict the amino acid sequences of the LucX.1 heavy chain CDR1, CDR2, and CDR3, respectively. SEQ ID NOS: 64, 65, and 66, depict the amino acid sequences of the LucX.1 light chain CDR1, CDR2, and CDR3, respectively. SEQ ID NOS: 69, 70, and 71 depict the amino acid sequences of the LucX.2 heavy chain CDR1, CDR2, and CDR3, respectively. SEQ ID NOS: 72, 73, and 74, depict the amino acid sequences of the LucX.2 light chain CDR1, CDR2, and CDR3, respectively.

TABLE 9

Amino Acid Sequences of CS1 antibodies Luc69 and LucX

Luc69 VH-
SEQ ID NO: 51
QVQLQQSGPELVKPGASVKISCKASGYAFSNSWMNWVKQRPGQGLEWIGRIYPGDGDTKSNGKF
                           SEQ ID NO: 53           SEQ ID NO: 54

KGKATLTADKSSRAAYMQLSSLTSVDSAVYFCARSTMIMTGANDYWGQGTSVTVSS
                               SEQ ID NO: 55

Luc69 VL-
SEQ ID NO: 52
DIVMTQSHKFMSTSVGDRVIITCKASQDVSTAVAWYQQKPGQSPKLLIYSASPRYTGVPDRFTG
                        SEQ ID NO: 56           SEQ ID NO: 57

SGSGTDFTFTVSSVQAEDLAVYYCQQHYSTPPYTFGGGTKLEIK
                      SEQ ID NO: 58

LucX.1 VH-
SEQ ID NO: 59
QVQLQQSGPELVKPGASVKISCKASGYAFSSSWMNWVKQRPGQGLEWIGRIYPGDGDTKYNGKF
                         SEQ ID NO: 61           SEQ ID NO: 62

KGKATLTADKSSTAYMQLSSLTSVDSAVYFCARSTMIATGANDYWGQGTSVTVSS
                              SEQ ID NO: 63

LucX.1 VL-
SEQ ID NO: 60
ETTVTQSPASLSMAIGEKVTIRCITSTDIDDDMNWYQQKPGEPPKLLISEGNTLRPGVPSRFSS
                      SEQ ID NO: 64           SEQ ID NO: 65

SGYGTDFVFTIENMLSEDVADYYCLQSDNLPLTFGGGTKLEIK
                      SEQ ID NO: 66

LucX.2 VH-
SEQ ID NO: 67
QVQLQQSGPELVKPGASVKISCKASGYAFSSSWMNWVKQRPGQGLEWIGRIYPGDGDTKYNGKF
                         SEQ ID NO: 69           SEQ ID NO: 70

KGKATLTADKSSTAYMQLSSLTSVDSAVYFCARSTMIATGAMDYWGQGTSVTVSS
                              SEQ ID NO: 71

LucX.2 VL-
SEQ ID NO: 68
DIVMTQSHKFMSTSVGDRVSITCKASQDVSTAVAWYQQKPGQSPKLLIYSASYRYTGVPDRFTG
                       SEQ ID NO: 72           SEQ ID NO: 73

SGSGTDFTFTISSVQAEDLAVYYCQQHYSTPPYTFGGGTKLEIK
                      SEQ ID NO: 74

The antibodies Luc69, LucX.1 and LucX.2 in Table 9, and Luc90 and Luc34 in Table 4 will be humanized according to the methods taught in Queen et al., U.S. Pat. Nos. 5,5301,101; 5,585,089; 5,693,761; 5,693,762; and 6,180,370.

Briefly, the method involves providing one or more complementarity determining regions (CDR's) from a donor (mouse) immunoglobulin and a framework region from a human immunoglobulin. The preferred methods comprise first comparing the framework or variable region amino acid sequence of the donor immunoglobulin to corresponding sequences in a collection of human immunoglobulin chains, and selecting as the human immunoglobulin one of the more homologous sequences from the collection. The human immunoglobulin, or acceptor immunoglobulin, sequence is typically selected from a collection of at least 10 to 20 or more immunoglobulin variable region sequences, and usually will have the highest homology to the donor immunoglobulin sequence of any sequence in the collection. The human immunoglobulin framework sequence will typically have about 65 to 70% homology or more to the donor immunoglobulin framework sequences. The donor immunoglobulin may be either a heavy chain or light chain, and the human collection will contain the same kind of chain. A humanized light and heavy chain can be used to form a complete humanized immunoglobulin or antibody, having two light/heavy chain pairs, with or without partial or full-length human constant regions.

To form the humanized variable region, amino acids in the human acceptor sequence will be replaced by the corresponding amino acids from the donor sequence if they are in the category: (1) the amino acid is in a CDR. Either in conjunction with the above comparison step or separately, additional amino acids in the acceptor immunoglobulin chain may be replaced with amino acids from the CDR-donor immunoglobulin chain. More specifically, further optional substitutions of a human framework amino acid of the acceptor immunoglobulin with the corresponding amino acid from a donor immunoglobulin will be made at positions which fall in one or more of the following categories: (2) the amino acid in the human framework region of the acceptor immunoglobulin is rare for that position and the corresponding amino acid in the donor immunoglobulin is common for that position in human immunoglobulin sequences; or (3) the amino acid is immediately adjacent to one of the CDR's; or (4) the amino acid is predicted to be capable of interacting with the antigen or with the CDR's of the donor or humanized immunoglobulin. Moreover, an amino acid in the acceptor sequence may optionally be replaced with an amino acid typical for human sequences at that position if (5) the amino acid in the acceptor immunoglobulin is rare for that position and the corresponding amino acid in the donor immunoglobulin is also rare, relative to other human sequences.

When combined into an intact antibody, the humanized light and heavy chains will be substantially non-immunogenic in humans and retain substantially the same affinity as the donor immuno globulin to CS1.

Once designed, the immunoglobulins, including binding fragments and other immunoglobulin forms may be produced readily by a variety of recombinant DNA or other techniques. Preferably, polynucleotides encoding the desired amino acid sequences are produced synthetically and by joining appropriate nucleic acid sequences, with ultimate expression in transfected cells. The humanized anti-CS1 monoclonal antibodies will be particularly useful in treating human disorders susceptible to monoclonal antibody therapy, as described in detail in the specification.

Example 17

CS1 Sequences of Other Primates

The amino acid sequences of the CS1 extracellular domains from several non-human primates, including cynos, chimp and Rhesus were determined and compared with the human sequence. The Rhesus sequence was determined from a sample of activated PBMC from a Rhesus monkey. The chimp sequence was determined from a sample of PBMC which had been previously stimulated with OKT3. The cynos sequence was determined from a sample of activated PBMC from a cynos monkey.

RNA was prepared from tissue samples utilizing Trizol LS reagent (Invitrogen)/chloroform extraction, followed by RNAeasy micro kit (Qiagen) clean up. First strand cDNA was prepared using the SMART RACE (Clontech). PCR was carried out with primers designed either to published sequence for each species or using human sequence if specific species sequence was not available, to isolate fragments covering the regions of interest. These fragments were cloned into the TOPO cloning system (Invitrogen) for sequencing on AB 3100 Genetic Analyzer.

Once species specific sequence was determined the required fragments were PCR'ed with cloning primers containing the required restriction sites for expression vectors. Extracellular domains of each species were subcloned into NEF39 HAPPFc, NEF39 Fc or NIF Fc vectors and Full-length ORF into NEF39 HA ICD4 vectors. The amino acid sequences were determined from translation of the nucleic acid sequences. Table 10 (SEQ ID NOS: 75, 76, 77 and 78) shows the alignment of each sequence from cynos, rhesus, human and chimp, respectively. The sequences are aligned starting with Methionine and include the respective signal peptides. Homologous amino acid residues across the species are denoted with a * symbol.

TABLE 10

Alignment of primate CS1 sequences (SEQ ID NOS: 75-78)

| | | |
|---|---|---|
| cynos | MAGSPTCFTFIYILWQLTGSTASGSVKELVGSIGGAVTFPLKSEVKQVDSIVWTFNTTTL | 60 |
| rhesus | MAGSPTCLTFIYILWQLTGSTASGSVKELVGSIGGAVTFPLKSEVKQVDSIVWTFNTTTL | 60 |
| human | MAGSPTCLTLIYILWQLTGSAASGPVKELVGSVGGAVTFPLKSKVKQVDSIVWTFNTTPL | 60 |
| chimp | MAGSPTCLTLIYILWQLTGSAASGPVRELVGSVGGAVTFPLKSKVKQVDSIVWTFNTTPL | 60 |
| | *******:*:********:*.*:***.*******:************.* | |
| cynos | VTIQPEGGPMIVTQNRNKERVHFPDGGYSLKLSKLKKNDSGIYNVEIYSSSLQDPFTRKY | 120 |
| rhesus | VTIQPEGGPMIVTQNRNKERVHFPDCGYSLKLSKLKKNDSGIYNVEIYSSSLQDPFTRKY | 120 |

TABLE 10-continued

Alignment of primate CS1 sequences (SEQ ID NOS: 75-78)

```
human   VTIQPEGGTIIVTQNRNRERVDFPDGGYSLKLSKLKKNDSGIYYVGIYSSSLQQPSTQEY    120 chimp   VTIQPECGTIIVTQNRNKERVDFPDGGYSLKLSKLKKNDSGIYYVGIYSSSLQQPSTQRY    120
        ******.:**:*.******************* * *******:* *:;* cynos   VLRVYEHLSKPKVTMGLQSNKNGTCVTNLTCCMEHGEEDVIYTWKALGQAVNESHNGSIL    180 rhesus  VLRVYEHLSKPKVTMGLQSNKNGTCVTNLTCHMEHGEEDVIYTWKALGQAVNESHNGSIL    180 human   VLHVYEHLSKPKVTMGLQSNKNGTCVTNLTCCMEHGEEDVIYTWKALGQAANESHNGSIL    180 chimp   VLHVYEHLSKPKVTMGLQSNKNGTCVTNLTCCMEHGEEDVIYTWKALGQAANESHNGSIL    180
        :*************************** **************.******* cynos   PISWRWGESDMTFICTVRNPVSSNSSSPILARKLCEGAADDSDSSMV rhesus  PISWRWGESDMTFICTVRNPVSSNSSSPILARKLCEGAADDSDSSMV human   PISWRWGESDMTFICVARNPVSRNFSSPILARKLCEGAADDPDSSMV chimp   PISWRWCESDMTFICVARNPVSSNFSSPILARKLCEGAADDPDSSMV
        ****  **..***  * ****************.***
```

Example 18

Epitope Mapping of CS1 Antibodies

Human, mouse, or human-mouse chimeric CS1-Fc proteins were constructed to assess for their ability to bind different anti-CS1 antibodies using a sandwich ELISA. The panel of anti-CS1 antibodies has been showed to bind to human CS1 protein but not the mouse CS1 protein.

CS1 Expression Vectors

The extracellular domain of human CS1 (amino acids 1-227) was subcloned into the NIP Fc vector, and the extracellular domain of mouse CS1 (amino acids 1-224) was subcloned into the NEF39 Fc vector. These vectors generate a fusion protein of the extracellular domain of CS1 cloned upstream and in frame with the human gamma 1 immunoglobulin heavy chain gene. This generates a secreted protein containing the CS1 extracellular domain and a human Fc "tag" at the C terminus PCR and Sequencing Human/mouse chimeras of the CS1 extracellular domain were generated by PCR using chimeric primers spanning the required junctions of the human and mouse sequences with previously cloned cDNA's as the source. These fragments were used in sewing PCR's to stitch the fragments together with required restriction sites for expression vectors. These chimeric fragments were cloned into the TOPO cloning system (Invitrogen) or directly into expression vector NIF Fc for sequencing on AB 3100 Genetic Analyzer. Sequence confirmed fragments were subcloned into expression vector NIF Fc.

The chimeric constructs are as follows, containing the indicated amino acids from human and mouse CS1. The sequences are provided in Table 11.

hu25/mu75: amino acids 1-67 of human CS1 fused to amino acids 68-224 of mouse CS1 (SEQ ID NO: 79);
mu25/hu75: amino acids 1-67 of mouse CS1 fused to amino acids 68-227 of human CS1 (SEQ ID NO: 80);
hu50/mu50: amino acids 1-151 of human CS1 fused to amino acids 149-224 of mouse CS1 (SEQ ID NO: 81);
mu50/hu50: amino acids 1-131 of mouse CS1 fused to amino acids 135-227 of human CS1 (SEQ ID NO: 82);
hu75/mu25: amino acids 1-169 of human CS1 fused to amino acids 167-224 of mouse CS1 (SEQ ID NO: 83);
mu75/hu25: amino acids 1-166 of mouse CS1 fused to amino acids 170-227 of human CS1 (SEQ ID NO: 84).

TABLE 11

Amino acid sequences of chimeric CS1 proteins
hu25%/mu75

(SEQ ID NO: 79)
MAGSPTCLTLIYILWQLTGSAASGPVKELVGSVGGAVTFPLKSKVKQVDSIVWTFNTTPL

VTIQPEGVTSQSSNKERIVFPDGLYSMKLSQLKKNDSGAYRAEIYSTSSQASLIQEYVLH

VYKHLSRPKVTIDRQSNKNGTCVINLTCSTDQDGENVTYSWKAVGQGDNQFHDGATLSIA

WRSGEKDQALTCMARNPVSNSFSTPVFPQKLCEDAATDLTSLRG mu25%/hu75%

(SEQ ID NO: 80)
MARFSTYIIFTSVLCQLTVTAASGTLKKVAGALDGSVTFTLNITEIKVDYVVWTFNTFFL

AMVKKDGGTIIVTQNRNRERVDFPDGGYSLKLSKLKKNDSGIYYVGIYSSSLQQPSTQEY

VLHVYEHLSKPKVTMGLQSNKNGTCVTNLTCCMEHGEEDVIYTWKALGQAANESHNGSIL

PISWRWGESDMTFICVARNPVSRNFSSPILARKLCEGAADDPDSSMV

TABLE 11-continued hu50%/mu50%

(SEQ ID NO: 81)
MAGSPTCLTLIYILWQLTGSAASGPVKELVGSVGGAVTFPLKSKVKQVDSIVWTFNTTPL

VTIQPEGGTIIVTQNRNRERVDFPDGGYSLKLSKLKKNDSGIYYVGIYSSSLQQPSTQEY

VLHVYEHLSKPKVTIDRQSNKNGTCVINLTCSTDQDGENVTYSWKAVGQGDNQFHDGATL

SIAWRSGEKDQALTCMARNPVSNSFSTPVFPQKLCEDAATDLTSLRG mu50%/hu50%

(SEQ ID NO: 82)
MARPSTYIIFTSVLCQLTVTAASGTLKKVAGALDGSVTFTLNITEIKVDYVVWTFNTFFL

AMVKKDGVTSQSSNKERIVFPDGLYSMKLSQLKKNDSGAYRAEIYSTSSQASLIQEYVLH

VYKHLSRPKVTMGLQSNKNGTCVTNLTCCMEHGEEDVIYTWKALGQAANESHNGSILPIS

WRWGESDMTFICVARNPVSRNFSSPILARKLCEGAADDPDSSMV hu75%/mu25%

(SEQ ID NO: 83)
MAGSPTCLTLIYILWQLTGSAASGPVKELVGSVGGAVTFPLKSKVKQVDSIVWTFNTTPL

VTIQPEGGTIIVTQNRNRERVDFPDGGYSLKLSKLKKNDSGIYYVGIYSSSLQQPSTQEY

VLHVYEHLSKPKVTMGLQSNKNGTCVTNLTCCMEHGEEDVIYTWKALGQGDNQFHDGATL

SIAWRSGEKDQALTCMARNPVSNSFSTPVFPQKLCEDAATDLTSLRG mu75%/hu25%

(SEQ ID NO: 84)
MARFSTYIIFTSVLCQLTVTAASGTLKKVAGALDGSVTFTLNITEIKVDYVVWTFNTFFL

AMVKKDGVTSQSSNKERIVFPDGLYSMKLSQLKKNDSGAYPAEIYSTSSQASLIQEYVLH

VYKHLSRPKVTIDRQSNKNGTCVINLTCSTDQDGENVTYSWKAVGQAANESHNGSILPIS

WRWGESDMTFICVARNPVSRNFSSPILARKLCEGAADDPDSSMV

Transient Transfection

293/T cells were plated at 2×10⁵ cells per well in 6 well plates. 24 hours later, 0.15 pmol DNA was mixed with FuGene6 (Roche) according to the manufacturer's instructions and added to cells. 24 hours later the cells were transferred to T75 flasks containing 12 ml media with Ultra-low IgG Serum (Invitrogen). 3 days later the supernatant was harvested and the presence of CS1-Fc fusion protein was confirmed and quantitated by detecting the Fc tag by ELISA.

Epitope Mapping ELISA

Human, mouse, or human-mouse chimeric CS1-Fc proteins were assessed for their ability to bind different anti-CS1 antibodies using a sandwich ELISA. The capture antibody, anti-human gamma (Jackson Immunological) was bound overnight to an ELISA plate (Immulon 4 HBX—Thermo-LabSystems) in carbonate buffer at 1.8 µg/ml. After blocking, 100 µl supernatant from 293/T cells transfected with the CS1 constructs was incubated at 37 C for one hour, followed by incubation with anti-CS1 antibodies at 2 µg/ml. Anti-mouse antibodies, conjugated to horseradish peroxidase, were then incubated at 0.5 µg/ml and subsequently detected with 3,3', 5,5' tetramethylbenzidine (Sigma). Each assay was done at least two times with two different transfections.

It has previously been determined that the CS1 antibodies bind human CS1 but not mouse CS1. However, the extracellular domains of CS1 from the two species are similar enough to enable production of chimeras between human and mouse CS1 to localize the regions of the protein to which the antibodies bind. Expression constructs containing chimeras of the extracellular domains of human and mouse CS1 were transfected into 293/T cells and assessed for their ability to bind CS1 antibodies. As expected, the CS1 antibodies bound human CS1 but not mouse CS1 and were found to fall into 3 different epitope groups (Table 12).

TABLE 12

Epitope mapping of CS1 antibodies

| antibody | NIF Fc vector | huCS1 | muCS1 | hu25/mu75 | mu25/hu75 | hu50/mu50 | mu50/hu50 | hu75/mu25 | mu75/hu25 |
|---|---|---|---|---|---|---|---|---|---|
| Luc34 | − | + | − | − | − | + | − | + | − |
| LucX | − | + | − | − | − | + | − | + | − |
| Luc69 | − | + | − | − | − | + | − | + | − |
| Luc90 | − | + | − | − | − | + | − | + | − |
| Luc5 | − | + | − | − | + | + | − | + | − |
| Luc38 | − | + | − | − | + | + | − | + | − |

TABLE 12-continued

Epitope mapping of CS1 antibodies

| antibody | NIF Fc vector | huCS1 | muCS1 | hu25/mu75 | mu25/hu75 | hu50/mu50 | mu50/hu50 | hu75/mu25 | mu75/hu25 |
|---|---|---|---|---|---|---|---|---|---|
| Luc4 | − | + | − | − | + | − | + | − | + |
| Luc12 | − | + | − | − | + | − | + | − | + |
| Luc23 | − | + | − | − | + | − | + | − | + |
| Luc29 | − | + | − | − | + | − | + | − | + |
| Luc32 | − | + | − | − | + | − | + | − | + |
| Luc37 | − | + | − | − | + | − | + | − | + |
| Luc63 | − | + | − | − | + | − | + | − | + |

CS1 antibodies Luc34, LucX, Luc69, and Luc90 bind hu50/mu50, which contains the first 151 amino acids of human CS1 and the second half of mouse CS1. Thus these antibodies bind in the first half of human CS1 extracellular domain. However, none of the antibodies bind either hu25/mu75, which contains the first 67 amino acids of human CS1 or mu25/hu75, which contains amino acids 68-227 of human CS1. Thus, the epitopes for these antibodies overlap both of these regions and could potentially lie at the junction of these constructs, at amino acids 67-68. CS1 antibodies Luc5 and Luc38 bind both hu50/mu50, containing the first 151 amino acids of human CS1, and mu25/hu75, containing amino acids 68-227 of human CS1. Thus, these antibodies bind between amino acids 68-151 of human CS1. The smallest region of human CS1 tested that Luc4, Luc12, Luc23, Luc29, Luc32, Luc37, and Luc63 bind is mu75/hu25. Thus, these antibodies bind the C-terminal 58 amino acids of human CS1 extracellular domain.

This study has grouped the CS1 antibody binding sites into 3 epitope clusters:

(1) the epitope defined by Luc90, which binds to hu50/mu50 (SEQ ID NO: 81). This epitope covers from about amino acid residue 23 to about amino acid residue 151 of human CS1. This epitope is resided within the domain 1 (V domain) of the extracellular domain. This epitope is also recognized by Luc34, LucX (including LucX.1 and LucX.2) and Luc69.

(2) the epitope defined by Luc38, which binds to mu25/hu75 (SEQ ID NO: 80) and hu50/mu50 (SEQ ID NO: 81). This epitope likely covers from about amino acid residue 68 to about amino acid residue 151 of human CS1. This epitope is also recognized by Luc5.

(3) the epitope defined by Lu 63, which binds to mu75/hu25 (SEQ ID NO: 84). This epitope covers from about amino acid residue 170 to about amino acid residue 227 of human CS1. This epitope is resided within domain 2 (C2 domain) of human CS1. This epitope is also recognized by Luc4, Luc12, Luc23, Luc29, Luc32 and Luc37.

It is understood that the examples described above in no way serve to limit the true scope of this invention, but rather are presented for illustrative purposes. All publications, sequences of accession numbers, and patent applications cited in this specification are herein incorporated by reference as if each individual publication, accession number, or patent application were specifically and individually indicated to be incorporated by reference.

DEPOSIT OF HYBRIDOMA: The hybridoma cell line Luc63.2.22, secreting monoclonal antibody Luc63, was deposited with the American Type Culture Collection ("ATCC"), at P.O. Box 1549, Manassas, Va. 20108, on May 6, 2004, in compliance with the Budapest Treaty on the International Recognition of the Deposit of Microorganisms for the Purposes of Patent Procedure on behalf of Protein Design Labs, Inc. (now PDL Biopharma, Inc.). The deposited hybridoma was assigned ATCC accession number PTA-5950.

What is claimed is:

1. A method of treating multiple myeloma, comprising the step of administering to a patient in need thereof a therapeutically effective amount of a combination of:
   (a) a monoclonal anti-CS1 antibody or an anti-CS1 antigen binding fragment, wherein said monoclonal anti-CS1 antibody or anti-CS1 antigen binding fragment binds to a protein encoded by SEQ ID NO:1 and comprises
      (i) a heavy chain variable region with complementarity determining region (CDR) sequences having amino acid sequences of SEQ ID NO:15, SEQ ID NO:16 or SEQ ID NO:87, and SEQ ID NO:17; and
      (ii) a light chain variable region with CDR sequences having amino acid sequences of SEQ ID NO:18, SEQ ID NO:19, and SEQ ID NO:20; and
   (b) velcade.

2. The method of claim 1, wherein the heavy chain variable region has CDR sequences having the amino acid sequences of SEQ ID NO:15, SEQ ID NO:16, and SEQ ID NO:17.

3. The method of claim 1, wherein the heavy chain variable region has CDR sequences having the amino acid sequences of SEQ ID NO:15, SEQ ID NO:87, and SEQ ID NO:17.

4. The method of claim 3, wherein the monoclonal anti-CS1 antibody or anti-CS1 antigen binding fragment is humanized.

5. The method of any one of claims 1-4, wherein the monoclonal anti-CS1 antibody or anti-CS1 antigen binding fragment is an IgG$_1$.

6. The method of claim 3, wherein the heavy chain variable region of the monoclonal antibody or antigen binding fragment comprises the amino acid sequence of SEQ ID NO:41.

7. The method of claim 3 or claim 6, wherein the light chain variable region of the monoclonal antibody or antigen binding fragment comprises the amino acid sequence of SEQ ID NO:44.

8. A method of treating multiple myeloma, comprising the step of administering to a patient in need thereof a therapeutically effective amount of a combination of:
   (a) a conjugate compound comprising a monoclonal anti-CS1 antibody or an anti-CS1 antigen binding fragment linked to an effector moiety, wherein said monoclonal anti-CS1 antibody or anti-CS1 antigen binding fragment binds to a protein encoded by SEQ ID NO:1 and comprises
      (i) a heavy chain variable region with complementarity determining region (CDR) sequences having amino acid sequences of SEQ ID NO:15, SEQ ID NO:16 or SEQ ID NO:87, and SEQ ID NO:17; and
      (ii) a light chain variable region with CDR sequences having amino acid sequences of SEQ ID NO:18, SEQ ID NO:19, and SEQ ID NO:20; and
   (b) velcade.

9. The method of claim 8, wherein the effector moiety is a cytotoxic agent.

10. The method of claim 8, wherein the effector moiety is a detection moiety, an activatable moiety, a chemotherapeutic agent, a lipase, an antibiotic, a chemoattracting agent, an immune modulator or a radioisotope.

11. The method of any one of claims 8-10, wherein the heavy chain variable region has CDR sequences having the amino acid sequences of SEQ ID NO:15, SEQ ID NO:16, and SEQ ID NO:17.

12. The method of claim 11, wherein the heavy chain variable region has CDR sequences having the amino acid sequences of SEQ ID NO:15, SEQ ID NO:87, and SEQ ID NO:17.

13. The method of claim 12, wherein the monoclonal anti-CS1 antibody or anti-CS1 antigen binding fragment is humanized.

14. The method of claim 13, wherein the monoclonal anti-CS1 antibody or anti-CS1 antigen binding fragment is an IgG$_1$.

15. The method of claim 12, wherein the heavy chain variable region of the monoclonal antibody or antigen binding fragment comprises the amino acid sequence of SEQ ID NO:41.

16. The method of claim 15, wherein the light chain variable region of the monoclonal antibody or antigen binding fragment comprises the amino acid sequence of SEQ ID NO:44.

\* \* \* \* \*